US011393593B2

(12) United States Patent
Hisada et al.

(10) Patent No.: US 11,393,593 B2
(45) Date of Patent: Jul. 19, 2022

(54) BIOLOGICAL SIMULATION APPARATUS AND BIOLOGICAL SIMULATION APPARATUS CONTROL METHOD

(71) Applicants: FUJITSU LIMITED, Kawasaki (JP); The University of Tokyo, Tokyo (JP)

(72) Inventors: Toshiaki Hisada, Bunkyo (JP); Seiryo Sugiura, Bunkyo (JP); Takumi Washio, Bunkyo (JP); Junichi Okada, Bunkyo (JP); Ryozo Nagai, Bunkyo (JP); Taro Kariya, Bunkyo (JP); Masahiro Watanabe, Kawasaki (JP); Kohei Hatanaka, Fujisawa (JP); Machiko Nakagawa, Kawasaki (JP); Yoshimasa Kadooka, Kawasaki (JP)

(73) Assignees: FUJITSU LIMITED, Kawasaki (JP); THE UNIVERSITY OF TOKYO, Tokyo (JP)

(*) Notice: Subject to any disclaimer, the term of this patent is extended or adjusted under 35 U.S.C. 154(b) by 1001 days.

(21) Appl. No.: 15/395,000

(22) Filed: Dec. 30, 2016

(65) Prior Publication Data
US 2017/0109496 A1  Apr. 20, 2017

Related U.S. Application Data

(63) Continuation of application No. PCT/JP2014/067832, filed on Jul. 3, 2014.

(51) Int. Cl.
*G16H 50/50* (2018.01)
*G06F 30/23* (2020.01)
(Continued)

(52) U.S. Cl.
CPC ............. *G16H 50/50* (2018.01); *G06F 30/23* (2020.01); *G06F 30/28* (2020.01);
(Continued)

(58) Field of Classification Search
None
See application file for complete search history.

(56) References Cited

U.S. PATENT DOCUMENTS 7,167,816 B1   1/2007  Olovsson
8,554,490 B2 * 10/2013  Tang ..................... A61B 6/466
                                                              702/19
(Continued)

FOREIGN PATENT DOCUMENTS

EP   2 390 802 A2   11/2011
JP   2006-204463    8/2006
(Continued)

OTHER PUBLICATIONS

A Multi-Scale Heart Simulation on Massively Parallel Computers IEEE Xplore | IEEE Conferences | Nov. 1, 2010 | 2010 ACM/IEEE International Conference for High Performance Computing, Networking, Storage and Analysis (pp. 1-11) (Year: 2010).*

(Continued)

*Primary Examiner* — Akash Saxena
(74) *Attorney, Agent, or Firm* — Xsensus LLP

(57) ABSTRACT

In a biological simulation apparatus, an operation unit represents a structure domain where tissues of a biological organ exist by a structure mesh model based on a Lagrange description and a fluid domain where fluid inside the biological organ exists by an ALE fluid mesh model based on an ALE description method. In a fluid-structure interaction simulation, the operation unit deforms the structure mesh model, and then deforms the ALE fluid mesh model so as to form no gap on a first interface between a domain where a site other than a certain site of the biological organ in the structure domain exists and the fluid domain or no overlap with the structure domain. The operation unit captures a position of a second interface between a domain where the (Continued)

certain site exists and the fluid domain by using the ALE fluid mesh model as a reference.

7 Claims, 25 Drawing Sheets

(51) Int. Cl.
  *G06F 30/28* (2020.01)
  *G06F 113/08* (2020.01)
  *G06F 111/10* (2020.01)
(52) U.S. Cl.
  CPC ....... *G06F 2111/10* (2020.01); *G06F 2113/08* (2020.01); *G06T 2207/30048* (2013.01); *G06T 2207/30104* (2013.01)

(56) References Cited

U.S. PATENT DOCUMENTS

| | | | | |
|---|---|---|---|---|
| 9,245,142 | B2* | 1/2016 | Aizawa | G06F 21/6218 |
| 9,405,996 | B2* | 8/2016 | Ionasec | G06T 7/149 |
| 9,449,226 | B2* | 9/2016 | Aizawa | G06F 16/5838 |
| 10,799,191 | B2* | 10/2020 | Kushibe | A61B 6/5217 |
| 10,867,086 | B2* | 12/2020 | Kushibe | G06F 30/20 |
| 2003/0125644 | A1* | 7/2003 | Hamamoto | G06F 30/23 |
| | | | | 600/587 |
| 2006/0149522 | A1* | 7/2006 | Tang | G06F 19/321 |
| | | | | 703/11 |
| 2007/0124128 | A1 | 5/2007 | Connacher et al. | |
| 2008/0020362 | A1* | 1/2008 | Cotin | G16H 50/50 |
| | | | | 434/267 |
| 2008/0101676 | A1* | 5/2008 | Zheng | A61B 6/503 |
| | | | | 382/131 |
| 2008/0262814 | A1* | 10/2008 | Zheng | G16H 50/50 |
| | | | | 703/11 |
| 2008/0319308 | A1* | 12/2008 | Tang | A61B 5/055 |
| | | | | 600/416 |
| 2009/0123050 | A1* | 5/2009 | Ionasec | G06T 7/0016 |
| | | | | 382/131 |
| 2010/0130878 | A1* | 5/2010 | Lasso | G16H 50/50 |
| | | | | 600/500 |
| 2011/0060576 | A1* | 3/2011 | Sharma | G06T 7/0012 |
| | | | | 703/11 |
| 2011/0288834 | A1* | 11/2011 | Yamazaki | G06F 30/23 |
| | | | | 703/2 |
| 2012/0022843 | A1* | 1/2012 | Ionasec | G06T 13/20 |
| | | | | 703/9 |
| 2013/0144573 | A1* | 6/2013 | Sharma | G16H 50/50 |
| | | | | 703/2 |
| 2013/0197881 | A1* | 8/2013 | Mansi | A61N 1/36585 |
| | | | | 703/2 |
| 2013/0243294 | A1* | 9/2013 | Ralovich | G06T 7/0012 |
| | | | | 382/131 |
| 2013/0342217 | A1 | 12/2013 | Hisada et al. | |
| 2014/0071125 | A1* | 3/2014 | Burlina | G06T 17/00 |
| | | | | 345/420 |
| 2014/0214389 | A1* | 7/2014 | Washio | G16B 5/00 |
| | | | | 703/11 |
| 2014/0222354 | A1* | 8/2014 | Krittian | A61B 5/0044 |
| | | | | 702/50 |
| 2014/0257765 | A1* | 9/2014 | Zhang | G06F 30/23 |
| | | | | 703/2 |
| 2014/0316758 | A1* | 10/2014 | Yagi | A61B 5/7275 |
| | | | | 703/9 |
| 2016/0063175 | A1* | 3/2016 | Choi | G06F 19/00 |
| | | | | 703/11 |
| 2017/0032095 | A1* | 2/2017 | Kadooka | G16H 20/40 |
| 2017/0109496 | A1* | 4/2017 | Hisada | G16H 50/50 |

FOREIGN PATENT DOCUMENTS

| | | |
|---|---|---|
| JP | 2011-228878 | 11/2011 |
| JP | 2011-248878 | 12/2011 |
| JP | 2012-24582 | 2/2012 |
| JP | 2012-230394 | 11/2012 |
| WO | WO 2013/031744 A1 | 3/2013 |

OTHER PUBLICATIONS

"Coupled Eulerian-Lagrangian simulations using a level set method," S. Mauch et al., Computational Fluid and Solid Mechanics 2003, Jun. 17-20, 2003, pp. 1448-1453 (Year: 2003).*
"Numerical Study Related to Fluid Structure Interaction Simulation Method of Aortic Valve", Toshiaki Hisada and Takumi Washio, The Japan Society for Industrial and Applied Mathematics, vol. 16, No. 2, pp. 36-50, 2006 (with Partial English Translation) Total 33 pages with original. (Year: 2006).*
"Mathematical Considerations for Fluidstructure Interaction Simulation of Heart Valves", Toshiaki Hisada, Takumi Washio; Bulletin of the Japan Society for Industrial and Applied Mathematics 2006 vol. 16 Issue 2 pp. 142-156; https://doi.org/10.11540/bjsiam.16.2_142 (Year: 2006).*
Spühler, Jeannette H et al. "3D Fluid-Structure Interaction Simulation of Aortic Valves Using a Unified Continuum ALE FEM Model." Frontiers in physiology vol. 9 363. Apr. 16, 2018, doi:10.3389/fphys.2018.00363 (Year: 2018).*
Seiryo Sugiura, et al., "Multi-scale simulations of cardiac electrophysiology and mechanics using the University of Tokyo heart simulator", Progress in Biophysics and Molecular Biology, vol. 110, Issues 2-3, 2012, pp. 380-389, ISSN 0079-6107, (Year: 2012).*
Sara Calandrini, Eugenio Aulisa, "Fluid-structure interaction simulations of venous valves: a monolithic ALE method for large structural displacements", ARXIV ID: 1805.01321, Publication Date: May 3, 2018, pp. 25 (Year: 2018).*
International Search Report dated Jul. 29, 2014 in PCT/JP2014/067832 filed on Jul. 3, 2014 (with English translation).
Toshiaki Hisada, et al., "Mathematical Considerations for Fluidstructure Interaction Simulation of Heart Valves", (with English Abstract), Oyo Suri, vol. 16, (2), 2006, 17 pgs.
Toshiaki Hisada, et al., "Multiscale-Multiphysics Heart Simulator for Medicine and Dug Discovery", Joho Shori, vol. 48, (10), 2007, 9 pgs.
Kazuo Kashiyama, "Zoku Yugen Yosoho ni yoru Nagare no Simulation", Maruzen Publishing Co., Ltd., 2012, 10 pgs.
Extended European Search Report dated Jun. 21, 2017 in Patent Application No. 14896780.5.
Axel Gerstenberger, et al., "An extended Finite Element Method/Lagrange Multiplier Based Approach for Fluid-Structure Interaction" Computer Methods in Applied Mechanics and Engineering, vol. 197, No. 19-20, XP022509620, Mar. 3, 2008, pp. 1699-1714.
Matthias Aechtner, "Arbitrary Lagrangian-Eulerian Finite Element Modelling of the Human Heart" Retrieved from the Internet: URL:https://www.nada.kth.se/utbildning/grukth/exjobb/rapportlistor/2009/rapporter09/aechtner_matthias_09022.pdf, XP055380679, Jan. 1, 2009, pp. 1-33 and Cover Pages.
M.A. Castro, et al., "Computational Fluid Dynamics Modeling of Intracranial Aneurysms: Effects of Parent Artery Segmentation on Intra-Aneurysmal Hemodynamics", American Journal of Neuroradiology, 2006, 7 pgs.
Elaine Tang, et al., "Geometric Characterization of Patient-Specific Total Cavopulmonary Connections and its Relationship to Hemodynamics", JACC Cardiovascular Imaging, vol. 7, (3), 2014, 10 pgs.
Hiroshi Watanabe, et al., "Multiphysics Simulation of Left Ventricular Filling Dynamics Using Fluid-Structure Interaction Finite Element Method", Biophysical Journal, vol. 87, 2004, 12 pgs.
J. De Hart, et al., "A three-dimensional computational analysis of fluid-structure interaction in the aortic valve", Journal of Biomechanics, vol. 36, 2003, 10 pgs.
Qun Zhang, et al., "Analysis of fluid-structure interaction problems with structural buckling and large domain changes by ALE finite element method", Computer Methods in Applied Mechanics and Engineering, vol. 190, 2001, 17 pgs.

* cited by examiner

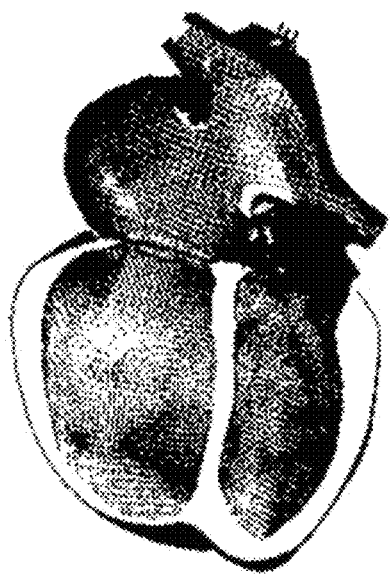 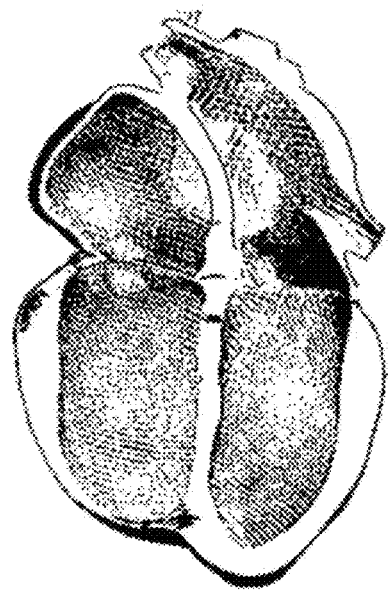
PREOPERATIVE GEOMETRIC MODEL
FIG. 18A
POSTOPERATIVE GEOMETRIC MODEL
FIG. 18B

BIOLOGICAL SIMULATION APPARATUS AND BIOLOGICAL SIMULATION APPARATUS CONTROL METHOD

CROSS-REFERENCE TO RELATED APPLICATION

This application is a continuation application of International Application PCT/JP2014/067832 filed on Jul. 3, 2014 which designated the U.S., the entire contents of which are incorporated herein by reference.

FIELD

The embodiments discussed herein relate to a biological simulation apparatus and a biological simulation apparatus control method.

BACKGROUND

Advances in computational mechanics using computers are being applied not only to the industrial field but also to biomechanics. For example, a simulation of the blood flow in a cerebral aneurysm and a simulation of the blood flow after the Fontan procedure on a heart have recently been performed. As more advanced applications, fluid-structure interaction simulations such as an interaction simulation of heart pulsation and blood flow and an interaction simulation of heart valves and blood flow have been performed. A fluid-structure interaction simulation is a numerical simulation in which a technique of analyzing fluid and a technique of analyzing a structure are combined with each other. This numerical simulation is performed to analyze a dynamic problem in which the fluid and the structure motion while interacting with each other.

Examples of a technique for the interaction simulation of heart pulsation and blood flow include the following two methods. In one method, an ALE (Arbitrary Lagrangian Eulerian) method is applied to the fluid analysis, and interaction of the fluid and the structure is performed. In the other method, the interaction of the fluid and the structure is performed by using the Lagrange multiplier method.

The fluid-structure interaction analysis technique based on the ALE method tracks the interface between the blood as the fluid and the myocardial wall as the structure, namely, between the blood and the myocardial wall. In addition, this technique solves a motion equation of the blood described on the ALE fluid mesh that arbitrarily motions and deforms inside the fluid domain while maintaining consistency with the structure mesh that motions and deforms with material points based on the Lagrange description method on the interface. This technique is a highly accurate and stable technique. However, in the technique, there may be a limit of deformation which ensures the soundness of the mesh. Thus, it is difficult to track a structure such as a heart valve that undergoes very large deformation. The interaction analysis technique based on the ALE method belongs to a technique generally called an interface tracking method. The Lagrange multiplier method is a calculation technique for obtaining extreme values of a function with a constraint condition.

The fluid-structure interaction analysis method using the Lagrange multiplier method is an approximate solution method in which motion equations of the structure and the fluid are combined by using incompressibility of the fluid domain near a structural interface defined suitably by a delta function as a constraint condition. While the accuracy of the fluid-structure interaction analysis method using the Lagrange multiplier method is less than that of the ALE method used in the interaction with the heart wall, since the fluid mesh does not need to be matched with the structural interface, there is no risk of mesh failure. The fluid-structure interaction analysis method using the Lagrange multiplier method belongs to a technique generally called an interface capturing method. In addition, a mesh in the spatially-fixed Euler description method has conventionally been used as a fluid mesh in the interface capturing method.

See, for example, the following documents:
Japanese Laid-open Patent Publication No. 2006-204463;
Japanese Laid-open Patent Publication No. 2011-248878;
M. A. Castro, C. M. Putman, J. R. Cebral, "Computational fluid dynamics modeling of intracranial aneurysms: effects of parent artery segmentation on intra-aneurysmal hemodynamics", American Journal of Neuroradiology September 2006 27: 1703-1709;
Elaine Tang, Maria Restrepo, Christopher M. Haggerty, Lucia Mirabella, James Bethel, Kevin K. Whitehead, Mark A. Fogel, Ajit P. Yoganathan, "Geometric Characterization of Patient-Specific Total Cavopulmonary Connections and its Relationship to Hemodynamics", JACC Volume 7, Issue 3, March 2014, pp. 215-224;
H. Watanabe, S. Sugiura, H. Kafuku, T. Hisada, "Multiphysics simulation of left ventricular filling dynamics using fluid-structure interaction finite element method", Biophysical Journal, Vol. 87, September 2004, pp. 2074-2085;
J. De Hart, G. W. M. Peters, P. J. G. Schreurs, F. P. T. Baaijens, "A three-dimensional computational analysis of fluid-structure interaction in the aortic valve", Journal of biomechanics, Vol. 36, Issue 1, January 2003, pp. 103-112;
Qun Zhang, Toshiaki Hisada, "Analysis of fluid-structure interaction problems with structural buckling and large domain changes by ALE finite element method", Computer Methods in Applied Mechanics and Engineering, Volume 190, Issue 48, 28 Sep. 2001, Pages 6341-6357; and
Toshiaki Hisada, Takumi Washio, "Mathematical Considerations for Fluid-structure Interaction Simulation of Heart Valves", The Japan Society for Industrial and Applied Mathematics, Vol. 16, No. 2, 27 Jun. 2006, pp. 36-50.

A heart simulation generally includes an electrical excitation propagation simulation and a mechanical pulsation simulation. Associating these two simulations with each other is important in performing a more realistic heart simulation on a biological body. In addition, collectively handling the pulsation of the heart wall and the blood flow therein without a contradiction in the mechanical pulsation simulation is important in not only accurately evaluating mechanical responses of the two but also handling clinically necessary indices (blood pressure, blood flow, etc.). In addition, motions of heart valves are often problems in actual heart diseases. Thus, to perform a more realistic heart simulation, it is appropriate to collectively handle the pulsation of the heart wall, the luminal blood flow, and the heart valves without a contradiction in the pulsation simulation. In addition, if a simulation of the entire heart including its valves can be performed highly accurately, the simulation can be used more widely.

As a method of stably and highly accurately performing the fluid-structure interaction analysis between the heart wall and the luminal blood, there is an interface-tracking fluid-structure interaction simulation technique in which the ALE method is used for the blood domain inside the heart.

With this technique, a fluid equation is described from an ALE mesh that motions and deforms. However, it is difficult to track the interface of a structure such as a heart valve that undergoes very large and complex deformation. Thus, the ALE method cannot be applied. On the other hand, while the interface-capturing fluid-structure interaction simulation using the Lagrange multiplier method is inferior in stability and analysis accuracy, interaction analysis between a structure that undergoes large and complex deformation and blood can be performed. However, the conventional interface-capturing analysis methods that have been developed are only for fluid described from the spatially fixed Euler mesh. Namely, no method has been developed yet for fluid described from a mesh that motions and deforms such as an ALE mesh. Thus, analysis of the pulsation of a heart including a valve structure has remained as a very difficult fluid-structure interaction problem.

SUMMARY

According to one aspect, there is provided a biological simulation apparatus including: a memory configured to hold a geometric model that represents a structure of a biological organ; and a processor configured to perform a procedure including: representing, among domains in the geometric model, a structure domain in which tissues of the biological organ exist by using a structure mesh model based on a Lagrange description, representing a fluid domain in which fluid inside the biological organ exists by using an ALE (Arbitrary Lagrangian Eulerian) fluid mesh model based on an ALE description method, and performing a fluid-structure interaction simulation that obtains ever-changing equilibrium conditions by deforming the structure mesh model in accordance with a motion of the biological organ along with a progress of the simulation, generating a deformed ALE fluid mesh model by deforming the ALE fluid mesh model in such a manner that no gap is formed on a first interface located between a domain in which a site other than a certain site of the biological organ in the structure domain exists and the fluid domain or no overlap is formed with the structure domain, tracking the first interface by using the deformed ALE fluid mesh model, capturing a position of a second interface located between a domain in which the certain site in the structure domain exists and the fluid domain by using the deformed ALE fluid mesh model as a reference, and simultaneously solving both motions of the biological organ and the fluid therein, including the interaction of the biological organ and the fluid.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 18A and 18B illustrate examples of visualization of parts of simulation results obtained before and after an operation;

DESCRIPTION OF EMBODIMENTS

Figure 1:
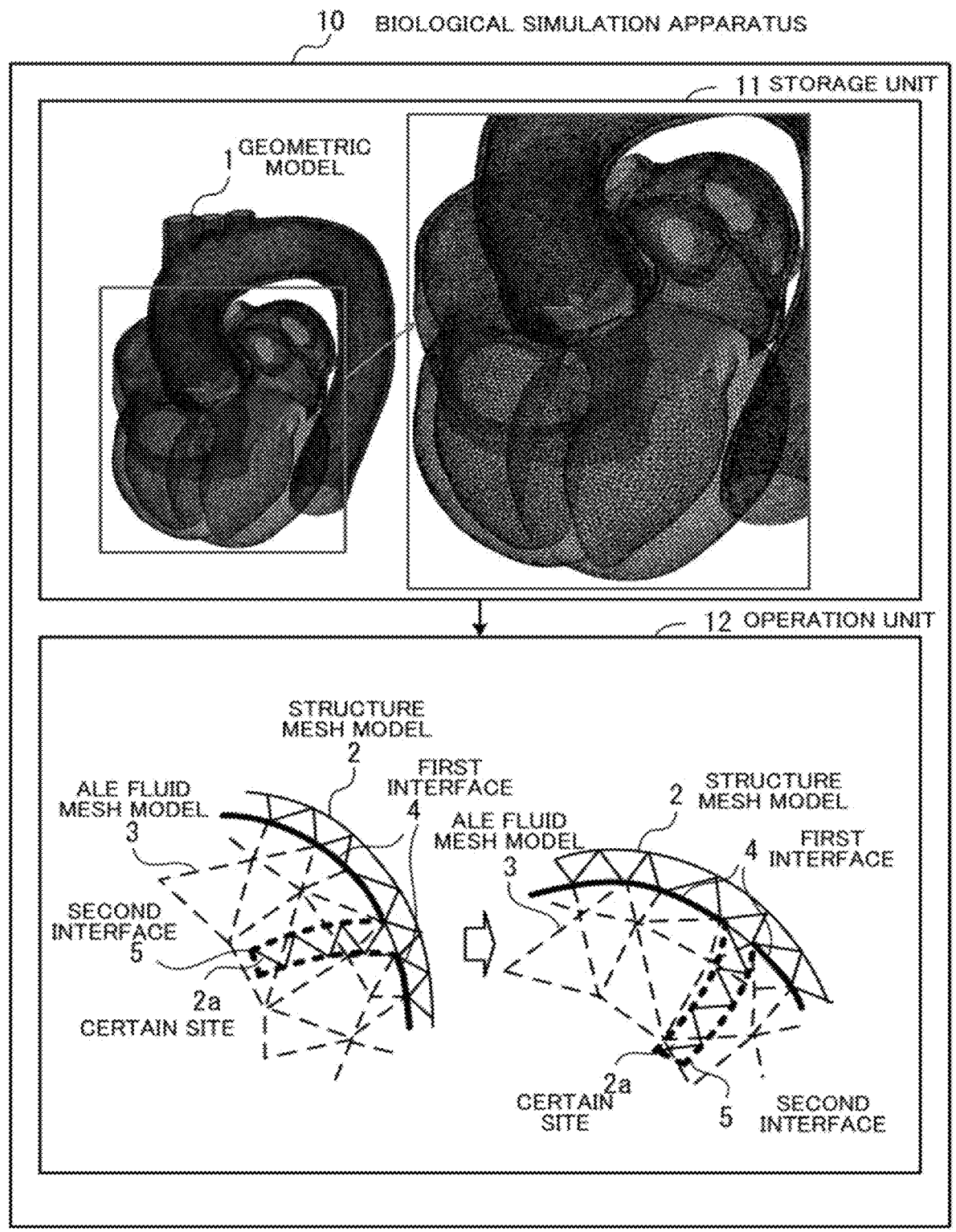
FIG. 1 illustrates a functional configuration example of an apparatus according to a first embodiment.

Hereinafter, embodiments will be described below with reference to the accompanying drawings, wherein like reference characters refer to like elements throughout. A plurality of embodiments may be combined with each other without a contradiction.

First Embodiment

FIG. 1 illustrates a functional configuration example of an apparatus according to a first embodiment. A biological simulation apparatus 10 includes a storage unit 11 and an operation unit 12.

The storage unit 11 holds a geometric model 1 that represents a structure of a biological organ. For example, the biological organ is a human heart.

On the basis of the geometric model 1, the operation unit 12 simultaneously solves both the behavior of the biological organ and the motion of the fluid therein, including the interaction of the biological organ and the fluid, and performs a fluid-structure interaction simulation that obtains ever-changing equilibrium conditions. When performing the fluid-structure interaction simulation, the operation unit 12 generates finite element mesh models on the basis of the geometric model 1. For example, the operation unit 12 generates a structure mesh model 2 that represents a structure domain in which the tissues of the biological organ exist and an ALE fluid mesh model 3 that represents a fluid domain in which the fluid inside the biological organ exists. For example, among the domains in the geometric model 1, the operation unit 12 represents the structure domain in which the tissues of the biological organ exist by using the structure mesh model 2 based on the Lagrange description and the fluid domain in which the fluid inside the biological organ exists by using the ALE fluid mesh model based on the ALE description method. Among the interfaces made by the structure domain and the fluid domain, the operation unit 12 determines an interface between a domain in which a site other than a certain site 2a of the biological organ exists and the fluid domain to be a first interface 4. In addition, among the interfaces made by the structure domain and the fluid domain, the operation unit 12 determines an interface between a domain in which the certain site 2a of the biological organ exists and the fluid domain to be a second interface 5. For example, the certain site 2a is a site protruding into the domain in which the ALE fluid mesh model 3 exists. For example, the certain site 2a is a heart valve.

Along with the progress of the fluid-structure interaction simulation, the operation unit 12 deforms the structure mesh model 2 in accordance with the motion of the biological organ. In addition, the operation unit 12 generates a deformed ALE fluid mesh model 3 by deforming the ALE fluid mesh model 3 by using an interface-tracking analysis method in such a manner that the first interface 4 is tracked. More specifically, the ALE fluid mesh model 3 is deformed in such a manner that no gap is formed on the first interface 4 or no overlap is formed with the structure mesh model 2 (the structure domain). Namely, the first interface 4 is tracked by using the deformed ALE fluid mesh model 3. Movement of nodes inside the deformed ALE fluid mesh model 3 is artificially controlled separately from the motion of the fluid so that the soundness of each of the meshes is maintained. In addition, when performing the fluid-structure interaction simulation, the operation unit 12 captures the position of the second interface 5 using the deformed ALE fluid mesh model 3 as a reference by using an interface-capturing analysis method. For example, on the coordinate space for defining the shape of the ALE fluid mesh model 3, the coordinates of the second interface 5 are calculated.

In this way, the biological simulation apparatus 10 performs a highly accurate fluid-structure interaction simulation on a biological organ having a deformable site that has an interface difficult to track. Namely, a highly accurate simulation is performed by deforming the ALE fluid mesh model 3 in accordance with the interface-tracking analysis method and by tracking the first interface 4 with the deformed the ALE fluid mesh model 3. In addition, the certain site 2a such as a heart valve, which significantly motions and which has an interface that is difficult to track by using the interface-tracking analysis method, is captured on the ALE fluid mesh model 3 by using the interface-capturing analysis method. In this way, the biological simulation apparatus 10 performs a fluid-structure interaction simulation on a biological organ having a site that has an interface difficult to track. For example, the ALE method may be used as the interface-tracking analysis method. In addition, for example, a method based on the Lagrange multiplier method may be used as the interface-capturing analysis method (see, for example, T. Hisada et al., "Mathematical Considerations for Fluid-structure Interaction Simulation of Heart Valves").

The term "virtual operation" used hereinafter indicates a virtual operation that is performed on a biological data in a computer. Namely, a virtual operation is different from an actual operation performed by a doctor.

The storage unit 11 may hold a plurality of postoperative geometric models which represent structures of the biological organ that are obtained by performing a plurality of virtual operations using different operative procedures, respectively, on the biological organ. In this case, the operation unit 12 performs a fluid-structure interaction simulation on each of the plurality of postoperative geometric models and displays simulation results of the plurality of virtual operations on a monitor or the like for comparison. In this way, an appropriate operative procedure can accurately be determined before a doctor performs an actual operation.

In addition, the operation unit 12 may display possible techniques usable in a virtual operation on a monitor or the like and generate a postoperative geometric model by deforming the geometric model 1 in accordance with a selected technique. For example, the operation unit may generate a postoperative geometric model by deforming the geometric model 1 in accordance with a selected technique. After generating a postoperative geometric model, the operation unit 12 stores the generated postoperative geometric model in the storage unit 11. Examples of the possible techniques used in a virtual operation include techniques used in a medical virtual operation and techniques used in a surgical virtual operation. The medical virtual operation is an operation performed without cutting open the chest, such as an operation using a catheter. The surgical operation is an operation performed by cutting open the chest, such as coronary circulation bypass surgery.

When creating a virtual postoperative geometric model based on a medical virtual operation, for example, the operation unit 12 displays possible techniques usable in the medical virtual operation on a monitor or the like and deforms the geometric model 1 in accordance with a selected technique. In this way, a postoperative geometric model can be generated in accordance with the procedure of the medical virtual operation. Likewise, the operation unit 12 displays possible techniques usable in a surgical operation on a monitor or the like and deforms the geometric model 1 in accordance with a selected technique. In this way, a postoperative geometric model can be generated in accordance with the procedure of the surgical operation. By preparing possible techniques of medical and surgical virtual operations, a postoperative geometric model in accordance with an operation assumed by a doctor can be generated, whether the doctor is a physician or a surgeon.

After performing a fluid-structure interaction simulation on each of the geometric models obtained by a plurality of virtual operations, the operation unit 12 can evaluate a simulation result of each of the plurality of virtual operations in view of a predetermined reference and rearrange and display the plurality of operations in view of the evaluation results. In this way, the doctor can easily determine the effectiveness of an individual operative procedure.

For example, the operation unit 12 may be realized by a processor of the biological simulation apparatus 10. In addition, for example, the storage unit may be realized by a memory of the biological simulation apparatus 10.

Second Embodiment

A second embodiment provides a prognosis prediction system that predicts prognosis of a biological body (for example, a patient) on the basis of the content of an operation on its heart. This prognosis prediction system is an example of the biological simulation apparatus 10 according to the first embodiment.

In the prognosis prediction system according to the second embodiment, a pulsation simulation based on a fluid-structure interaction of the heart wall, blood flow, and heart valves is performed by combining an interface-tracking analysis method and an interface-capturing analysis method with each other without a contradiction. In addition, the pulsation simulation is linked with an electrical excitation propagation simulation. In this way, a heart simulation that can be used clinically sufficiently is performed. As a result, a result from a cardiovascular operation (and a treatment on a heart) can accurately be predicted per biological body. In addition, when there are a plurality of treatment options, the most appropriate treatment can be selected. In addition, the results can be used for explanation to others (doctors and patients) and for medical education.

Namely, the heart simulation generally includes an electrical excitation propagation simulation and a mechanical pulsation simulation. Associating these two simulations with each other is important in performing a more realistic heart simulation. In addition, collectively handling the pulsation of the heart wall and the blood flow therein without a contradiction in the mechanical pulsation simulation is important in not only accurately evaluating mechanical responses of the two but also handling clinically necessary indices (blood pressure, blood flow, etc.). In addition, the motions of the heart valves are often problems in actual heart diseases. Thus, to perform a more realistic heart simulation, it is appropriate to collectively handle the pulsation of the heart wall, the luminal blood flow, and the heart valves without a contradiction in the pulsation simulation. Thus, in the prognosis prediction system according to the second embodiment, two kinds of interaction analysis techniques, namely, an interface-tracking analysis method and an interface-capturing analysis method, are combined with each other without a contradiction so that the motion of the entire heart including the valves can suitably be simulated.

In addition, in the prognosis prediction system according to the second embodiment, pre-processing is performed in which processing suitable for a heart operation based on the fluid-structure interaction simulation interactively proceeds while receiving a doctor's approval. In addition, in the prognosis prediction system according to the second embodiment, processing (post-processing) in which simulation results are analyzed and ranked on the basis of evaluation values which a clinician considers important is performed. In this way, the pulsation of a heart having a topologically arbitrary three-dimensional (3D) shape can be comprehensively reproduced. In addition, by simulating a virtual operation on the reproduced heart, modeling, pulsation analysis, and visualization can be performed.

Hereinafter, the fluid-structure interaction simulation according to the second embodiment will be described in detail. The fluid-structure interaction simulation to be described below is also an example of the fluid-structure interaction simulation according to the first embodiment. In the first or second embodiment, a simulation using fluid-structure interaction analysis in which the ALE method and the Lagrange multiplier method are combined with each other is performed.

Figure 2:
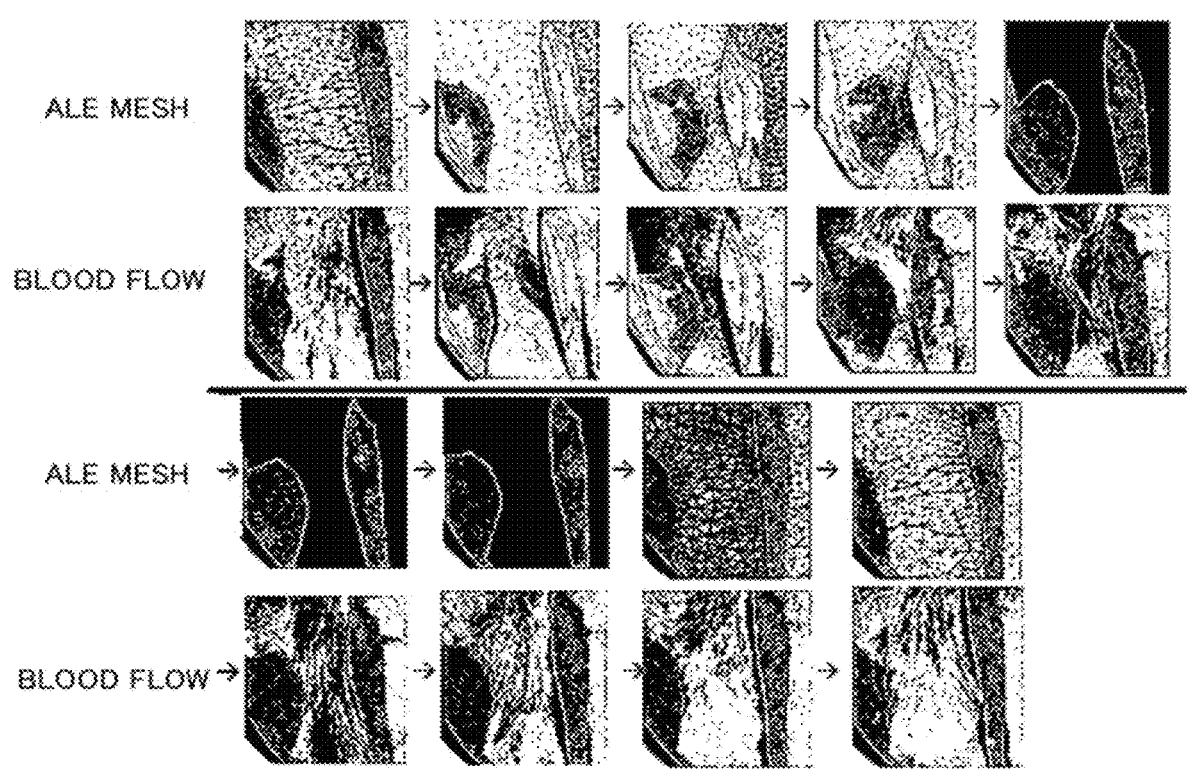
FIG. 2 illustrates examples of fluid-structure interaction analysis based on an interface-tracking analysis method using an ALE mesh when the biological organ is a heart.

FIG. 2 illustrates examples of fluid-structure interaction analysis based on an interface-tracking analysis method using an ALE mesh when the biological organ is a heart. FIG. 2 illustrates an ALE mesh used in the analysis and blood flow obtained as an analysis result. When an interface of the heart deforms, the ALE mesh also deforms with the deformation of the heart. In addition, the fluid velocity (fluid velocity vectors) and the pressure of the blood are analyzed on the coordinate system in which the deformable ALE mesh is defined. In this way, accurate analysis is performed.

However, there is a limit to the deformation of the ALE mesh. Thus, it is difficult to track an interface of a site that significantly deforms such as a heart valve by using a mesh model based on the ALE fluid mesh.

Figure 3:
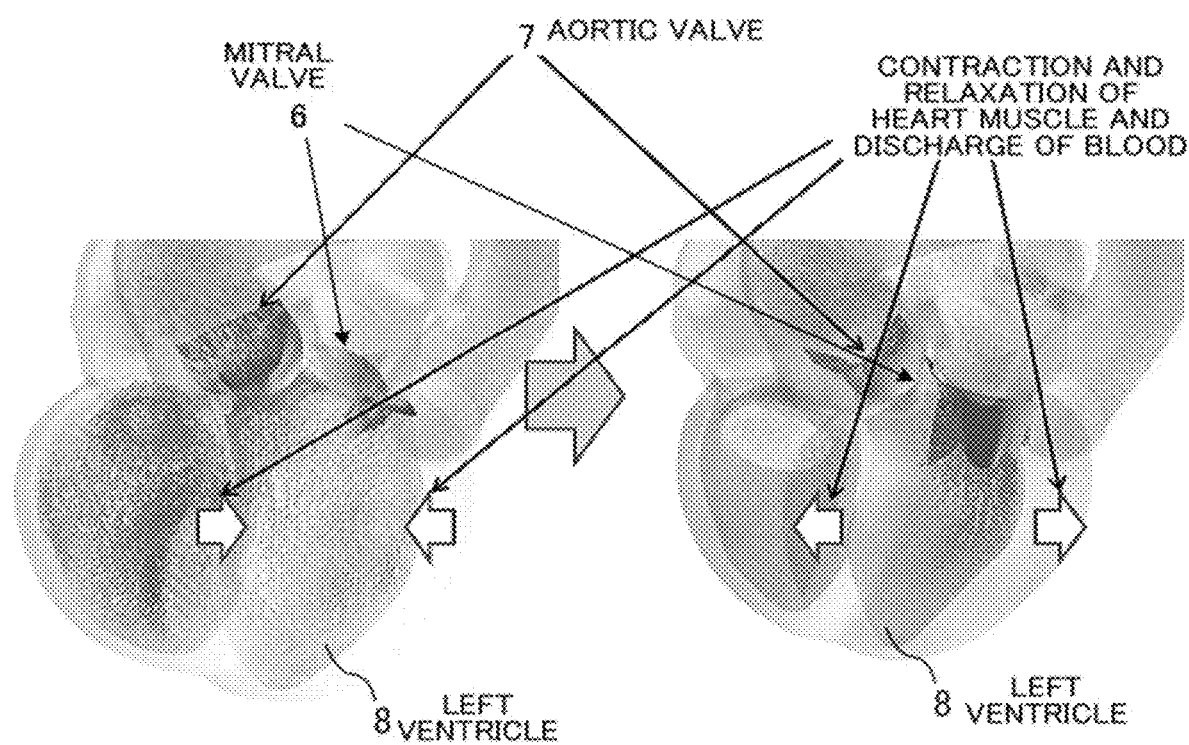
FIG. 3 illustrates the behavior of a heart and the motion of valves.

FIG. 3 illustrates the behavior of a heart and the motions of valves. The left portion in FIG. 3 illustrates a heart when the ventricles contract, and the right portion in FIG. 3 illustrates the heart when the ventricles relax. For example, when the heart muscle of a left ventricle 8 contracts, an aortic valve 7 opens, and the blood in the left ventricle 8 is discharged. In this state, a mitral valve 6 is closed. When the heart muscle of the left ventricle 8 relaxes, the mitral valve 6 opens, and blood flows into the left ventricle 8. In this state, the aortic valve 7 is closed. In this way, an individual valve opens or closes in accordance with the pulsation of the heart. When the heart motions, an individual valve deforms with the opening and closing operations more significantly than the atria and ventricles deform with the contraction and relaxation of the heart muscles. It is difficult to track such valves that deform significantly by using a mesh model based on the ALE mesh.

In contrast, with the interface-capturing interaction analysis technique using the Lagrange multiplier method, since the fluid mesh does not track an interface, the fluid around the heart valves can also be analyzed.

Figure 4A:
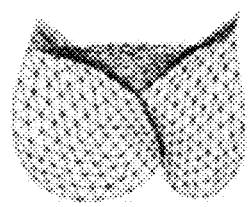
FIGS. 4A to 4C illustrate an example of fluid-structure interaction analysis based on an interface-capturing analysis method using the Lagrange multiplier method.
Figure 4B:
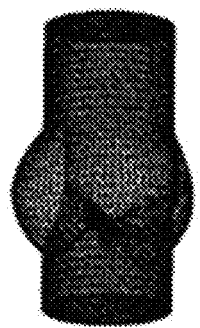
Figure 4C:
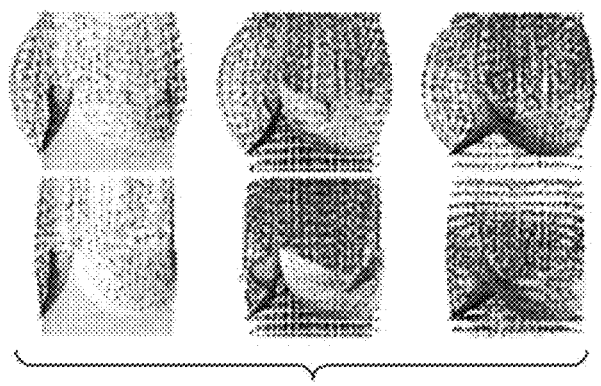

FIGS. 4A to 4C illustrate an example of fluid-structure interaction analysis based on an interface-capturing analysis method using the Lagrange multiplier method. FIG. 4A illustrates a structure mesh model of an aortic valve created independently from a fluid mesh model. FIG. 4B illustrates a spatially-fixed Euler fluid mesh model representing the fluid domain inside an aorta. FIG. 4C illustrates simulation results in which the fluid velocities of the blood are indicated by vectors. Assuming that the wall of the aorta is a rigid body and does not deform, the fluid mesh can be represented by a spatially-fixed Euler mesh.

In this way, in conventional fluid-structure interaction analysis based on the Lagrange multiplier method, analysis using a spatially-fixed Euler fluid mesh model has been performed. Thus, fluid-structure interaction analysis can be performed on a site that undergoes extreme deformation such as a valve, and change of the blood flow around the valve over time can be analyzed, for example. However, in the fluid-structure interaction analysis based on the Lagrange multiplier method, since an interface is not tracked, the stability and analysis accuracy of this analysis are less than those of the fluid-structure interaction analysis based on the interface tracking method using the ALE mesh.

Thus, in the second embodiment, an interface that can be tracked by the interface-tracking analysis method is tracked by using a deformable ALE mesh, and an interface that is difficult to track such as a valve is captured from the deformable ALE mesh.

Figure 5A:
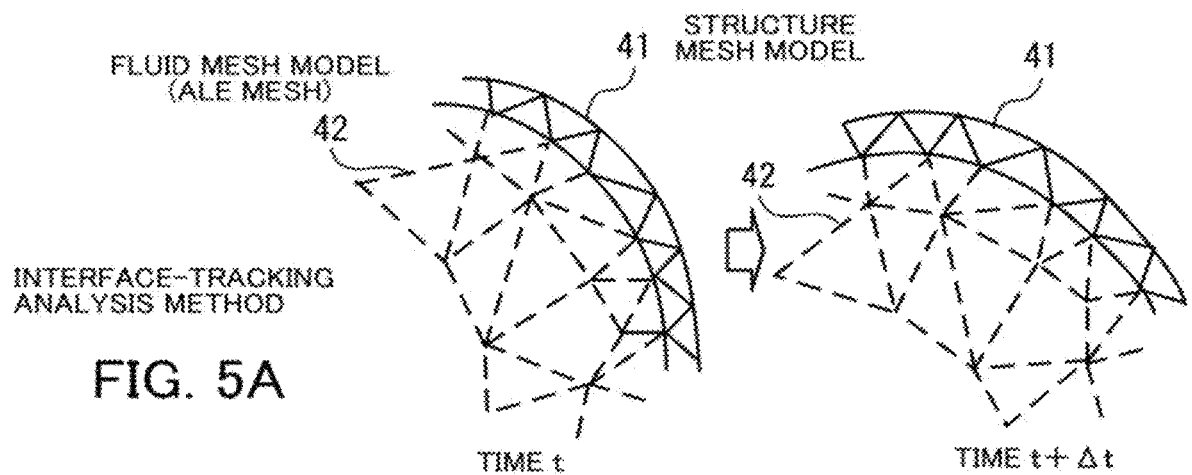
FIGS. 5A to 5C illustrate analysis techniques that are compared with each other.
Figure 5B:
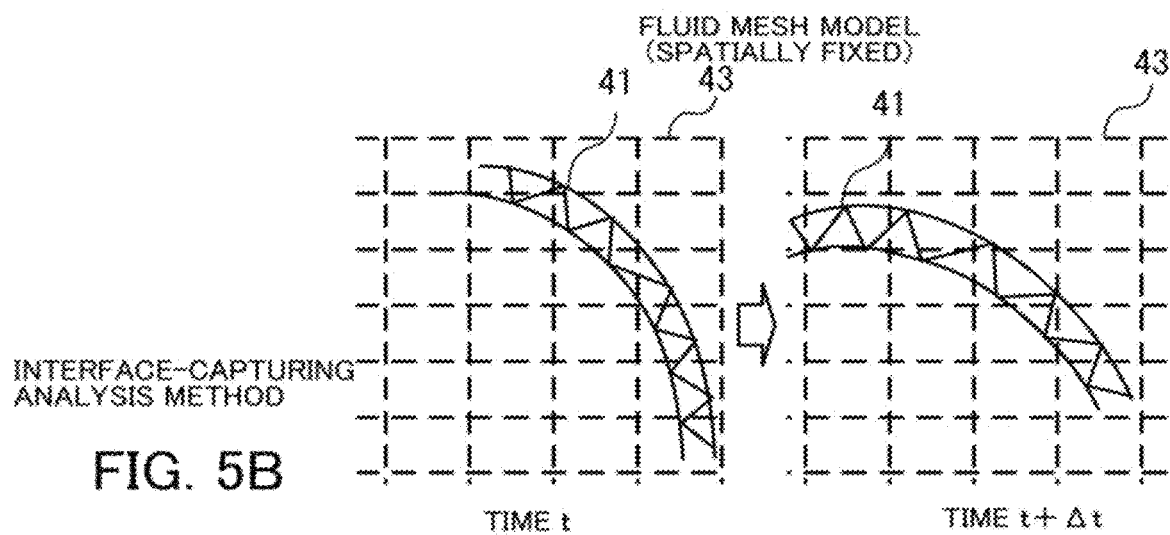
Figure 5C:
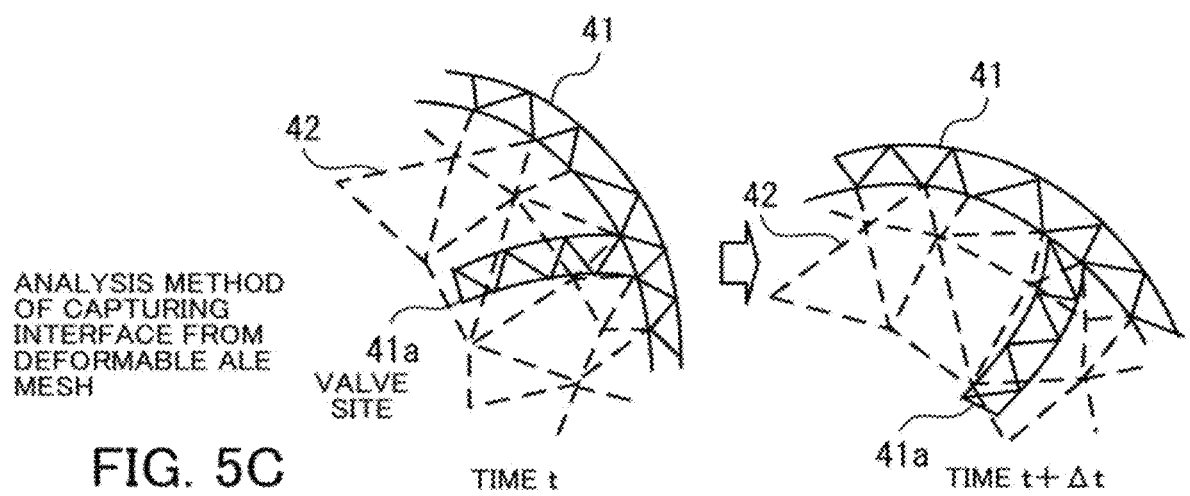

FIGS. 5A to 5C illustrate analysis techniques that are compared with each other. FIG. 5A illustrates an interface-tracking analysis method using the ALE method. FIG. 5B illustrates an analysis method in which an interface is captured from a spatially-fixed Euler mesh. FIG. 5C illustrates an analysis method in which an interface is captured from a deformable ALE mesh.

A structure mesh model 41 representing a structure domain in which the tissues of a biological organ exist is deformed as the simulation time progresses from t to t+Δt. When the interface-tracking analysis method is used, a ALE fluid mesh model 42 formed by the ALE mesh also deforms as the structure mesh model 41 deforms. However, since a fluid mesh model 43 based on the interface-capturing analysis method is spatially fixed, the fluid mesh model 43 does not deform even when the structure mesh model 41 deforms.

In the analysis method in which an interface is captured from a deformable mesh, an interface of the structure mesh model 41 in a trackable range is tracked by using the deformable ALE fluid mesh model 42. Regarding an untrackable site (for example, a valve site 41a), the position of the interface of the corresponding site is calculated on the coordinate system in which the ALE fluid mesh model 42 is defined. In this way, an interface of a site that significantly deforms such as the valve site 41a can be captured.

Next, interface-tracking and -capturing methods will be described in detail.

Figure 6B:
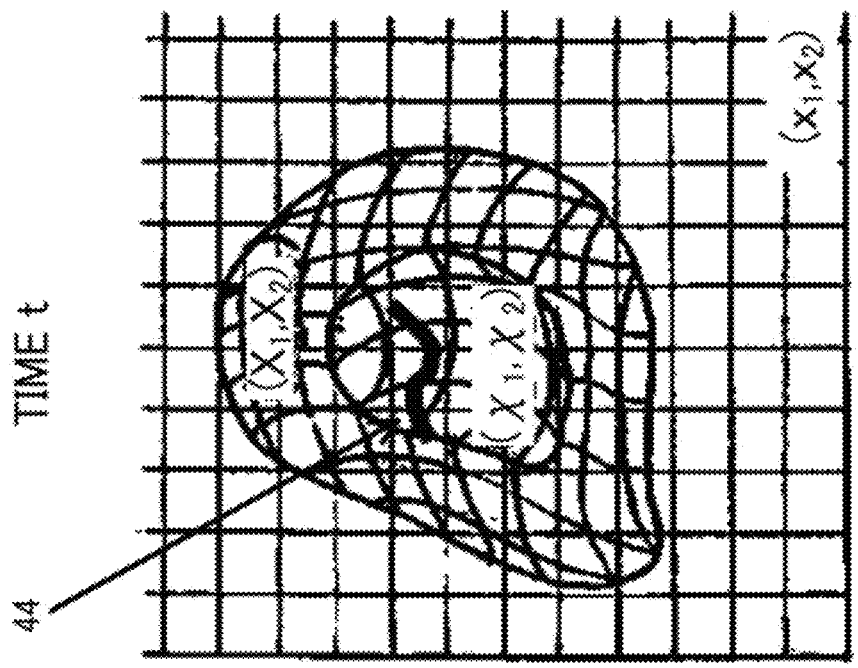
FIGS. 6A and 6B illustrate coordinate systems for interface tracking and capturing.
Figure 6A:
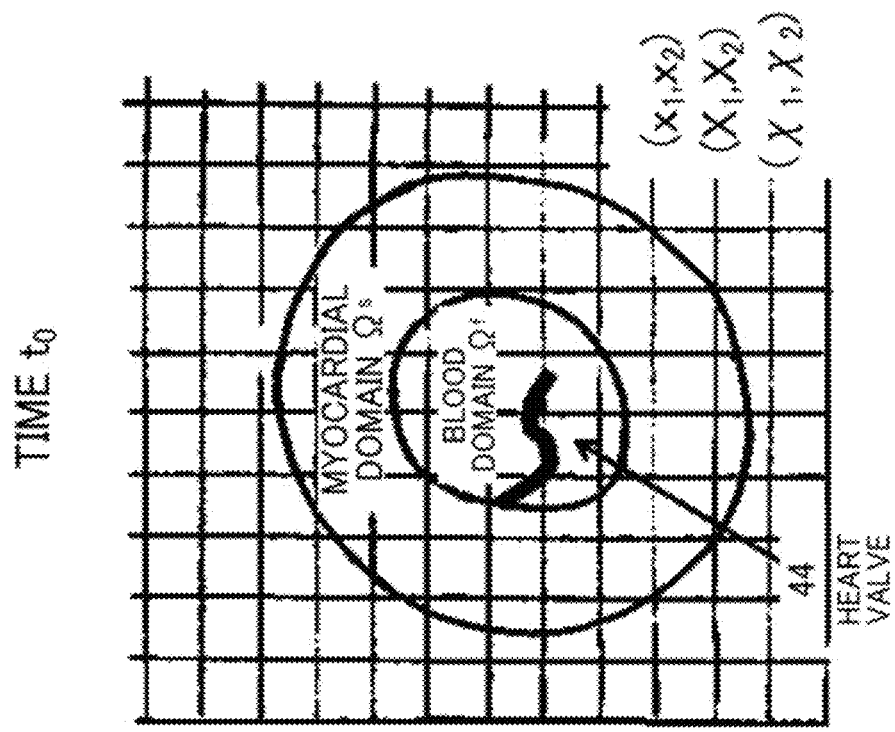

FIGS. 6A and 6B illustrate coordinate systems for interface tracking and capturing. FIGS. 6A and 6B illustrate an Euler (space) coordinate system $(x_1, x_2)$, a Lagrangian (material) coordinate system $(X_1, X_2)$, and an ALE coordinate system $(\chi_1, \chi_2)$ that arbitrarily motions and deforms. A myocardial domain $\Omega^S$ is represented by the Lagrangian coordinate system. A blood domain $\Omega^f$ is represented by the ALE coordinate system. A heart valve 44 is protruding into the blood domain $\Omega^f$. While 3D representation is used in reality, two dimensional (2D) representation is used herein for simplicity.

An absolute velocity $v_i$ at a material point X, a velocity $w_i$ at the material point X observed from the ALE coordinate system, and a velocity ($v_i$ with "^") in the ALE coordinate system controlled by an analyst are expressed as equations (1) to (3), respectively.

$$v_i = \left.\frac{\partial x_i(X, t)}{\partial t}\right|_X \quad (1)$$

$$w_i = \left.\frac{\partial \chi_i(X, t)}{\partial t}\right|_X \quad (2)$$

$$\hat{v}_i = \left.\frac{\partial x_i(\chi, t)}{\partial t}\right|_\chi \quad (3)$$

If an equation of the motion of a continuum body derived from the law of conservation of momentum and the law of conservation of mass are written from the ALE coordinate system, equations (4) are (5) are obtained.

$$\hat{\rho}\left.\frac{\partial v_i}{\partial t}\right|_\chi + \hat{\rho}w_j\frac{\partial v_i}{\partial x_j} = \frac{\partial \hat{\Pi}_{ji}}{\partial x_j} + \hat{\rho}g_i \quad (4)$$

$$\left.\frac{\partial \hat{\rho}}{\partial t}\right|_\chi + \frac{\partial \hat{\rho}w_i}{\partial x_i} = 0 \quad (5)$$

In the above equations, ρ with "^" and Π with "^" indicate the mass density and the 1st Piola-Kirchhiff stress tensor defined by using the reference configuration in the ALE coordinate system as a reference. The second term on the right-hand side of equation (4) represents arbitrary body force.

For example, the motion equation of the luminal blood of the heart is described from the ALE coordinate system different from the Langrangian coordinate system used for the myocardial domain as illustrated in FIG. 1 (See, for example, M. A. Castro et al., "Computational fluid dynamics modeling of intracranial aneurysms: effects of parent artery segmentation on intra-aneurysmal hemodynamics" and E. Tang et al., "Geometric Characterization of Patient-Specific Total Cavopulmonary Connections and its Relationship to Hemodynamics"), and the valve motions in the space of the ALE coordinate system. Thus, to cause the blood and the valve to interact with each other by applying the interface-capturing analysis method based on the Lagrange multiplier method proposed in "Multi-physics simulation of left ventricular filling dynamics using fluid-structure interaction finite element method" by H. Watanabe et al., the ALE coordinate system is basically used as the common coordinate system. Thus, the law of conservation of mass in one-side blood domain $\Omega^K$ (K=1, 2) defined by a delta function near a point A on the valve is imposed as expressed by the equation (6). The match between a blood velocity $v_F$ and the velocity components in a normal direction $n^C$ regarding a valve velocity $v_s$ is imposed as expressed by the equation (7), where $\Gamma^C$ represents an interface.

$$\int_{\Omega^K} \delta(\chi - \chi_A)\left(\left.\frac{\partial \hat{\rho}}{\partial t}\right|_\chi + \frac{\partial \hat{\rho}w_i}{\partial x_i}\right)d\Omega^K = 0 \quad (6)$$

$$K = 1, 2$$

$$n^C \cdot (v_F(\chi) - v_S(\chi)) = 0 \text{ on } \Gamma^c \quad (7)$$

However, since the formulation based on the concept of the reference configuration of the ALE coordinate system complicates the equations, the equations including the motion equation of the blood are converted to be expressed in the Euler coordinate system. Consequently, since equations (4) and (5) are rewritten as equations (8) and (9), equations (6) and (7) are rewritten as equations (10) and (11), respectively. Note that the following relationships in equation (12) are used for the conversion. In equation (8), $T_{ji}$ represents the Cauchy stress tensor component.

$$\rho\left.\frac{\partial v_i}{\partial t}\right|_\chi + \rho c_j\frac{\partial v_i}{\partial x_j} = \frac{\partial T_{ji}}{\partial x_j} + \rho g_j \quad (8)$$

$$\left.\frac{\partial \rho}{\partial t}\right|_\chi + c_i\frac{\partial \rho}{\partial x_i} + \rho\frac{\partial v_i}{\partial x_i} = 0 \quad (9)$$

$$\int_{\Omega^K} \delta(x - x_A)\left(\left.\frac{\partial \rho}{\partial t}\right|_x + c_i\frac{\partial \rho}{\partial x_i} + \rho\frac{\partial v_i}{\partial x_i}\right)d\Omega^K = 0 \quad (10)$$

$$K = 1, 2$$

$$n^C \cdot (v_F(x) - v_S(X(x))) = 0 \text{ on } \Gamma^c \quad (11)$$

$$\chi = x, \hat{v}_i = 0, v_i = w_i, c_i = v_i - \hat{v}_i = w_j \frac{\partial x_i}{\partial \chi_j} = w_i \quad (12)$$

In contrast, the motion equation of a heart muscle is expressed as the following equation by using the Lagrangian coordinate system.

$$\rho_0 \left.\frac{\partial v}{\partial t}\right|_\chi = \nabla_\chi \cdot \Pi + \rho_0 \tilde{g} \quad (13)$$

Next, regarding the constitutive equation of the material, the blood is expressed by the following equation as incompressible Newton fluid, wherein μ represents a viscosity coefficient.

$$T = -pI + 2\mu D \quad (14)$$

$$D = \tfrac{1}{2}(\nabla_x \otimes v + v \otimes \nabla_x) \quad (15)$$

$$\nabla_x \cdot v = 0 \quad (16)$$

Thus, the first and second terms of the law of conservation of mass are eliminated. In addition, if the tangent stiffness of the constitutive equation of the heart muscle described in the Lagrange coordinate system is represented by a fourth-order tensor C, the following equations are established. In the following equations, S represents the 2nd Piola-Kirchhoff stress, F represents the deformation gradient tensor, and E represents the Green-Lagrange strain tensor.

$$\Pi = S \cdot F^T \quad (17)$$

$$F = x \otimes \nabla_x \quad (18)$$

$$\Pi = (\det F) F^{-1} \cdot T \quad (19)$$

$$S = C:E \quad (20)$$

$$E = \tfrac{1}{2}\{\nabla_x \otimes u + u \otimes \nabla_x + (\nabla_x \otimes u) \cdot (u \otimes \nabla_x)\} \quad (21)$$

Thus, first, by displaying a variational form equation of the Navier-Stokes equation of the blood observed based on the ALE coordinate system in the Euler coordinate system, equation (22) is derived. Next, a variational form equation of the motion equation of the heart wall is derived as equation (23). In addition, by applying the divergence theorem to constraint condition equations (24) and (25) between the blood and the valve, equation (26) is derived. Consequently, the stationary condition equation of the entire system is expressed as equation (27).

$$\delta W_f^{ALE} \equiv \int_{\Omega^f} \delta v \cdot \rho^f \left.\frac{\partial v}{\partial t}\right|_\chi d\Omega^f + \int_{\Omega^f} \delta v \cdot \rho^f (v \otimes \nabla_x) \cdot C d\Omega^f + \quad (22)$$

$$2\mu \int_{\Omega^f} \delta D : D d\Omega^f - \int_{\Omega^f} \rho^f \nabla_x \cdot \delta v d\Omega^S -$$

$$\int_{\Omega^f} \delta p (\nabla_x \cdot v) d\Omega^f - \int_{\Omega^f} \delta v \cdot \rho^f g d\Omega^f - \int_{\Gamma^f} \delta v \cdot \underline{\tau} d\Gamma^f$$

$$\delta W_S = \quad (23)$$

$$\int_{\Omega^S} \delta \dot{u} \cdot \rho^S \ddot{u} d\Omega^S + \int_{\Omega^S} \delta E : S d\Omega^S - \int_{\Omega^S} \delta u \cdot \rho^S g d\Omega^S - \int_{\Gamma^S} \delta u \cdot \underline{\tau} d\Gamma^S$$

$$\int_{\Omega^K} \delta(x - x_A) \nabla_x \cdot v d\Omega^K = 0, K = 1, 2 \quad (24)$$

$$n^C \cdot (v - \dot{u}) = 0 \text{ on } \Gamma^c \quad (25)$$

$$\sum_{K=1}^{2} (-1)^K \frac{1}{2} \int_{\Omega^f} \nabla \otimes \delta(x - x_A) \cdot v(x) d\Omega^K + \quad (26)$$

$$\int_{\Gamma^c} \delta(x - x_A) n^C \cdot \dot{u}(x_A) d\Gamma^C \equiv C(x;v,\dot{u})$$

$$\delta W^{total} \equiv \delta W_f^{ALE} + \delta W_S^1 + \delta W_S^2 + \int_{\Gamma^c} \lambda(x) C(x;\delta v, \delta \dot{u}) d\Gamma^C + \quad (27)$$

$$\int_{\Gamma^c} \delta \lambda(x) C(x;v,\dot{u}) d\Gamma^C - \int_{\Gamma^c} \varepsilon_\lambda \delta \lambda(x) \lambda(x) d\Gamma^C = 0$$

In the middle side of equation (27), $\delta W_S^1$ and $\delta W_S^2$ represent the first variations of the entire potential regarding the heart muscle and an individual valve. The last term in the middle side is a stabilization term.

In addition, connection between a heart valve and a wall, interaction made by contact between heart valves or between a heart valve and a heart wall, and connection with the systemic circulation analogy circuit can also be performed by using the Lagrange multiplier method. In this case, the stationary condition equation of the entire system is expressed as equation (28).

$$\delta W^{total} \equiv \delta W_f^{ALE} + \delta W_S^1 + \delta W_S^2 + \int_{\Gamma^c} \lambda(x) C(x;\delta v, \delta \dot{u}) d\Gamma^C + \quad (28)$$

$$\int_{\Gamma^c} \delta \lambda(x) C(x;v,\dot{u}) d\Gamma^C - \int_{\Gamma^c} \varepsilon_\lambda \delta \lambda(x) \lambda(x) d\Gamma^C +$$

$$\int_{\Gamma_L} \tau(x) \cdot (\delta x_L - W_L^W \delta x_W) dl + \int_{\Gamma_L} \delta \tau(x) \cdot (x_L - W_L^W x_W) dl -$$

$$\int_{\Gamma_R} \varepsilon_\tau \delta \tau(x) \cdot \tau(x) dl + \sum_{i,j} \int_{\Gamma_{T,i}} \eta_{ij}(x_i) \delta C_t(x_i;u_f, u_j) ds_i +$$

$$\sum_{i,j} \int_{\Gamma_{T,i}} \delta \eta_{ij}(x_i) C_t(x_i;u_i, u_j) ds_i - \sum_{i,j} \int_{\Gamma_{T,i}} \varepsilon_\eta \delta \eta_{ij}(x_i) \eta_{ij}(x_i) ds +$$

$$\int_{\Gamma_{f,k}} P_k n_k \cdot \delta v ds_k + \int_{\Gamma_{f,k}} \delta P_k (n_k \cdot v - F_k) ds_k = 0$$

$\Gamma_L$ represents a connection interface between a heart valve and a myocardial wall, $\chi_L$, and $\chi_W$ represent node coordinates of a heart valve and a myocardial wall, $W_R^W$ represents an interpolation coefficient from a myocardial wall node to a connection point, $\Gamma_{T,i}$ represents a surface that could be brought into contact, and $C_t$ is a contact condition equation. In addition, $\Gamma_{f,k}$ represents a blood domain interface connected to the systemic circulation analogy circuit, $F_k$ represents a flow volume to the systemic circulation model on a connection surface. In addition, $P_k$ represents the blood pressure of the systemic circulation model on a connection surface, and $v_k$ and $Q_k$ represent the blood pressure variable and the capacity variable in the systemic circulation model, respectively. With these parameters, the equation is solved as a system including the next balance equation of the systemic circulation analogy circuit.

$$G_k(P_k, F_k, V_k, Q_k) = 0 \quad (29)$$

Figure 14:
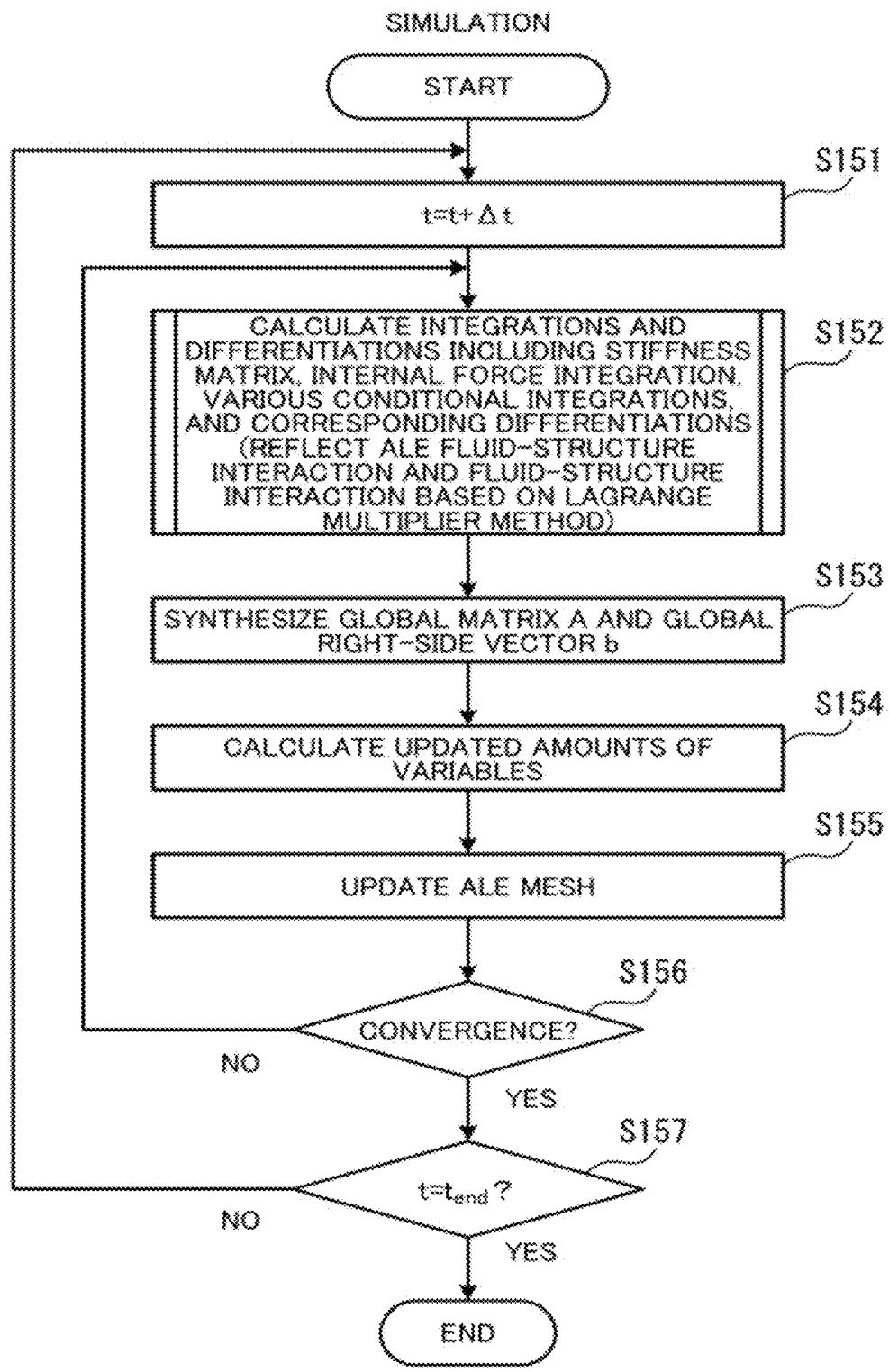
FIG. 14 is a flowchart illustrating an example of a procedure of the simulation.

The following description will be made on a prognosis prediction system that predicts prognosis by performing finite element discretization and a heart simulation on the basis of the above formulation. A calculation procedure of the simulation will be described in detail with reference to a flowchart (FIG. 14).

Figure 7:
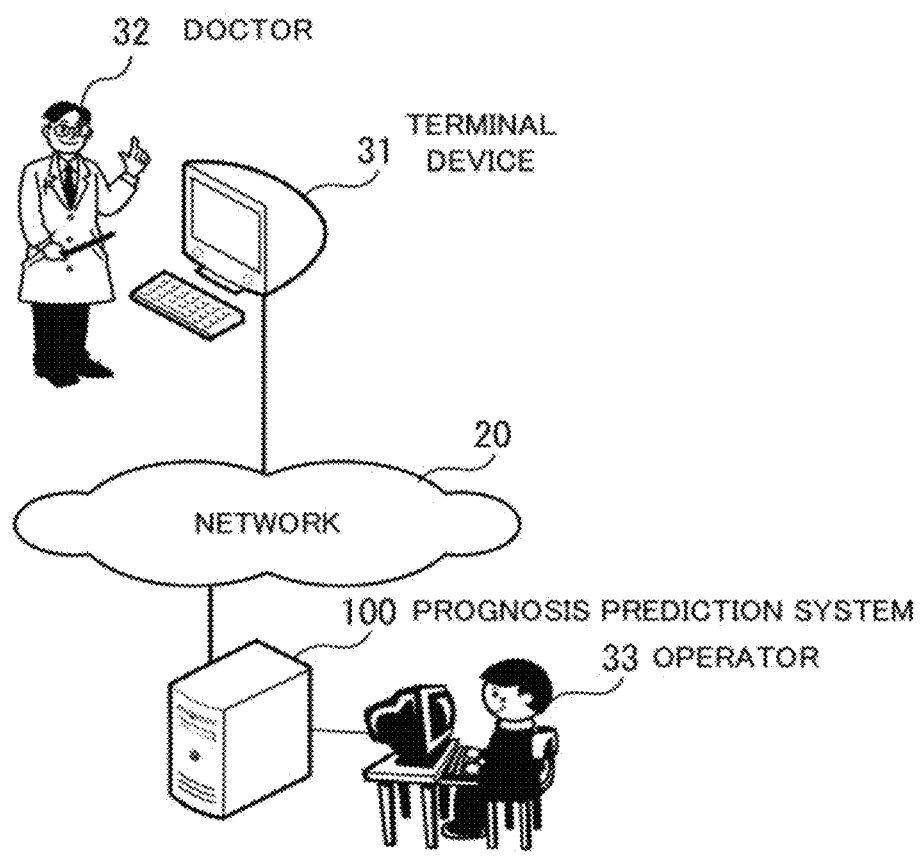
FIG. 7 illustrates an example of a system configuration according to a second embodiment.

FIG. 7 illustrates an example of a system configuration according to the second embodiment. A terminal device 31 operated by a doctor 32 is connected to a prognosis prediction system 100 via a network 20. Information inputted by the doctor 32 to the terminal device 31 is transmitted from the terminal device 31 to the prognosis prediction system 100 via the network 20. For example, the content of a treatment performed on a biological body is transmitted from the terminal device 31 to the prognosis prediction system 100. The prognosis prediction system 100 performs pre-processing, a simulation, and post-processing on the basis of the information transmitted from the terminal device 31 or information inputted by an operator 33 that operates the prognosis prediction system 100.

For example, the prognosis prediction system according to the second embodiment may be realized by using a computer having a processor and a memory.

Figure 8:
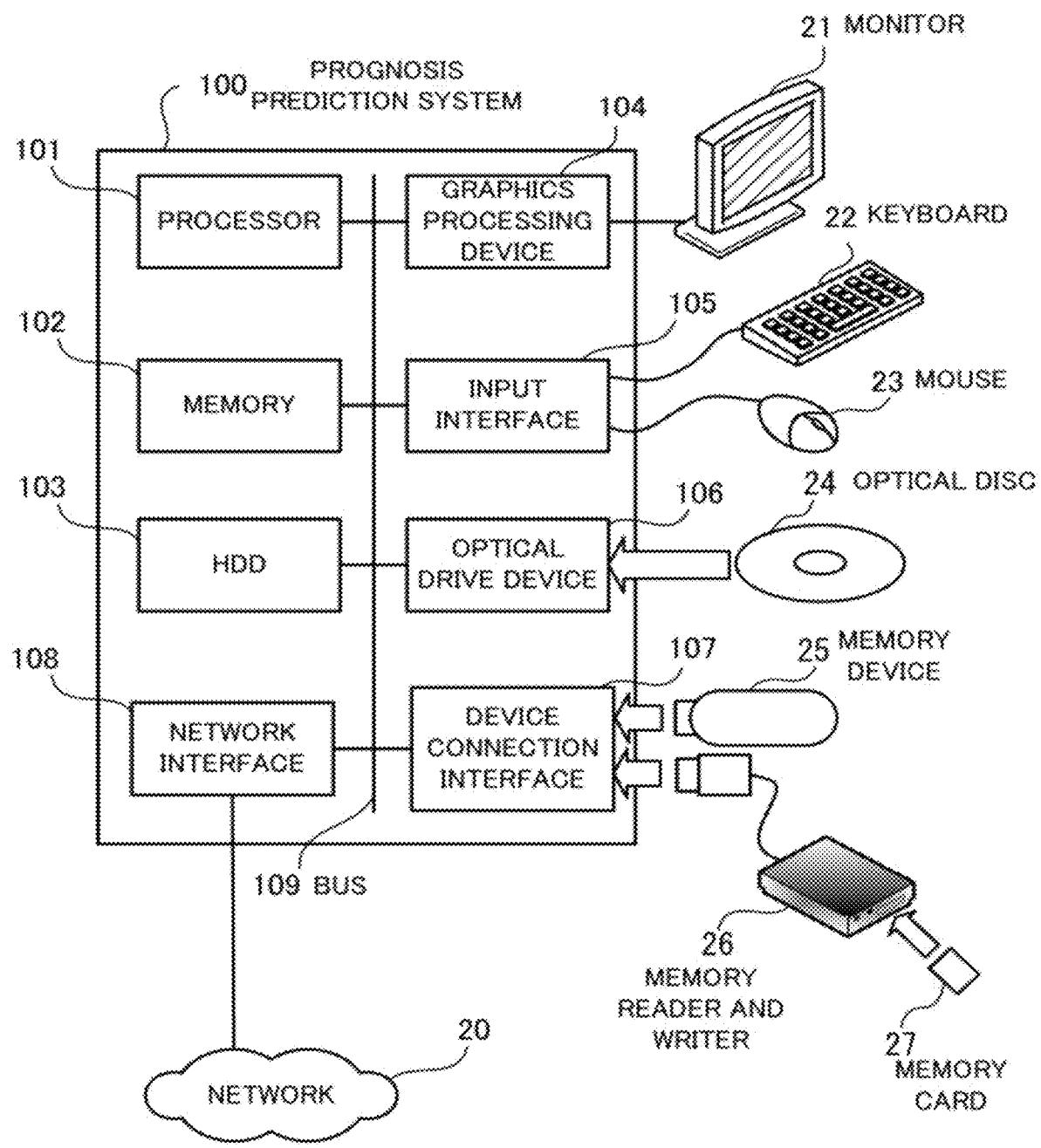
FIG. 8 illustrates an example of a hardware configuration of a prognosis prediction system according to the second embodiment.

FIG. 8 illustrates an example of a hardware configuration of the prognosis prediction system according to the second embodiment. The prognosis prediction system 100 is comprehensively controlled by a processor 101. The processor 101 is connected to a memory 102 and a plurality of peripheral devices via a bus 109. The processor 101 may be a multiprocessor. Examples of the processor 101 include a CPU (Central Processing Unit), an MPU (Micro Processing Unit), and a DSP (Digital Signal Processor). At least a part of the functions realized by causing the processor 101 to perform a program may be realized by using an electronic circuit such as an ASIC (Application Specific Integrated Circuit) or a PLD (Programmable Logic Device).

The memory 102 is used as a main storage device of the prognosis prediction system 100. The memory 102 temporarily holds at least a part of a program of an OS (Operating System) or an application program executed by the processor 101. In addition, the memory 102 holds various types of data needed in processing performed by the processor 101. For example, a volatile semiconductor memory device such as a RAM (Random Access Memory) is used as the memory 102.

Examples of the peripheral devices connected to the bus 109 include an HDD (Hard Disk Drive) 103, a graphics processing device 104, an input interface 105, an optical drive device 106, a device connection interface 107, and a network interface 108.

The HDD 103 magnetically writes and reads data on its internal disk. The HDD 103 is used as an auxiliary storage device of the prognosis prediction system 100. The HDD 103 holds an OS program, an application program, and various kinds of data. A non-volatile semiconductor memory device such as a flash memory may be used as the auxiliary storage device.

The graphics processing device 104 is connected to a monitor 21. The graphics processing device 104 displays an image on a screen of the monitor 21 in accordance with an instruction from the processor 101. Examples of the monitor 21 include a CRT (Cathode Ray Tube) display device and a liquid crystal display device.

The input interface 105 is connected to a keyboard 22 and a mouse 23. The input interface 105 transmits a signal transmitted from the keyboard 22 or the mouse 23 to the processor 101. The mouse 23 is an example of a pointing device. A different pointing device such as a touch panel, a tablet, a touchpad, or a trackball may also be used.

The optical drive device 106 reads data recorded on an optical disc 24 by using laser light or the like. The optical disc 24 is a portable recording medium holding data that can be read by light reflection. Examples of the optical disc 24 include a DVD (Digital Versatile Disc), a DVD-RAM, a CD-ROM (Compact Disc Read Only Memory), and a CD-R (Recordable)/RW (ReWritable).

The device connection interface 107 is a communication interface for connecting peripheral devices to the prognosis prediction system 100. For example, a memory device 25, a memory reader and writer 26, etc. can be connected to the device connection interface 107. The memory device 25 is a recording medium having a function of communicating with the device connection interface 107. The memory reader and writer 26 is a device that reads and writes data on a memory card 27. The memory card 27 is a card-type recording medium.

The network interface 108 is connected to the network 20. The network interface 108 exchanges data with other computers or communication devices via the network 20.

The prognosis prediction system 100 according to the second embodiment can be realized by the above hardware configuration. The terminal device 31 may be realized by a hardware configuration equivalent to that of the prognosis prediction system 100. In addition, the biological simulation apparatus 10 according to the first embodiment may be realized by a hardware configuration equivalent to that of the prognosis prediction system 100 illustrated in FIG. 8.

The prognosis prediction system 100 realizes a processing function according to the second embodiment by performing a program recorded on a computer-readable recording medium, for example. The program holding the processing content executed by the prognosis prediction system 100 may be recorded on any one of various kinds of recording medium. For example, the program executed by the prognosis prediction system 100 may be stored in the HDD 103. The processor 101 loads at least a part of the program in the HDD 103 onto the memory 102 and executes the loaded program. In addition, the program executed by the prognosis prediction system 100 may be recorded on a portable recording medium such as the optical disc 24, the memory device 25, or the memory card 27. For example, after the program stored in the portable recording medium is installed in the HDD 103, the program can be executed in accordance with an instruction from the processor 101. The processor 101 may directly read the program from the portable recording medium and execute the read program.

The prognosis prediction system 100 may be a parallel computer system in which a plurality of calculation devices having the hardware configuration illustrated in FIG. 8 are connected to each other via a high-speed transfer network and a plurality of calculation devices are operated in a parallel manner. In addition, the prognosis prediction system 100 may be a shared-memory calculation device having a large-scale memory. In addition, the prognosis prediction system 100 may include a front-end server separately from a calculation device that performs simulation operations, etc. In this case, by causing the front-end server to input a job to the calculation device, the simulation processing, etc. are executed on the calculation device. A job can be inputted via the network 20, for example.

Next, functions of the prognosis prediction system 100 that performs an accurate simulation on a heart including valves and that predicts postoperative conditions of the heart will be described.

Figure 9:
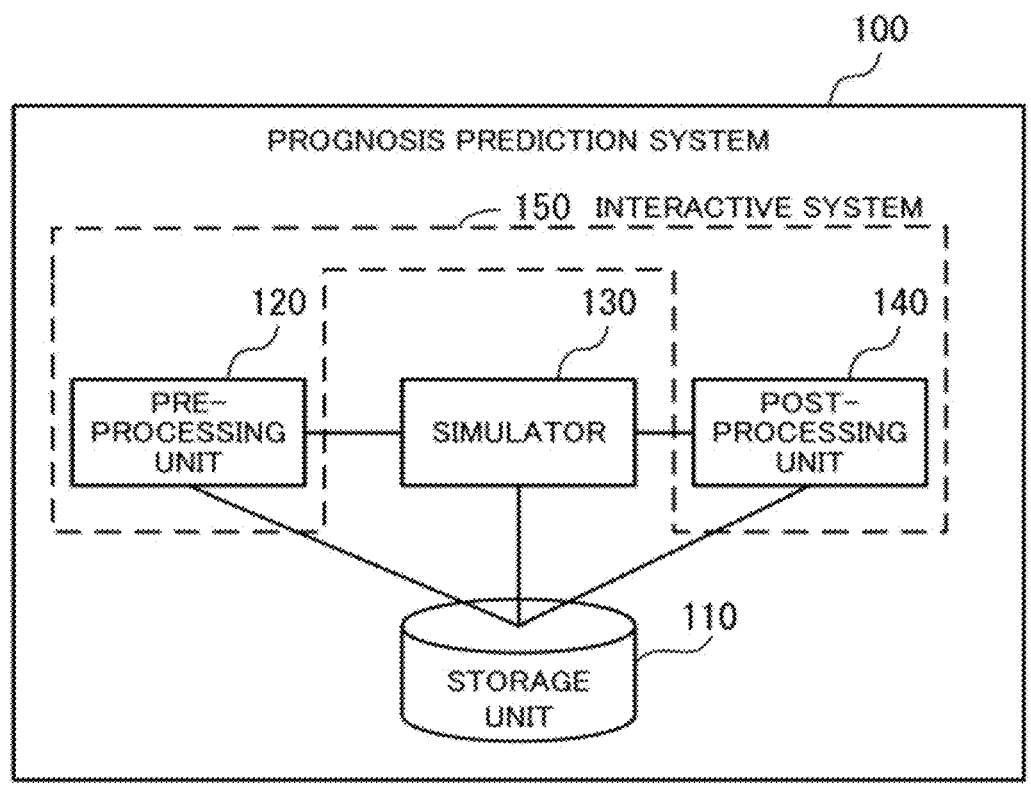
FIG. 9 is a block diagram illustrating functions of the prognosis prediction system.

FIG. 9 is a block diagram illustrating functions of the prognosis prediction system. The prognosis prediction system 100 includes a storage unit 110, a pre-processing unit 120, a simulator 130, and a post-processing unit 140.

The storage unit 110 holds a biological organ's geometric model and biological data. A geometric model is numerical data with which a 3D shape of a biological organ whose dynamics are to be predicted and a 3D shape of an immediate biological organ can be expressed through visualization or the like by using biological data. For example, when the shape of a biological organ is approximated by a biological model, a curved surface of the biological organ being approximated by a group of fine triangles, the 3D shape of the biological organ is expressed by the coordinates of the corners of the triangles. The biological data includes image data representing the 3D shapes of the target biological organ and the immediate biological organ. The image data is, for example, image data with which the shape of a biological organ can be identified two or three dimensionally, such as a CT (Computed Tomography) image, an MRI (Magnetic Resonance Imaging) image, or an echocardiogram of a biological organ or an immediate biological organ thereof. Information about temporal change is attached to part of the data. Other examples of the biological data include data about indices representing biological conditions, such as test data based on a cardiovascular catheterization test, an electrocardiogram, blood pressure, etc. and numerical data based on laboratory test values, other physiological tests, data based on an imaging test, a medical history of the patient including a history of operations and records of past operations, and knowledge of the doctor.

The storage unit 110 also holds finite element mesh models generated by the pre-processing unit 120. These finite element mesh models represent a biological heart on which a treatment has been performed. For example, when the biological organ is a heart, the finite element mesh models are tetra mesh models of the heart and the luminal blood, triangle mesh models of the heart valves, voxel mesh models of the heart and the luminal blood, and a voxel mesh model of the torso. For example, at least a part of the storage area of the memory 102 or the HDD 103 is used as the storage unit 110. The storage unit 110 may be arranged in an external storage device connected to the prognosis prediction system 100 via the network 20.

To reproduce a biological heart through a simulation, the pre-processing unit 120 extracts the shapes of the heart, immediate organs, and bones from the corresponding biological data and generates finite element mesh models of the heart and a finite element mesh model of the trunk from the extracted data. In addition, on the basis of the finite element mesh models representing the biological heart, the pre-processing unit 120 generates finite element mesh models of a postoperative heart obtained after a treatment presumed by the doctor is applied to the biological heart. For example, the finite element mesh models are generated on the basis of information interactively inputted by the doctor using the terminal device 31 or the like.

The simulator 130 performs an electrical excitation propagation simulation and a mechanical pulsation simulation in coordination with each other. In the mechanical pulsation simulation, the simulator 130 performs an accurate fluid-structure interaction simulation of a heart, including its valves. When performing the mechanical pulsation simulation, the simulator 130 captures the cusp interface of a heart valve from an interface-tracking ALE mesh that motions and deforms in conformity with an interface of the heart wall, to analyze the blood inside the heart wall. The operation screen of the simulator 130 may be displayed on the monitor 21 or the terminal device 31. In addition, information may be inputted to the simulator 130 by using an input device of the prognosis prediction system 100 such as the keyboard 22 or the terminal device 31.

The post-processing unit 140 analyzes and ranks simulation results on the basis of the evaluation values that the clinician considers important. For example, the post-processing unit 140 quickly and elaborately displays 3D images or moving images of numerical data about preoperative and postoperative conditions or a plurality of postoperative conditions obtained by a simulation. The post-processing unit 140 also analyzes data that can be compared and evaluated. The operation screen of the post-processing unit 140 may be displayed on the monitor 21 or the terminal device 31. In addition, information may be inputted to the post-processing unit 140 by using an input device of the prognosis prediction system 100 such as the keyboard 22 or the terminal device 31.

Among the elements illustrated in FIG. 9, an interactive system 150 is provided by the pre-processing unit 120 and the post-processing unit 140. Namely, the pre-processing unit 120 and the post-processing unit 140 perform processing in accordance with instructions made interactively by the doctor 32 and the operator 33.

Next, a procedure of prognosis prediction processing will be described.

Figure 10:
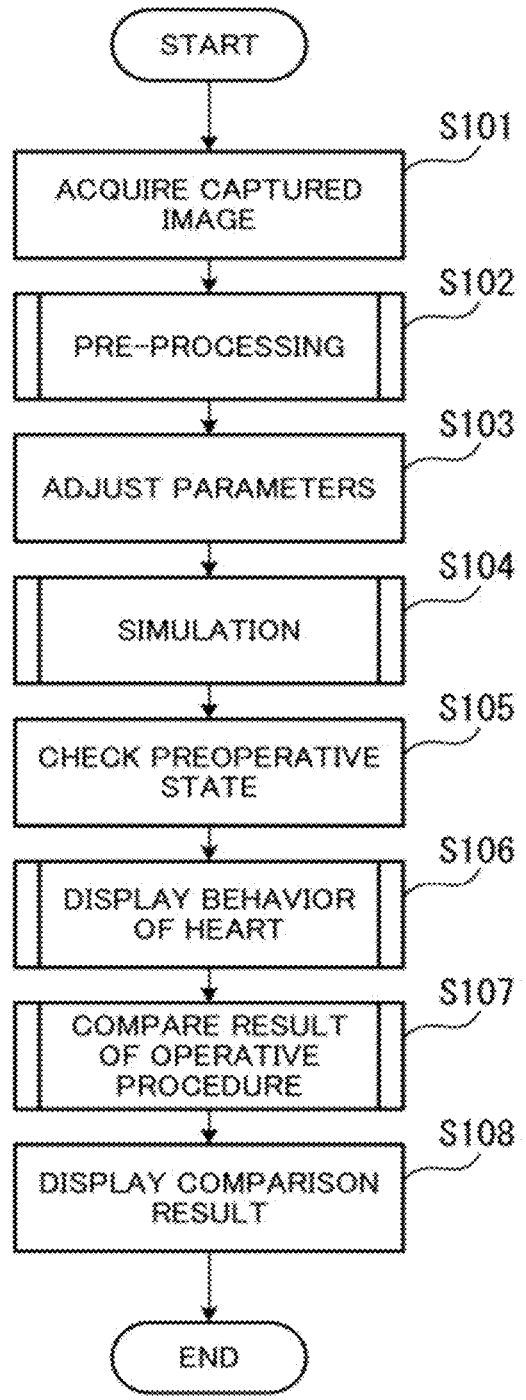
FIG. 10 is a flowchart illustrating an example of a procedure of prognosis prediction processing.

FIG. 10 is a flowchart illustrating an example of a procedure of prognosis prediction processing.

[Step S101] The pre-processing unit 120 acquires a captured image from the storage unit 110. For example, the pre-processing unit 120 acquires a CT image or an MRI image of a biological body.

[Step S102] The pre-processing unit 120 performs pre-processing. In the pre-processing, the pre-processing unit 120 performs shape extraction from biological data, creation of a geometric model of a biological organ, and generation of finite element mesh models of a heart having biologically geometric features. The pre-processing will be described in detail below (see FIGS. 11 to 13).

In this step, the pre-processing unit 120 can also create finite element mesh models representing a postoperative heart obtained by assuming that an operation has been performed by a doctor, in addition of the finite element mesh models representing the current conditions of the heart of the biological body. If there are a plurality of possible treatments, the pre-processing unit 120 can create finite element mesh models representing a postoperative heart per treatment.

[Step S103] The pre-processing unit 120 adjusts parameters used in the simulation. For example, the pre-processing unit 120 adjusts parameters so that simulation results based on the finite element mesh models approximate the corresponding biological data (an electrocardiogram, blood pressure, echo/MRI data, catheter test data, etc.). For example, the parameters are adjusted on the basis of information inputted by the doctor in view of the past simulation results.

[Step S104] The simulator 130 performs an accurate fluid-structure interaction simulation of the heart including its valves, by using the created finite element mesh models and the set parameters. When the finite element mesh models representing the preoperative and postoperative conditions are created, the simulator 130 performs a simulation for each of the created finite element mesh models. The simulation processing will be described in detail below (see FIGS. 14 and 15).

[Step S105] The post-processing unit 140 performs processing for checking the preoperative conditions. For example, the post-processing unit 140 compares a simulation result obtained by using the finite element mesh models representing the current conditions of the heart of the biological body with data about the current conditions of the biological body and displays the comparison result. If the simulation result does not match the current conditions of the biological body, resetting of parameters is performed, for example, in accordance with an instruction from the doctor.

[Step S106] The post-processing unit 140 displays the behavior of the heart obtained as the simulation result. For example, the post-processing unit 140 reproduces the behavior of the heart as an animation on the basis of the simulation result. The visualization processing for displaying the behavior will be described in detail below (see FIG. 21).

[Step S107] The post-processing unit 140 compares results per operative procedure. For example, by using data about the biological conditions, the post-processing unit 140 evaluates postoperative conditions in view of predetermined criteria. The comparison processing will be described in detail below (see FIG. 23).

[Step S108] The post-processing unit 140 displays the comparison result.

In this way, the prognosis prediction processing is performed. Next, each of the steps illustrated in FIG. 10 will be described in detail.

First, in accordance with an instruction inputted by a doctor who sufficiently understands the clinical conditions of the biological body, the pre-processing unit 120 segments the heart and large blood vessel domains on the basis of the biological data. In this step, the pre-processing unit 120 can reflect a medical history, a history of operations, records of past operations of the patient, including test data based on an echocardiogram, catheterization test, etc., and knowledge of the doctor on the segmentation. The pre-processing unit 120 generates a surface mesh, formed by triangles, from the segment data and segments the surface mesh into finer sites. For example, in the case of a left ventricle, the pre-processing unit 120 segments the surface mesh into domains corresponding to a left ventricle fluid domain, a myocardial domain, a papillary muscle, an aortic valve, and a mitral valve. Next, the pre-processing unit 120 generates two kinds of volume mesh (tetra and voxel) by using the surface meshes as boundaries. The tetra mesh model includes a triangle surface mesh that has a material number set per detailed site information and a tetra volume mesh that has a material number different per domain spatially segmented by the surfaces of the triangle surface mesh. The voxel mesh model includes structured grid data having a material number indicating domain information per voxel.

Next, the pre-processing unit 120 generates a torso (trunk of the body) voxel mesh model having domains segmented in accordance with the electric conductivity of the human body. Next, the pre-processing unit 120 refers to the biological data obtained from CT, MRI, etc. and segments organ and bone domains into domains in accordance with luminance values. In this operation, in the range from the shoulders to the lower back, the pre-processing unit 120 suitably compensates for domains lacking sufficient images. Next, the pre-processing unit 120 sets predetermined material numbers to the segmented domains and adjusts the position of the torso voxel mesh model with the position of a heart voxel mesh. Finally, the pre-processing unit 120 performs voxel resampling to match the heart voxel mesh.

By performing the above processing, finite element mesh models are generated. For example, finite element mesh models segmented per site are created.

The finite element mesh models created in this way are largely classified into two kinds, namely, torso and heart voxel mesh models and a heart tetra mesh model (including the tetra mesh models of the heart wall and the luminal blood). First, the pre-processing unit 120 creates a heart voxel mesh model by matching the torso voxel mesh with the heart tetra mesh model. In this way, tetra and voxel meshes are associated with each other. Next, the pre-processing unit 120 sets a fiber distribution and a sheet distribution to the heart voxel mesh model on the basis of literature values or the like. In addition, the pre-processing unit 120 sets a Purkinje fiber distribution or an equivalent endocardial conductance distribution. In addition, the pre-processing unit 120 sets a site of earliest activation to the endocardium. In addition, the pre-processing unit 120 distributes cell models having three kinds of APD (Action Potential Duration) distribution in the long axis direction and the short axis direction. For example, a method in "Computational fluid dynamics modeling of intracranial aneurysms: effects of parent artery segmentation on intra-aneurysmal hemodynamics" by M. A. Castro et al. is used for these settings. The simulator 130 performs an electrical excitation propagation simulation by combining the above heart voxel mesh model and a torso model having a body surface on which electrodes for a standard 12-lead electrocardiogram are set. The pre-processing unit 120 adjusts parameters so that the simulation result matches the result of the standard 12-lead electrocardiogram test on the biological body. Consequently, the time history of the calcium ion concentration (calcium concentration history) of an individual tetra element constituting the heart (an individual element of the heart tetra mesh model) is determined.

Next, the pre-processing unit 120 sets a fiber distribution and a sheet distribution to the heart tetra mesh model, as is the case with the voxel mesh model. In addition, the pre-processing unit 120 sets boundary conditions for performing a mechanical simulation. In addition, the pre-processing unit 120 performs duplexing of pressure nodes for mechanical analysis and duplexing of nodes at an interface between the blood and the heart muscle. In addition, the pre-processing unit 120 provides the heart tetra mesh model with site segmentation information. These finite element mesh models are created for a relaxation phase of the heart. Thus, to obtain a natural shape corresponding to a free-stress condition, the pre-processing unit 120 performs a suitable mechanical finite element method and contracts the heart. The pre-processing unit 120 connects a systemic circulation model matching the conditions of the biological body to the heart represented by the created finite element mesh model. This systemic circulation model is an electrical circuit analogy model formed by suitably combining discrete resistance and capacitance defined by assuming that the blood pressure is voltage and the blood flow is current.

The simulator 130 performs a pulsation simulation on the basis of the heart tetra mesh model to which the above systemic circulation model is connected and the contraction force obtained by using the calcium concentration history of an individual finite element for an excitation-contraction coupling model. After the simulation, the pre-processing unit 120 adjusts parameters so that the parameters match biological data such as a pressure-volume relationship, an MRI image, an echocardiographic image, etc. and mechanical indices extracted from these items of information. In addition, when the oxygen saturation has already been measured, the pre-processing unit 120 solves an advection diffusion equation using a fluid velocity distribution of the blood obtained through fluid-structure interaction analysis by using a finite element method using the same mesh as the mechanical mesh and checks the conformity.

After the simulation, the post-processing unit 140 performs visualization processing on the basis of files in which results of the electrical excitation propagation simulation and the mechanical pulsation simulation performed as described above are stored. For example, the post-processing unit 140 causes a visualization system to read more than 100 files including data of various phenomena such as excitation propagation and interaction between the heart muscle and the fluid per beat and to generate and visualize 3D shapes from numerical data. The post-processing unit 140 enables observation from various points of view by changing the viewpoint in accordance with input information. In addition, by generating cross sections, the post-processing unit 140 enables observation of any one of the cross sections. In addition, by quickly generating a moving image of the behavior of the atria and displaying the behavior as an animation, the post-processing unit 140 enables realistic observation. In addition, the post-processing unit 140 can also extract and display a part of the heart muscle so that change of the extracted part over time can be checked.

The doctor refers to the visualization result and gains a better understanding of the pump performance of the heart, the hemodynamics, the load on the heart and the lungs, etc. As a result, the doctor can make diagnostic or clinical decisions. For example, the pump performance of the heart represents the motion of the heart and the motions and functions of the heart valves. For example, the hemodynamics includes the pressure generated by the heart, the pressure at an individual cardiovascular site, the flow volume of the blood at an individual cardiovascular site, the velocity of the blood flow at an individual cardiovascular site, the oxygen saturation of the blood at an individual cardiovascular site, the dissolved gas partial pressure of the blood at an individual cardiovascular site, and the blood concentration of drug at an individual cardiovascular site. For example, the load on the heart and lungs includes the energy consumption amount of the heart, the energy conditions of the blood fluid, the pressure caused in the heart muscle, the conditions of the coronary artery circulation, the systemic vascular resistance, and the pulmonary vascular resistance.

While what has been described is a technique for reproducing and visualizing the heart of the current biological body, the prognosis prediction system 100 can also visualize a result obtained by virtually performing several treatments on a heart model.

Figure 11:
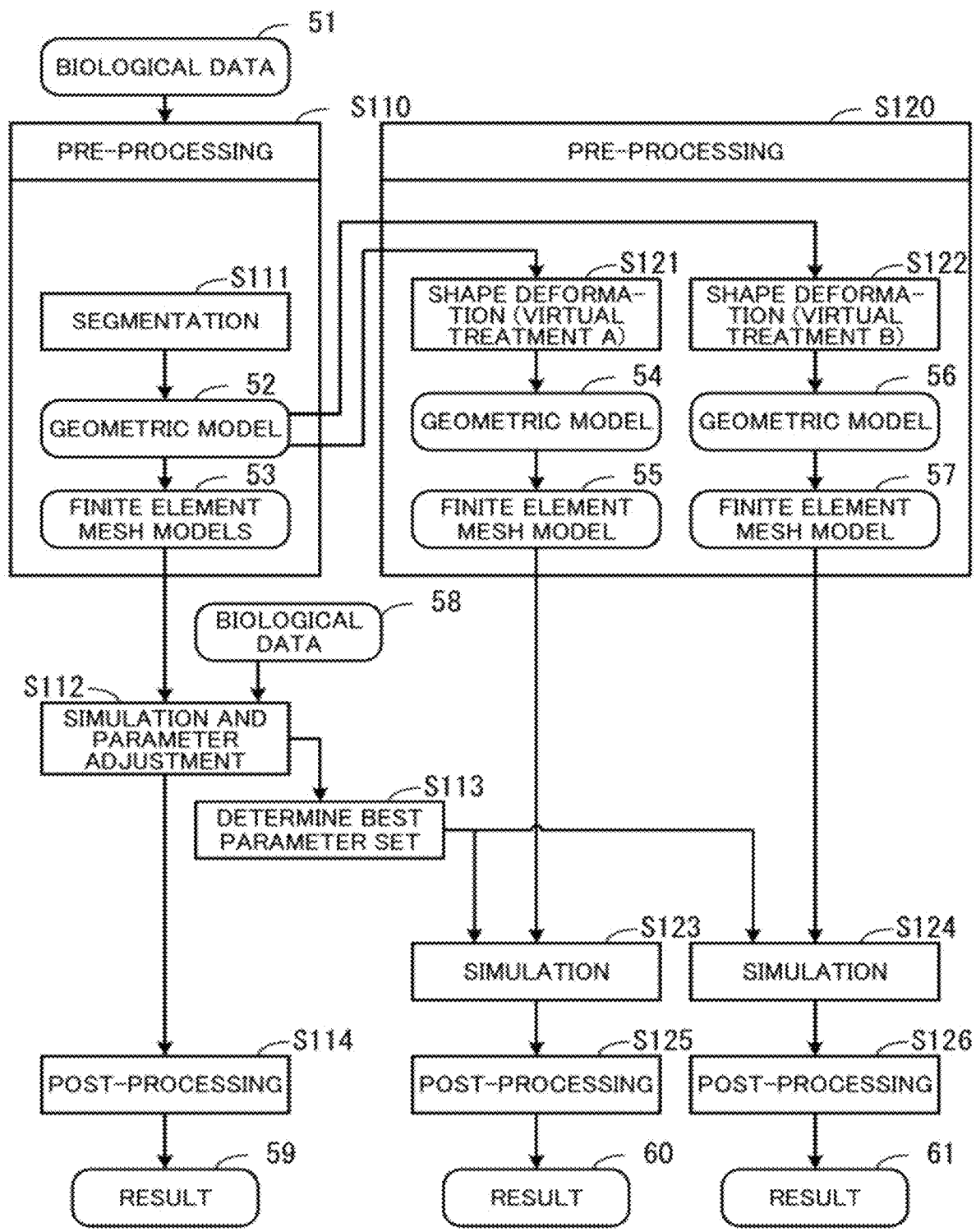
FIG. 11 illustrates a scheme for obtaining results of virtual treatments.

FIG. 11 illustrates a scheme for obtaining results of virtual treatments. First, on the basis of a biological data 51 (a CT image, an MRI image, an echocardiogram, etc.), the pre-processing unit 120 performs pre-processing (step S110) for generating heart mesh models obtained before a virtual operation is performed. In this pre-processing, the pre-processing unit 120 performs processing for segmentation (step S111) and so forth to create a geometric model 52 and finite element mesh models 53 of the heart of a biological body. The finite element mesh models 53 are models of the preoperative heart and chest of the biological body. The pre-processing for generating heart mesh models obtained before a virtual operation is performed will be described below in detail (see FIG. 12).

By using the finite element mesh models 53 created from the biological data 51, the pre-processing unit 120 performs a simulation and parameter adjustment (step S112). In the simulation and parameter adjustment, the pre-processing unit 120 repeats a simulation while changing parameters so that the finite element mesh models approximate the biological data 58 (an electrocardiogram, blood pressure, echo/MRI data, catheterization test data, etc.). In the simulation, the pre-processing unit 120 performs an electrical excitation propagation simulation first before a mechanical pulsation simulation. The pre-processing unit 120 performs the mechanical pulsation simulation in accordance with a simulation method of fluid-structure interaction in which the above heart tetra mesh model is represented as a structure mesh model representing the structure domain and the luminal blood tetra mesh model as an ALE fluid mesh model representing the fluid domain. The simulation processing and the parameter adjustment processing will be described in detail below (see FIG. 13). Next, a set of parameters (a best parameter set) with which the simulation result approximates the biological data the most is determined (step S113).

In addition, on the basis of the geometric model created in the pre-processing (step S110), the pre-processing unit 120 performs pre-processing (step S120) for generating heart mesh models in accordance with a virtual treatment. In this pre-processing (step S120), the pre-processing unit 120 performs shape deformation per virtual treatment (steps S121 and S122). For example, the pre-processing unit 120 performs shape deformation in accordance with a "virtual treatment A" to create a geometric model 54 and a finite element mesh model 55. In addition, the pre-processing unit 120 performs shape deformation in accordance with a "virtual treatment B" different from the "virtual treatment A" to create a geometric model 56 and a finite element mesh model 57. In addition, the simulator 130 performs simulations by using the best parameter set and the finite element mesh models 55 and 57 representing the conditions after the respective virtual treatments (steps S123 and S124).

The post-processing unit 140 performs post-processing (steps S114, S125, and S126) for converting each of the simulation results into data that can be visualized and generates results 59 to 61 that can be visualized. The results 59 to 61 are stored in a storage device such as a memory or an HDD. The result 59 obtained from a model representing the heart of the current biological body is used as a reference for diagnosis by the doctor, along with the biological data 51 and 58.

The doctor refers to the visualization results of these possible virtual operations and compares the results in terms of the pump performance of the postoperative heart, the hemodynamics, the load on the heart and the lungs, etc. Thus, the doctor can use these results as information for determining the most suitable operative procedure. By performing virtual operations and visualizing the results, for example, the doctor can predict the following contents.

For example, the doctor can predict conditions of a heart that has undergone an operation for congenital heart disease, conditions of a circulatory system that has undergone percutaneous coronary intervention or an aortocoronary bypass operation, conditions of a circulatory system that has undergone a heart valve replacement operation, conditions of a circulatory system that has undergone cardiac valvuloplasty, conditions of a circulatory system that has undergone cardiac valve annuloplasty, conditions of a circulatory system that has undergone pacemaker treatment including cardiac resynchronization treatment, conditions of a circulatory system that has undergone treatment for aortic disease, conditions of a circulatory system that has undergone treatment for pulmonary arteriopathy, conditions of a circulatory system that has undergone implantation of a circulatory assist device, and conditions of a circulatory system that has undergone other cardiovascular treatment. Examples of the operation for congenital heart disease include an open-heart operation for congenital heart disease, a catheterization operation for congenital heart disease, and an extracardiac operation for congenital heart disease. Examples of the catheterization operation for congenital heart disease include an operation using a defect closure device and an operation using a balloon catheter. Examples of the extracardiac operation for congenital heart disease include the Blalock-Taussig shunt, pulmonary artery banding, the Glenn operation, and TCPC (total cavopulmonary connection). The heart valve replacement operation and the cardiac valvuloplasty include a catheterization operation. Examples of the circulatory assist device include an intra-aortic balloon pump, a percutaneous cardiopulmonary support device, a left ventricular assist device, and a right ventricular assist device. The cardiovascular treatment includes medical treatment.

Next, the pre-processing (step S110) for generating heart mesh models obtained before a virtual operation will be described in more detail.

Figure 12:
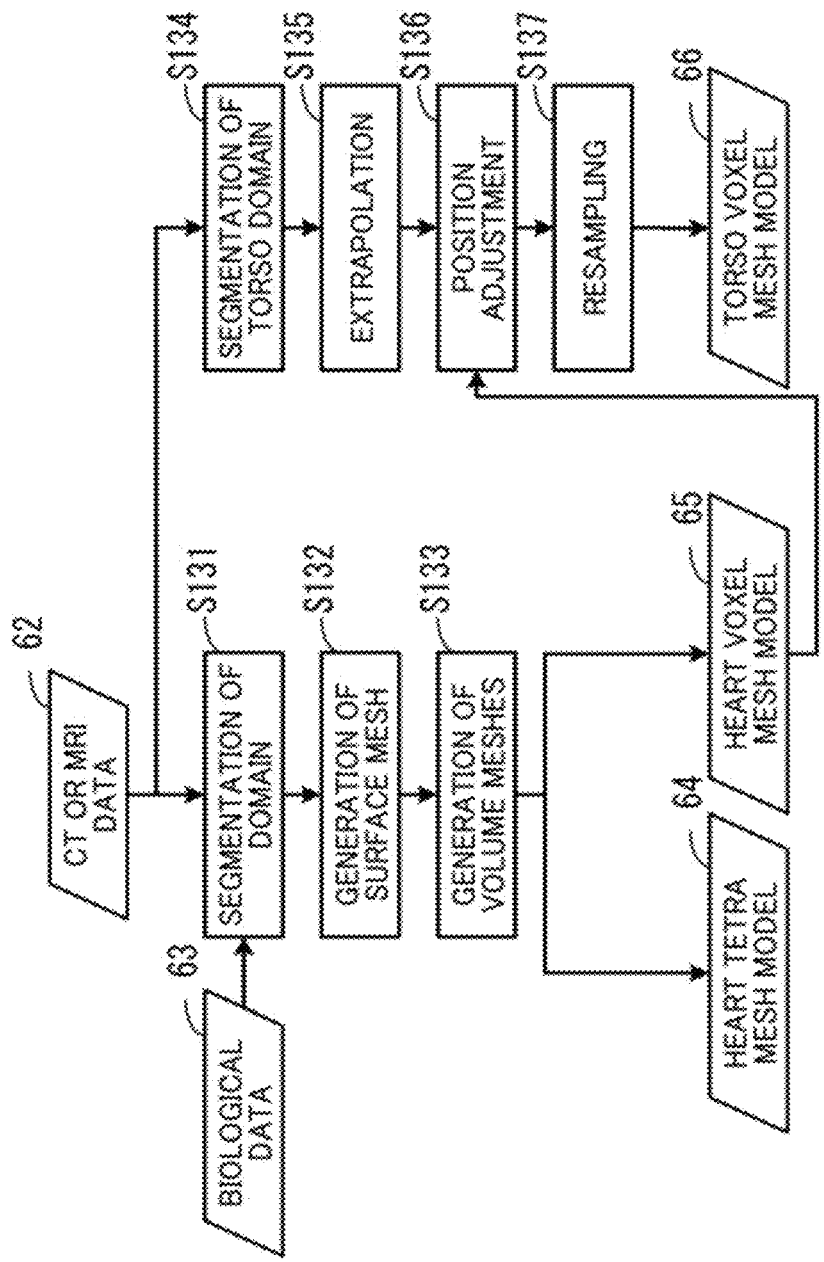
FIG. 12 illustrates an example of a procedure of generating heart mesh models obtained before a virtual operation.

FIG. 12 illustrates an example of a procedure of generating heart mesh models obtained before a virtual operation. The pre-processing unit 120 performs segmentation of the heart domain by using CT or MRI data and biological data 63 (step S131). Next, the pre-processing unit 120 generates a triangle surface mesh segmented per site (step S132). Next, the pre-processing unit 120 generates voxel and tetra volume meshes by using the surface mesh as boundaries (step S133). As a result, a heat tetra mesh model 64 and a heart voxel mesh model 65 are generated.

In addition, the pre-processing unit 120 performs segmentation of the torso domain to generate a voxel mesh model (step S134). In the segmentation of the torso domain, the lung, bone, and organ domains are segmented on the basis of the CT or MRI data 62. Next, the pre-processing unit 120 performs extrapolation processing for compensating for insufficient domains (step S135). After the extrapolation processing, the pre-processing unit 120 adjusts the position of the heart voxel model and the position of the torso voxel model (step S136). Next, the pre-processing unit 120 performs resampling for reestablishing the structured grid of the torso in conformity with the heart voxel mesh (step S137). In this way, a torso voxel mesh model 66 is generated.

The finite element mesh models 53 illustrated in FIG. 11 include the heart tetra mesh model 64, the heart voxel mesh model 65, and the torso voxel mesh model 66 illustrated in FIG. 12. On the basis of these finite element mesh models 53, the pre-processing unit 120 performs the simulation processing and the parameter adjustment processing.

Figure 13:
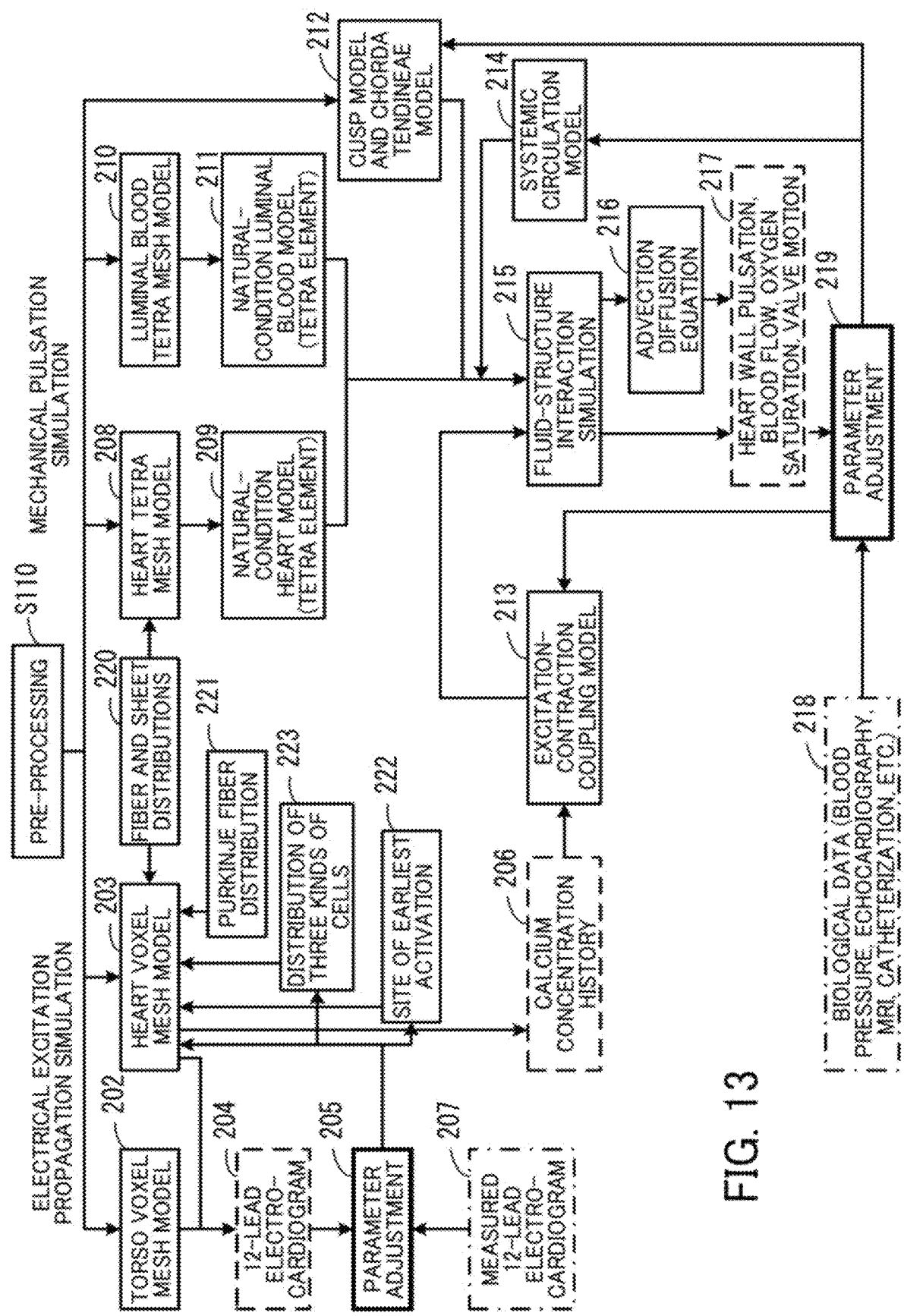
FIG. 13 illustrates simulation processing and parameter adjustment processing.

FIG. 13 illustrates the simulation processing and the parameter adjustment processing. In FIG. 13, each item of information outputted as a simulation result is surrounded by a dashed line, and biological data is surrounded by a dashed-dotted line. The parameter adjustment processing is surrounded by a thick line.

The simulation-purpose finite element mesh models 53 obtained in the pre-processing (step S110) are largely classified into two kinds, namely, models for an electrical excitation propagation simulation and models for a mechanical pulsation simulation. The former models are created by voxel finite elements and include a torso voxel mesh model 202 and a heart voxel mesh model 203 representing the heart in a relaxation phase. The pre-processing unit 120 sets fiber and sheet distributions 220 to the heart voxel mesh model 203 on the basis of literature values or the like. In addition, the pre-processing unit 120 sets a Purkinje fiber distribution 221 or an equivalent endocardial conductance distribution to the heart voxel mesh model 203. In addition, the pre-processing unit 120 sets a site of earliest activation 222 to the endocardium of the heart voxel mesh model 203. In addition, the pre-processing unit 120 distributes cell models having three kinds of APD distribution in the long axis direction and the short axis direction (distribution of three kinds of cells 223).

The simulator 130 performs an electrical excitation propagation simulation by combining the above heart voxel mesh model 203 and the torso voxel mesh model 202 having a body surface on which electrodes for an electrocardiogram are set. As a result, a 12-lead electrocardiogram 204 is obtained. Next, the pre-processing unit 120 performs parameter adjustment 205 so that the 12-lead electrocardiogram 204 obtained as a simulation result matches a measured 12-lead electrocardiogram 207. Consequently, a calcium concentration history 206 of an individual tetra element constituting the heart (an individual element of the heart tetra mesh model) is determined.

Next, the pre-processing unit 120 sets the fiber and sheet distributions 220 to a heart tetra mesh model 208. In addition, the pre-processing unit 120 sets boundary conditions for performing a mechanical simulation. In addition, the pre-processing unit 120 performs duplexing of pressure nodes for mechanical analysis and duplexing of nodes at an interface between the blood and the heart muscle. In addition, the pre-processing unit 120 provides the heart tetra mesh model 208 with site segmentation information.

In addition, the pre-processing unit 120 creates a luminal blood tetra mesh model 210 in a relaxation phase. The luminal blood tetra mesh model 210 is a tetra mesh model representing the shape of the domain in which blood inside the heart flows. The heart tetra mesh model 208 and the luminal blood tetra mesh model 210 are created for a relaxation phase of the heart. The pre-processing unit 120 creates a natural shape model corresponding to a free-stress condition from each of the heart tetra mesh model 208 and the luminal blood tetra mesh model 210. For example, the pre-processing unit 120 performs a suitable mechanical finite element method, contracts the heart, and creates a natural-condition heart model 209 and a natural-condition luminal blood model 211.

The pre-processing unit 120 adds, as simulation information, a combination 212 of cusp models of membrane elements and chorda tendineae models of beam elements to the natural-condition heart model 209 and the natural-condition luminal blood model 211. In addition, the pre-processing unit 120 connects a systemic circulation model 214 adjusted to the biological conditions. On the basis of the various models to which the systemic circulation model 214 has been connected and the contraction force obtained by using the calcium concentration history of an individual finite element for an excitation contraction coupling model 213, the simulator 130 analyzes the behavior of the pulsation and performs a fluid-structure interaction simulation 215. Next, the pre-processing unit 120 adjusts parameters so that the parameters match biological data 218 based on blood pressure, echocardiography, MRI, catheterization, etc. and mechanical indices extracted from the biological data 218. When the oxygen saturation has already been measured, the pre-processing unit 120 solves an advection diffusion equation 216 using a fluid velocity distribution of the blood obtained through a fluid-structure interaction simulation 215 by using a finite element method using the same mesh as the mechanical mesh and checks the conformity.

In this way, the simulation and the parameter adjustment are performed. In the simulation, fluid-structure interaction analysis in which the ALE method and the Lagrange multiplier method are combined with each other is used. The procedure of the fluid-structure interaction simulation performed by the simulator 130 is as follows.

FIG. 14 is a flowchart illustrating an example of a procedure of the simulation.

[Step S151] The simulator 130 updates time of the time step. For example, the simulator 130 adds a predetermined time increment Δt to the current time t. When the simulation is started, the time is set to t=0.

[Step S152] The simulator 130 calculates a stiffness matrix, internal force integration, and various conditional integrations and the corresponding differentiations. The matrix, differentiations, and integrations reflect the ALE fluid-structure interaction and fluid-structure interaction based on the Lagrange multiplier method.

[Step S153] The simulator 130 synthesizes a global matrix A and a global right-side vector b.

[Step S154] The simulator 130 calculates updated amounts of variables.

[Step S155] The simulator 130 updates the ALE mesh.

[Step S156] The simulator 130 determines whether the calculation result has converged. If so, the processing proceeds to step S157. If not, the processing returns to step S152 and the calculation processing is performed again.

[Step S157] The simulator 130 determines whether the simulation time t has reached finish time $t_{end}$. For example, the finish time $t_{end}$ is when a simulation of a single beat of the heart is finished. When the finish time $t_{end}$ has been reached, the simulator 130 ends the simulation. If the finish time $t_{end}$ has not been reached, the processing returns to step S151.

The processing in steps S152 to S155 will hereinafter be described in detail.

Figure 15:
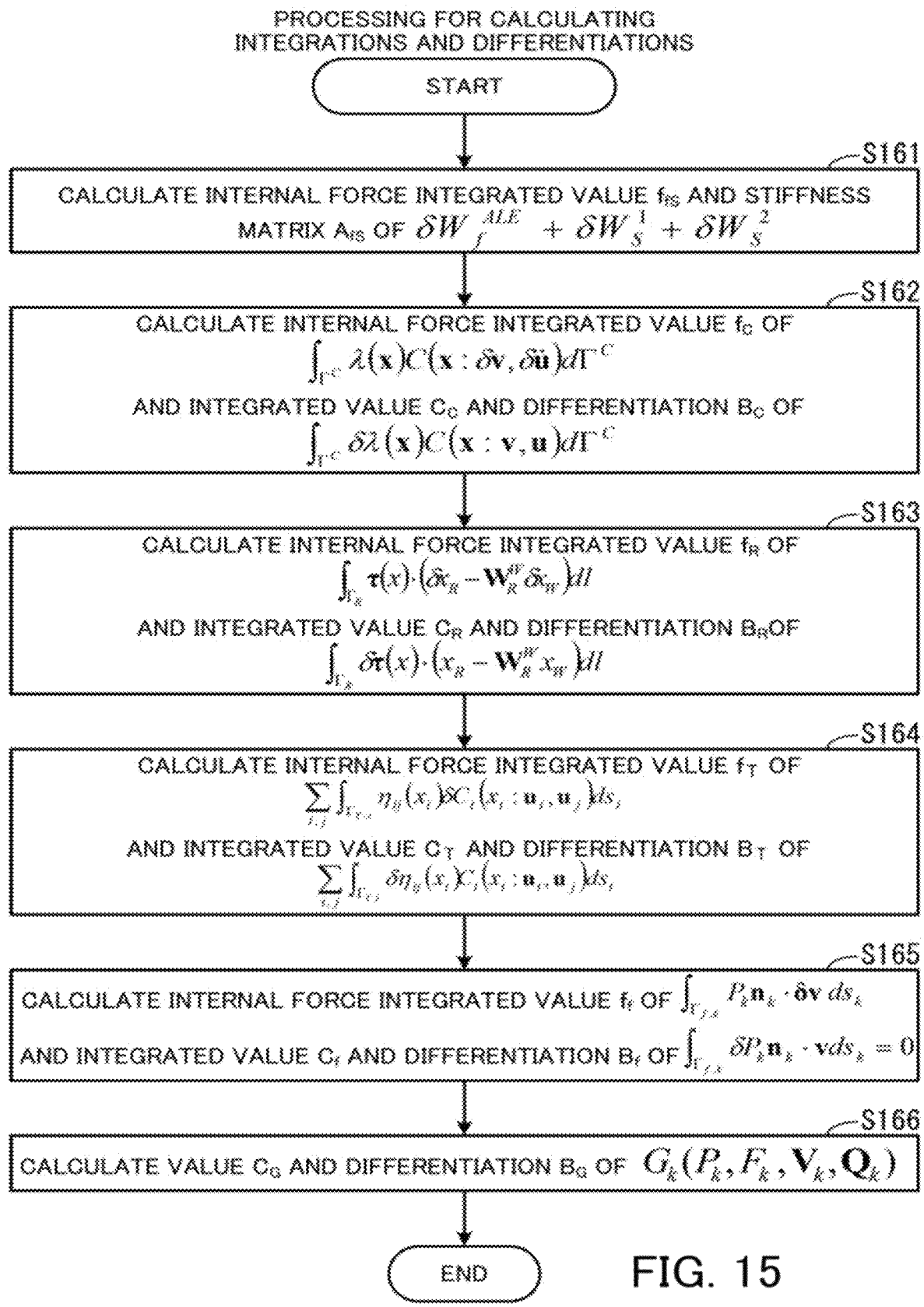
FIG. 15 is a flowchart illustrating an example of a procedure of differentiation and integration calculation processing.

FIG. 15 a flowchart illustrating an example of a procedure of the differentiation and integration calculation processing.

[Step S161] The simulator 130 calculates an internal force integrated value $f_{fs}$ and a stiffness matrix $A_{fs}$ of equation (30).

$$\delta W_f^{ALE} + \delta W_S^1 \delta W_S^2 \tag{30}$$

[Step S162] The simulator 130 calculates an internal force integrated value $f_C$ of equation (31) and an integrated value $C_C$ and differentiation $B_C$ of equation (32).

$$\int_{\Gamma^C} \lambda(x) C(x:\delta v, \delta \dot{u}) d\Gamma^C \tag{31}$$

$$\int_{\Gamma^C} \delta\lambda(x) C(x:v,u) d\Gamma^C \tag{32}$$

[Step S163] The simulator 130 calculates an internal force integrated value $f_R$ of equation (33) and an integrated value $C_R$ and differentiation $B_R$ of equation (34).

$$\int_{\Gamma_R} \tau(x) \cdot (\delta x_R - W_R{}^W \delta x_W) dl \tag{33}$$

$$\int_{\Gamma_R} \delta\tau(x) \cdot (x_R - W_R{}^W x_W) dl \tag{34}$$

[Step S164] The simulator 130 calculates an internal force integrated value $f_T$ of equation (35) and an integrated value $C_T$ and differentiation $B_T$ of equation (36).

$$\sum_{i,j} \int_{\Gamma_{T,i}} \eta_{ij}(x_i) \delta C_t(x_i:u_i, u_j) ds_i \tag{35}$$

$$\sum_{i,j} \int_{\Gamma_{T,i}} \delta\eta_{ij}(x_i) C_t(x_i:u_i, u_j) ds_i \tag{36}$$

[Step S165] The simulator 130 calculates an internal force integrated value $f_f$ of equation (37) and an integrated value $C_f$ and differentiation $B_f$ of equation (38).

$$\int_{\Gamma_{f,k}} P_k n_k \cdot \delta v ds_k \tag{37}$$

$$\int_{\Gamma_{f,k}} \delta P_k n_k \cdot v ds_k = 0 \tag{38}$$

[Step S166] The simulator 130 calculates a value $C_G$ and differentiation $B_G$ of $G_k$ ($P_k$, $F_k$, $V_k$, $Q_k$).

From the calculation results such as the matrix and integrated values calculated in the processing illustrated in FIG. 15, the simulator 130 creates and synthesizes the global matrix A and the global right-side vector b (step S153). Specifically, the synthesization of the global matrix A and the global right-side vector b is performed as follows.

$$A = \begin{bmatrix} A_{fs} & B_C^T & B_R^T & B_T^T & B_f^T & 0 & 0 \\ B_C & -\varepsilon_\lambda D_\lambda & 0 & 0 & 0 & 0 & 0 \\ B_R & 0 & -\varepsilon_\tau D_\tau & 0 & 0 & 0 & 0 \\ B_T & 0 & 0 & -\varepsilon_\eta D_\eta & 0 & 0 & 0 \\ B_f & 0 & 0 & 0 & 0 & -I & 0 \\ 0 & 0 & 0 & 0 & B_{G,P} & B_{G,F} & B_{G,O} \end{bmatrix} \tag{39}$$

$$b = -\begin{bmatrix} f_{fs} + f_C + f_R + f_T + f_f \\ C_C - \varepsilon_\lambda D_\lambda \lambda \\ C_R - \varepsilon_\tau D_\tau \tau \\ C_T - \varepsilon_\eta D_\eta \eta \\ C_f - F \\ C_G \end{bmatrix}$$

After the synthesis of the global matrix A and the global right-side vector b, processing for calculating updated amounts of variables is performed (step S154). Specifically, the following equation is solved.

$$\begin{bmatrix} A_{fs} & B_C^T & B_R^T & B_T^T & B_f^T & 0 & 0 \\ B_C & -\varepsilon_\lambda D_\lambda & 0 & 0 & 0 & 0 & 0 \\ B_R & 0 & -\varepsilon_x D_x & 0 & 0 & 0 & 0 \\ B_T & 0 & 0 & -\varepsilon_\eta D_\eta & 0 & 0 & 0 \\ B_f & 0 & 0 & 0 & 0 & -I & 0 \\ 0 & 0 & 0 & 0 & B_{G,P} & B_{G,F} & B_{G,O} \end{bmatrix} \begin{bmatrix} \Delta(v, \dot{u}) \\ \Delta\lambda \\ \Delta\lambda \\ \Delta\eta \\ \Delta P \\ \Delta F \\ \Delta(V, Q) \end{bmatrix} = \tag{40}$$

$$-\begin{bmatrix} f_{fs} + f_L + f_R + f_T + f_f \\ C_L - \varepsilon_\lambda D_\lambda \lambda \\ C_R - \varepsilon_x D_x \tau \\ C_T - \varepsilon_\eta D_\eta \eta \\ C_f - F \\ C_G \end{bmatrix}$$

In the above equation (40), Δ represents an updated amount. A time integration method such as the Newmark-β method is used for time evolution.

Next, the blood domain is extracted from the entire system updated in this way, and updating the ALE mesh (step S155) is calculated. Specifically, an equation for mesh control such as for a hyperelastic body is solved by using an interface with a new heart muscle as a boundary condition, and a new ALE mesh is generated.

If the total correction amount in the above process is not sufficiently small, the processing returns to step S152, and a calculation for updating the solution is performed. If the correction amount reaches to a predetermined value or less, the simulator 130 determines that convergence in the time increment of Δt has been achieved. Thus, calculation of the next time step is performed. When the finish time $t_{end}$ of the analysis target is reached, the simulator 130 ends the present processing.

As described above, by performing a fluid-structure interaction simulation in which the ALE method and the Lagrange multiplier method are combined with each other, an accurate simulation can be performed even when there is a site that significantly motions. Upon completion of the simulation, the simulator 130 stores the simulation results in files for post-processing.

In the second embodiment, other than a simulation by using finite element mesh models of a heart created based on biological data, the simulator 130 can perform a simulation using finite element mesh models representing a heart after an individual virtual treatment is performed, as illustrated in FIG. 11.

Next, the pre-processing (step S120) for generating heart mesh models based on respective virtual treatments will be described in more detail. In this pre-processing, the finite element mesh models 55 and 57 based on the respective virtual treatments are created not on the basis of the biological data but of the geometric model 52 created in the pre-processing (step S110). When the finite element mesh models 55 and 57 based on the respective virtual treatments are created, the procedures of the virtual treatments are given in accordance with information inputted by a doctor or by the operator 33 who has received an instruction from a doctor.

Figure 16:
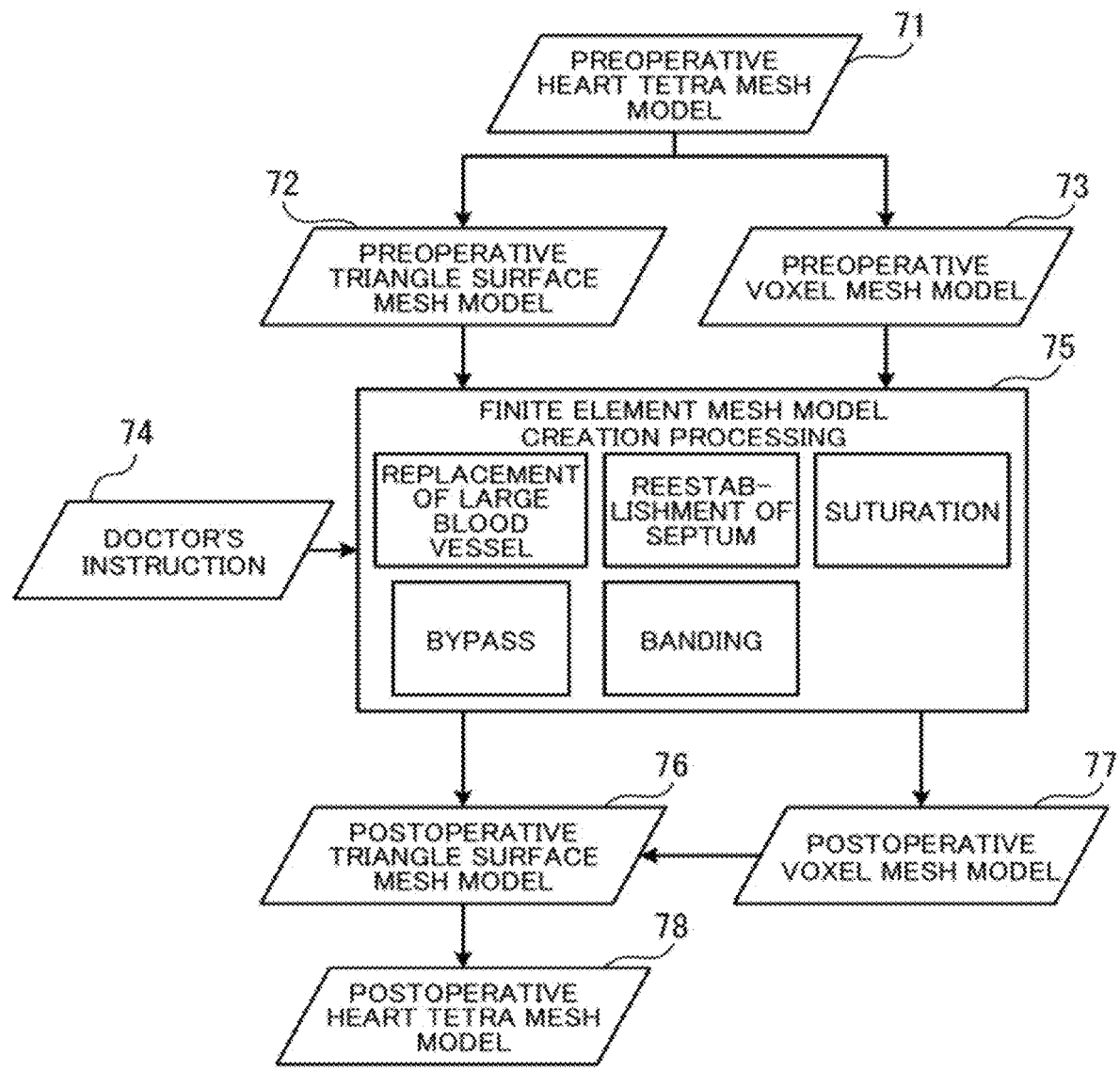
FIG. 16 illustrates an example of processing for generating postoperative finite element mesh models.

FIG. 16 illustrates an example of processing for generating postoperative finite element mesh models. For example, the pre-processing unit 120 creates a preoperative triangle surface mesh model 72 and a preoperative voxel mesh model 73 in advance on the basis of a preoperative heart tetra mesh model 71. Next, the pre-processing unit 120 performs postoperative finite element mesh model creation processing 75 in accordance with a doctor's instruction 74. For example, the pre-processing unit 120 creates the preoperative triangle surface mesh model and the preoperative voxel mesh model on the basis of the preoperative heart tetra mesh model and deforms the preoperative triangle surface mesh model 72 and the preoperative voxel mesh model 73 in accordance with the doctor's instruction 74 (the deformation includes topological deformation). In this way, a postoperative triangle surface mesh model 76 and a postoperative voxel mesh model 77 are generated. The pre-processing unit 120 generates a postoperative heart tetra mesh model 78 on the basis of the postoperative triangle surface mesh model 76 and the postoperative voxel mesh model 77.

To obtain a virtual 3D shape of a postoperative organ of a biological body whose dynamics and/or functions are to be predicted, for example, a doctor or the like or a person who has received an instruction from a doctor or the like refers to biological data of the biological body and gives the pre-processing unit 120 an instruction about morphological change of the heart or immediate organs on the basis of an operative procedure to be evaluated on a screen on which a preoperative geometric model is displayed. The operator 33 who has received a doctor's instruction orally or by written document may input the instruction to the pre-processing unit 120. On the basis of the doctor's instruction, the pre-processing unit 120 corrects segment data of the preoperative geometric model, obtains a postoperative geometric model, and performs regeneration of the corresponding surface mesh. In addition, on the basis of the doctor's instruction, the pre-processing unit 120 may obtain a postoperative triangle surface mesh model assumed by the doctor or the like by directly changing the preoperative triangle surface mesh model 72. In this way, a postoperative surface mesh (the postoperative triangle surface mesh model 76) assumed by the doctor can be obtained. In addition, the pre-processing unit 120 generates the postoperative voxel mesh model 77 by deforming the preoperative voxel mesh model 73 in accordance with a doctor's instruction.

In addition, the pre-processing unit 120 may present the doctor a list of possible techniques that can be used in a virtual operation and allow the doctor to select a technique to be used. The possible techniques are techniques used in medical virtual operations and techniques used in surgical virtual operations, for example. In addition, examples of the possible techniques include any technique relating to change of a morphological or mechanical phenomenon of a biological organ. For example, replacement of large blood vessels, reestablishment of the septum, suturation, bypass creation, flow path formation, banding (strictureplasty), valve replacement, valvuloplasty, etc. are displayed on a screen of the terminal device 31 or the like as possible techniques used in a virtual operation. For example, replacement of large blood vessels is a technique of separating two large blood vessels, a pulmonary artery and an aorta, from the heart to replace the large blood vessels with artificial blood vessels whose length has been adjusted as needed. If replacement of large blood vessels is adopted, the doctor specifies the position at which the aorta needs to be separated, for example. Accordingly, the pre-processing unit 120 separates the aorta at the specified position and deforms a finite element mesh model. If banding is selected, the doctor specifies the position at which a large blood vessel needs to be narrowed and the eventual diameter. The pre-processing unit 120 deforms the shape of the blood vessel of a finite element mesh model in accordance with the doctor's instruction.

In this way, by selecting a technique adopted in a virtual operation and deforming the preoperative triangle surface mesh model 72 and the preoperative voxel mesh model 73 in accordance with the change made by the technique, the postoperative heart tetra mesh model 78 (that has undergone topological change) is generated finally.

By performing this operation on all the procedures assumed, a plurality of heart finite element mesh models are created. For example, the finite element mesh models 55 and 57 illustrated in FIG. 11 are created.

Figure 17:
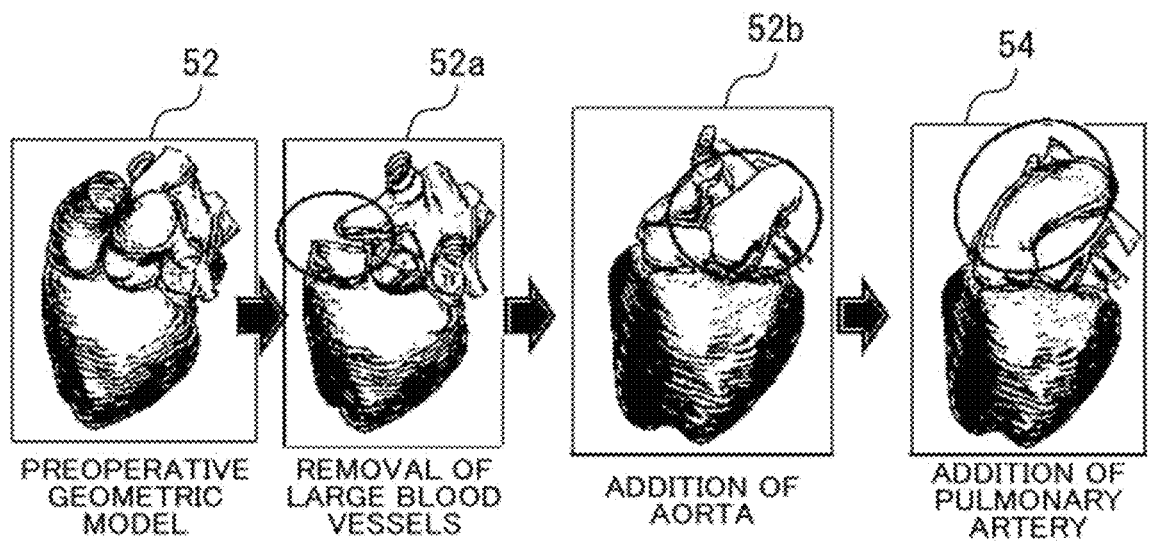
FIG. 17 illustrates an example of how a geometric model changes after large blood vessels are removed.

FIG. 17 illustrates an example of how a geometric model changes after large blood vessels are removed. For example, when a doctor inputs an instruction for removal of large blood vessels to the pre-processing unit 120, a geometric model 52a is created by removing large blood vessels from the preoperative geometric model 52. Next, when the doctor inputs an instruction for addition of an aorta to the pre-processing unit 120, a geometric model 52b is created by adding an aorta to the geometric model 52a. Next, when the doctor inputs an instruction for addition of a pulmonary artery to the pre-processing unit 120, a geometric model 54 is created by adding a pulmonary artery to the geometric model 52b. In this way, the shape is deformed in accordance with a virtual treatment.

By performing the shape deformation in this way, a finite element mesh model is created per virtual treatment procedure. In addition, a fluid-structure interaction simulation is performed for an individual finite element mesh model representing a heart after a virtual operation per virtual treatment procedure. The method of the simulation is the same as that of the simulation using a finite element mesh model representing the heart of a biological body before a virtual operation.

FIGS. 18A and 18B illustrate examples of visualization of parts of simulation results obtained before and after an operation. FIG. 18A illustrates visualization of a simulation result of a preoperative heart, and FIG. 18B illustrates visualization of a simulation result of a postoperative heart. In the example in FIGS. 18A and 18B, since the preoperative heart has a hole in its atrial septum, blood in the right atrium and blood in the left atrium are mixed. Since a wall has been formed between the right atrium and the left atrium of the postoperative heart, the blood in the right atrium and the blood in the left atrium are not mixed.

These simulation results are stored in the storage unit 110.

Figure 19:
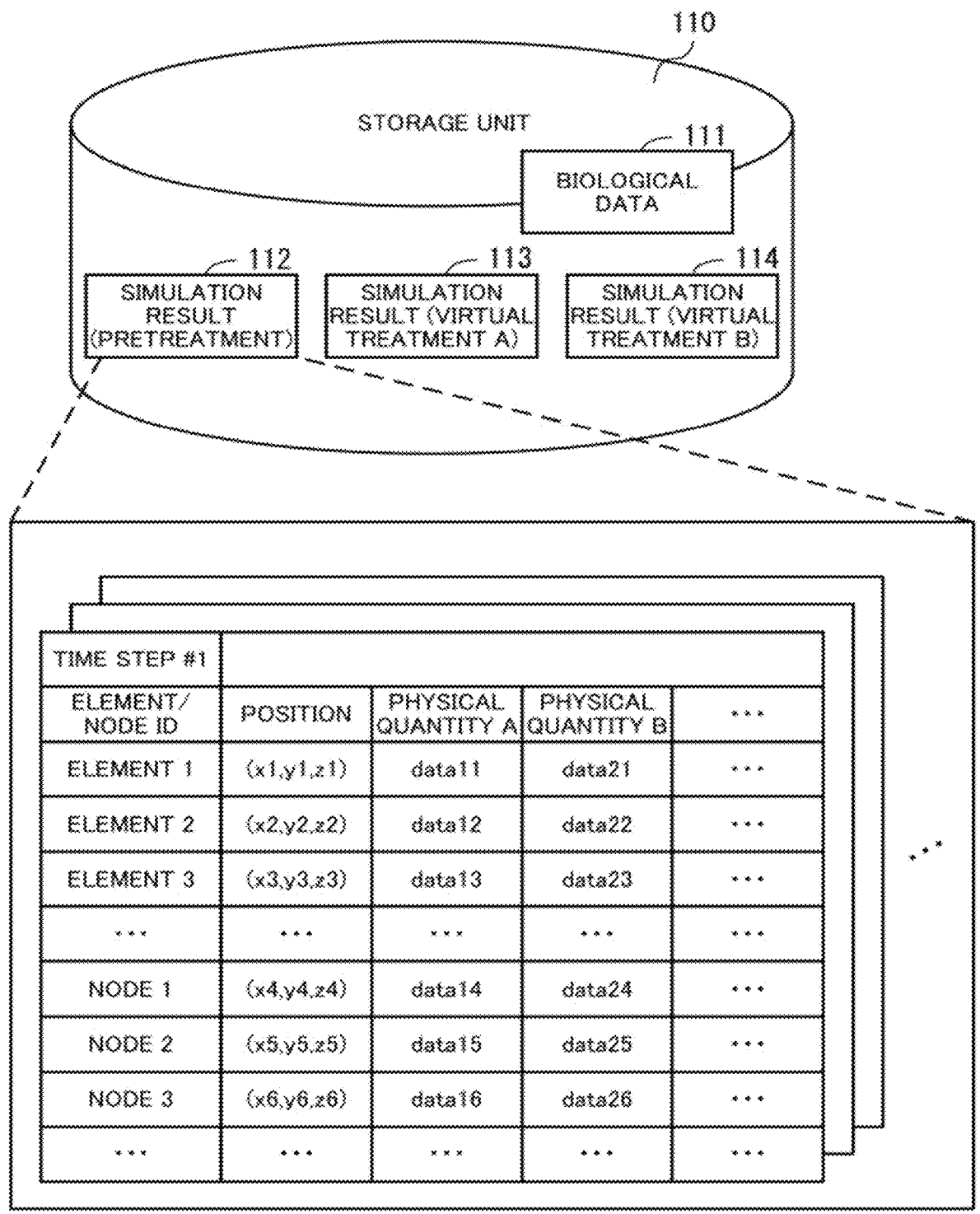
FIG. 19 illustrates an example of information stored in a storage unit.

FIG. 19 illustrates an example of information stored in the storage unit. The storage unit 110 holds biological data 111 and simulation results 112 to 114 obtained by respective simulations performed. In the example in FIG. 19, the pretreatment simulation result 112, the simulation result 113 obtained after the "virtual treatment A" is performed, and the simulation result obtained after the "virtual treatment B" is performed are stored in the storage unit 110.

The biological data 111 is information about a treatment target biological body. The biological data 111 includes various kinds of data such as a CT image, an MRI image, a 12-lead electrocardiogram, and blood pressure.

The simulation results 112 to 114 include positions of elements and nodes and physical quantities on elements and nodes per simulation time step. The elements are tetra elements, voxel elements, blood vessel elements, etc. The position of an element is a predetermined position in the element such as the center of gravity of the element. A node is an apex of an element, for example.

These simulation results are visualized by the post-processing unit 140.

Figure 20:
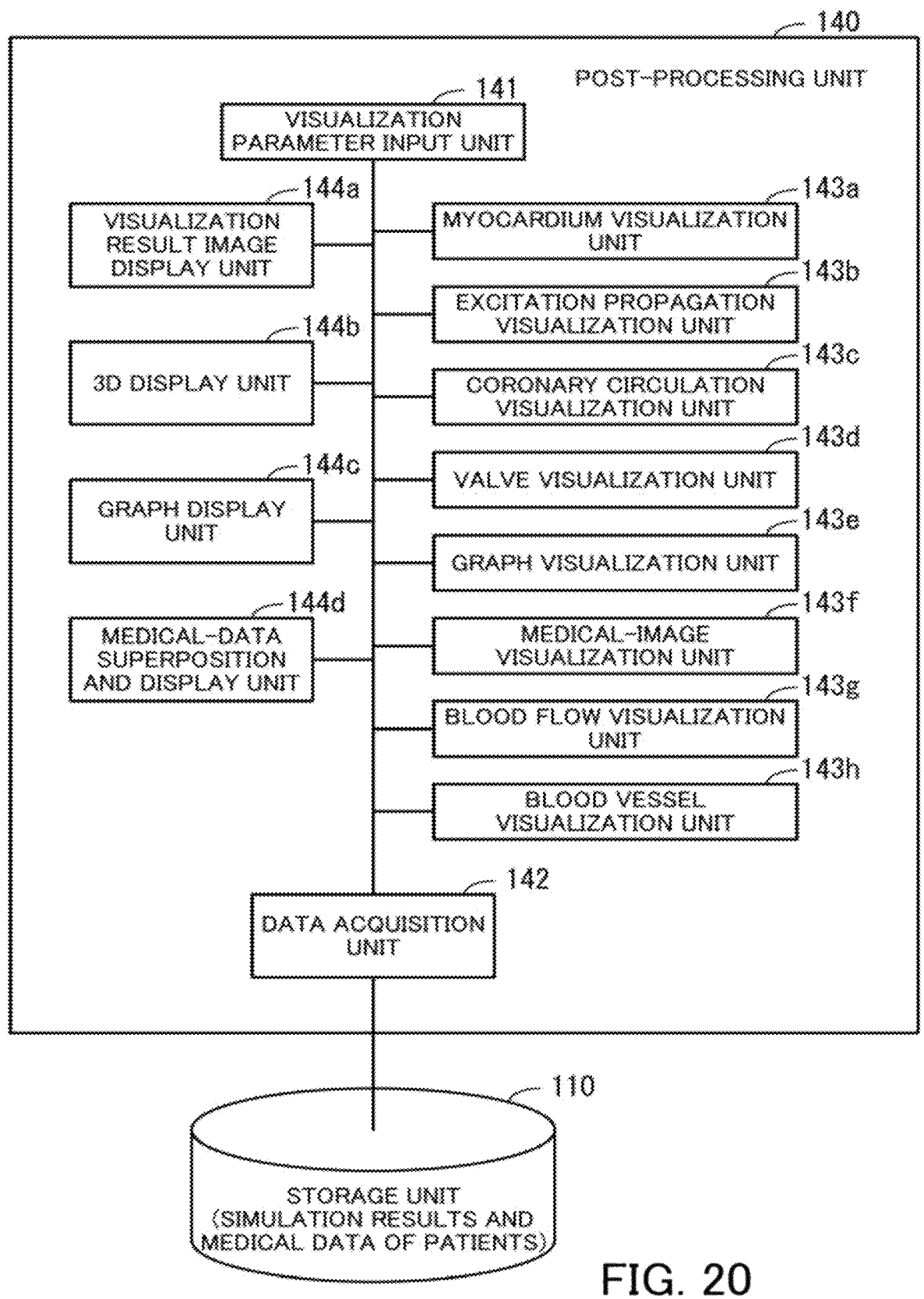
FIG. 20 illustrates an example of visualization processing.

FIG. 20 illustrates an example of visualization processing. The post-processing unit 140 includes a visualization parameter input unit 141, a data acquisition unit 142, a myocardium visualization unit 143a, an excitation propagation visualization unit 143b, a coronary circulation visualization unit 143c, a valve visualization unit 143d, a graph visualization unit 143e, a medical-image visualization unit 143f, a blood flow visualization unit 143g, a blood vessel visualization unit 143h, a visualization result image display unit 144a, a 3D display unit 144b, a graph display unit 144c, and a medical-data superposition and display unit 144d.

The visualization parameter input unit 141 receives parameters indicating visualization conditions from the terminal device 31 and inputs the received parameters to other elements performing visualization processing. The data acquisition unit 142 acquires data stored in the storage unit 110 and inputs the acquired data to other elements performing visualization or display processing.

The myocardium visualization unit 143a visualizes the behavior of the myocardium and myocardial physical quantities, for example. For example, the myocardium visualization unit 143a represents change of a value corresponding to a physical quantity such as the myocardial pressure as a color change.

The excitation propagation visualization unit 143b visualizes propagation conditions of excitation of the heart. For example, the excitation propagation visualization unit 143b represents change of a value corresponding to a myocardial voltage as a color change.

The coronary circulation visualization unit 143c visualizes coronary circulation conditions. For example, the coronary circulation visualization unit 143c represents change of a physical quantity such as the velocity or pressure of the blood flow in the coronary circulation system as a color change.

The valve visualization unit 143d visualizes the motions of the valves and the motion of the blood around the valves. For example, the valve visualization unit 143d represents the blood flow around the valves as fluid velocity vectors.

The graph visualization unit 143e statistically analyzes simulation results and represents the results in the form of a graph. For example, on the basis of a simulation result obtained per virtual operation, the graph visualization unit 143e evaluates conditions of the biological body (for example, the patient) after an individual virtual operation and generates graphs that indicate the evaluation results.

The medical-image visualization unit 143f visualizes a medical image such as a CT image or an MRI image. For example, the medical-image visualization unit 143f generates display images from image data that indicates medical images.

The blood flow visualization unit 143g visualizes the blood flow in a blood vessel. For example, the blood flow visualization unit 143g generates a fluid velocity vector that indicates a blood flow velocity.

The blood vessel visualization unit 143h generates display blood vessel object that indicates an actual blood vessel on the basis of a blood vessel element. For example, when the positions and diameters of ends of a blood vessel element are already set, the blood vessel visualization unit 143h generates a cylindrical blood vessel object that connects the ends that have the diameters.

The visualization result image display unit 144a displays an image generated through visualization on the terminal device 31 or the monitor 21. For example, the 3D display unit 144b displays a 3D image of a heart on the terminal device 31 or the monitor 21. The graph display unit 144c displays graphs created by the graph visualization unit 143e on the terminal device 31 or the monitor 21. For example, the medical-data superposition and display unit 144d superposes biological data onto a 3D image of a heart and displays the superposed image.

With the post-processing unit 140 having the functions as described above, for example, the blood flow can be visualized and displayed on a moving image showing the behavior of a heart.

Figure 21:
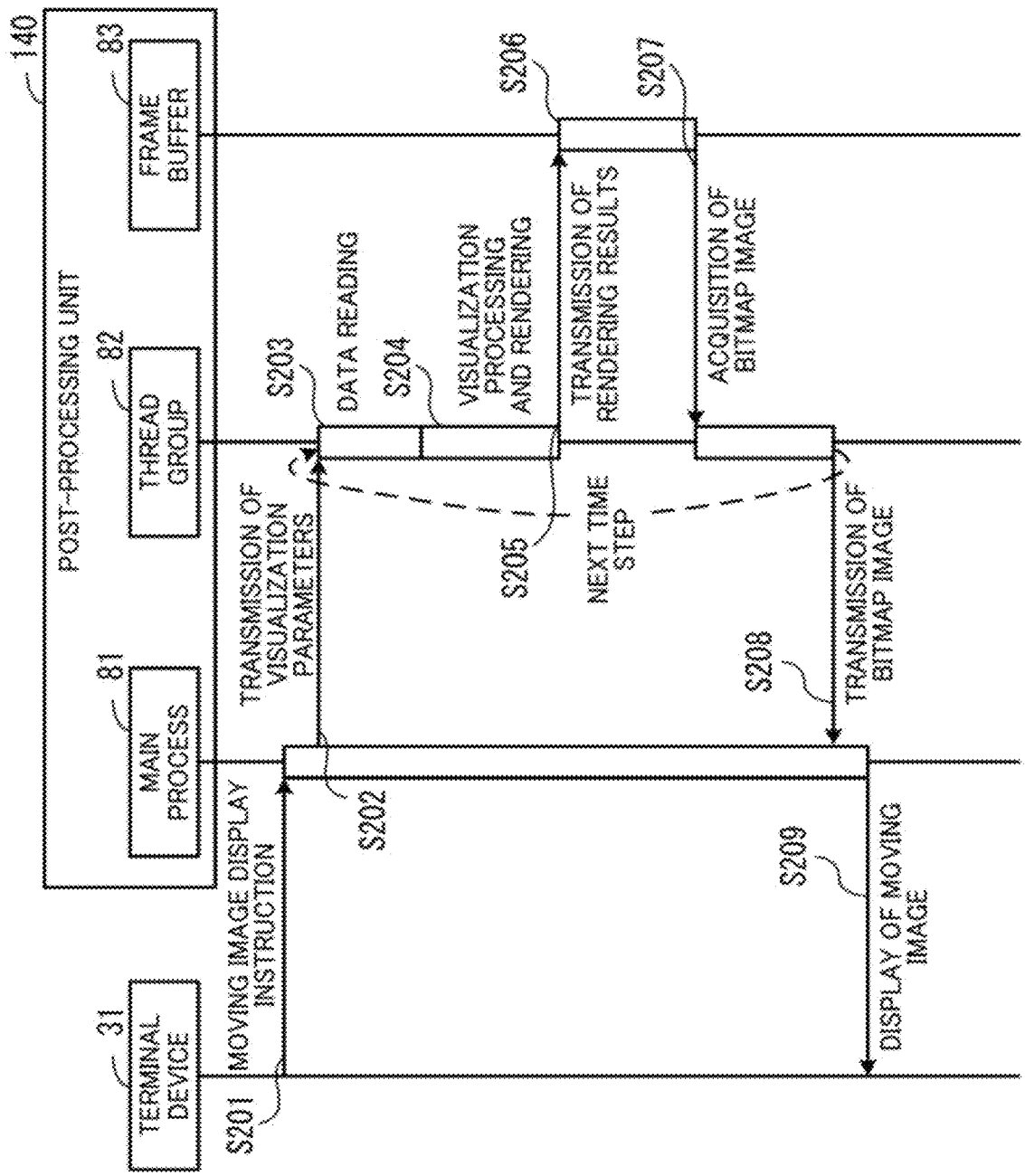
FIG. 21 illustrates an example of a procedure of the visualization processing.

FIG. 21 illustrates an example of a procedure of visualization processing. The processing illustrated in FIG. 21 illustrates visualization processing in which a system configured by at least one computer processes data corresponding to a single beat in the electrical excitation propagation simulation and the mechanical pulsation simulation. By quickly visualizing and reproducing simulation results as a moving image of a single beat of the heart, the simulation results can be observed as the motion of a natural heart. For this purpose, a plurality of threads for performing visualization processing are activated in a computer. Specifically, a thread group 82 is formed by a plurality of threads, and among m steps corresponding to a single beat (m is an integer of 1 or more), an individual thread performs processing corresponding to m/n steps (n is an integer of 1 or more indicating the number of threads activated). In addition, each thread in the thread group finally creates results of the electrical excitation propagation simulation and the mechanical pulsation simulation as a plurality of bitmap images. A main process displays these bitmap images at 1 to 60 fps in chronological order.

Specifically, the terminal device 31 transmits a moving image display instruction to the post-processing unit 140 of the prognosis prediction system 100 (step S201). Next, the main process 81 of the post-processing unit 140 transmits visualization parameters to the thread group 82 (step S202). Each thread in the thread group 82 reads simulation result data from the storage unit 110 (step S203). Next, on the basis of the read data, each thread in the thread group 82 performs visualization processing and rendering to which the specified visualization parameters are applied (step S204). Next, each thread in the thread group 82 transmits rendering results to a frame buffer 83 (step S205). The rendering results are written in the frame buffer 83 (step S206).

When a bitmap image of a single frame is created on the frame buffer 83, the corresponding thread in the thread group 82 acquires the bitmap image (step S207). Next, the corresponding thread transmits the acquired bitmap image to the main process 81 (step S208). The main process 81 arranges the bitmap images of the respective frames transmitted from the thread group 82 in chronological order and transmits the arranged bitmap images to the terminal device 31 (step S209). In this way, the terminal device 31 displays a moving image. For example, a moving image indicating the behavior of a heart including the motions of the heart valves and the blood flow around the valves is displayed on the terminal device 31.

In the second embodiment, a plurality of simulation results may be visualized in a parallel way and displayed side by side on the same screen. For example, simulation results of a heart on which a plurality of virtual operations have been performed may be arranged and displayed so that these simulation results can be compared with each other.

Figure 22:
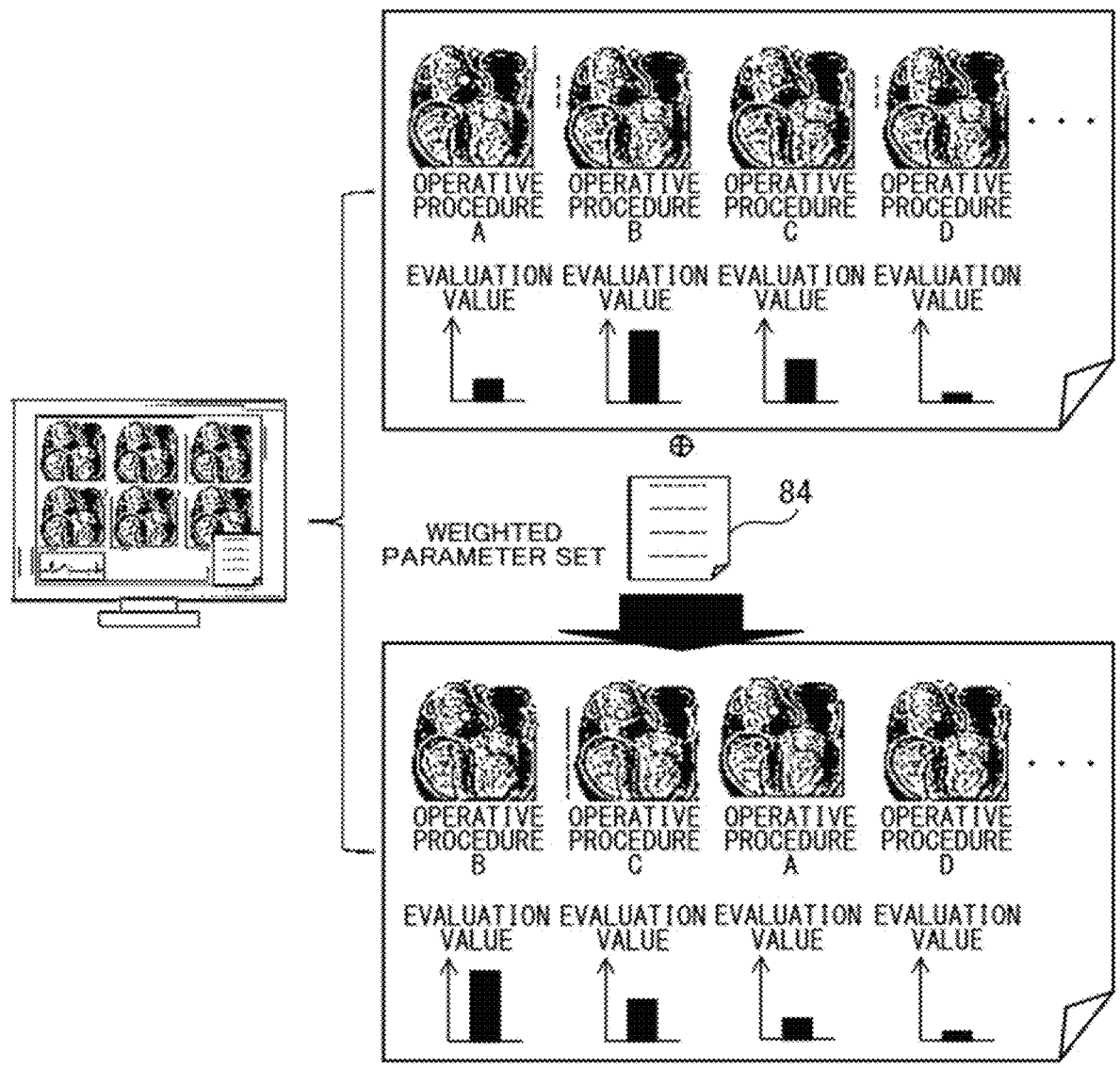
FIG. 22 illustrates an example of displaying operative procedures to be compared.

FIG. 22 illustrates an example of displaying operative procedures to be compared. When an "operative procedure A" and an "operative procedure B" are compared with each other, for example, the post-processing unit 140 displays the heart muscle and the blood flow on a cross section of the heart. When the blood flow in a domain has large oxygen saturation, the blood flow is visualized in red. In this way, postoperative effectiveness can be checked.

When displaying and comparing operative procedures, the post-processing unit 140 may calculate evaluation values for the operative procedures on the basis of a predetermined reference, rank the operative procedures on the basis of the evaluation values, and rearrange the operative procedures in descending order of rank. For example, the post-processing unit 140 may sort the operative procedures in the ascending or descending order by using parameter values specified by a doctor (for example, values corresponding to physical quantities) as evaluation values.

In addition, the post-processing unit 140 may use a weighted parameter set 84, which is a parameter set obtained by giving weight to parameters on the basis of a doctor's instructions, and rank the operative procedures. For example, in view of disease conditions of a biological body such as a patient, a doctor gives more weight to parameters indicating conditions that a postoperative biological body calls for. The doctor gives less weight to parameters that do not relate to the disease conditions of the biological body. The post-processing unit 140 sets values of the weight to the parameters in accordance with the doctor's instructions.

Figure 23:
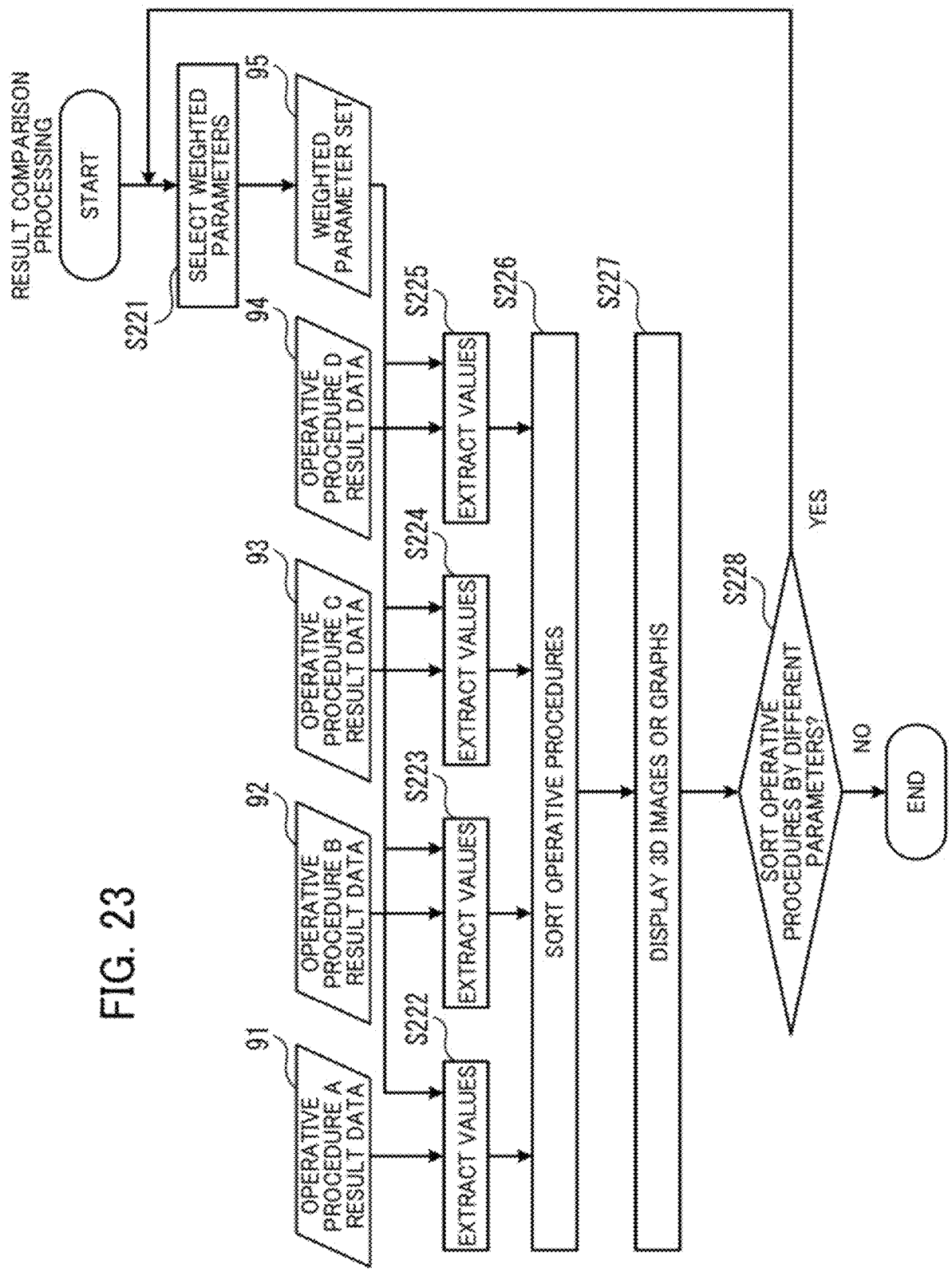
FIG. 23 is a flowchart illustrating an example of a procedure of result comparison processing.

FIG. 23 is a flowchart illustrating an example of a procedure of result comparison processing. First, the post-processing unit 140 selects weighted parameters in accordance with a doctor's instructions and generates the weighted parameter set 84 (step S221). For example, when operative procedures to be compared are displayed, the doctor may specify one or more parameters used for the ranking. For example, when the heaviest and the second heaviest parameters are specified, the post-processing unit 140 generates the weighted parameter set 84 by first selecting a parameter corresponding to the heaviest weight.

Next, the post-processing unit 140 extracts values of the parameters indicated by the weighted parameter set 84 from result data 91 to 94, indicating a simulation result per operative procedure (steps S222 to S225). For example, the post-processing unit 140 automatically sets a parameter value extraction point on the basis of information about sites of the heart added by the pre-processing. Next, the post-processing unit 140 extracts parameter values at the extraction point from data corresponding to a single pulse. For example, the post-processing unit 140 stores a maximal value of the parameter values at the extraction point corresponding to a single pulse as an evaluation value of the corresponding operative procedure in a memory. When a plurality of parameters are selected, the post-processing unit 140 performs predetermined calculation on the basis of an evaluation value per parameter and calculates the evaluation value of an operative procedure. For example, the post-processing unit 140 may multiply an evaluation value of a parameter with the weight of the parameter and uses the sum of the multiplication results as the evaluation value of the operative procedure. The post-processing unit 140 may normalize the evaluation value of each parameter. For example, the post-processing unit 140 may set "1" as an ideal value or a target value for a parameter and normalize the evaluation value of the parameter to a value between 0 and 1 on the basis of the difference from the ideal value or the target value. Next, the post-processing unit 140 may calculate the evaluation value of the operative procedure on the basis of the normalized evaluation value.

After calculating an evaluation value per operative procedure, the post-processing unit 140 sorts the operative procedures by the respective evaluation values (step S226). For example, the post-processing unit 140 compares the evaluation values of the operative procedures with each other and arranges 3D display domains and graphs of the operative procedures in descending order of evaluation value. In the example in FIG. 22, an operative procedure having a larger evaluation value is arranged on the left. The post-processing unit 140 displays graphs indicating the evaluation values of the operative procedures on the arranged 3D display domains along with the simulation results of the respective operative procedures (step S227). When the post-processing unit 140 sorts the operative procedures by different parameters, the processing returns to step S221. Otherwise, the processing proceeds to END (step S228).

For example, the doctor 32 viewing the visualization screen checks an operative procedure indicating a result in which blood with more oxygen flows into the aorta and makes a diagnostic or clinical decision.

Examples of the parameters are as follows:
Flow amount [L] into aorta per beat
Aortic systolic pressure [mmHg]
Aortic diastolic pressure [mmHg]
Mean aortic pressure [mmHg]
Aortic pressure [mmHg] (pressure in contraction phase–pressure in relaxation phase)
Left ventricular systolic pressure
Left ventricular end-diastolic pressure
Flow amount [L] into pulmonary artery per beat
Pulmonary artery systolic pressure [mmHg]
Pulmonary artery diastolic pressure [mmHg]
Pulmonary artery mean pressure [mmHg]

Pulmonary artery pressure [mmHg] (pressure in contraction phase–pressure in relaxation phase)
Right ventricular systolic pressure
Right ventricular end-diastolic pressure
Mean right atrial pressure
Mean left atrial pressure
Flow amount into pulmonary artery/flow amount into aortal per beat
Pulmonary artery systolic pressure/aortic systolic pressure per beat
Maximum blood pressure of coronary artery
Maximum blood pressure of coronary artery–myocardial pressure
Flow amount [L] into coronary artery per beat
Maximum flow velocity [m/s] in specified region of interest
Amount of energy lost by viscosity at specified site (per beat)
Amount of ATP consumed at specified site (per beat)
Heart pulsation work amount
Pulsation work amount and ATP consumption amount
Mean oxygen saturation [%] of blood at specified site per beat As described above, prognosis per operative procedure is evaluated, and an appropriate operative procedure can easily be determined. Medical staff can use these visualization results for explanation to patients and their families. In addition, the visualization results can also be used as educational material.

By interactively communicating with the interactive system 150 including the pre-processing unit 120 and the post-processing unit 140, the doctor 32 or the operator 33 can give instructions to the prognosis prediction system 100 and receive an evaluation result about prognosis per operative procedure from the prognosis prediction system 100.

Figure 24:
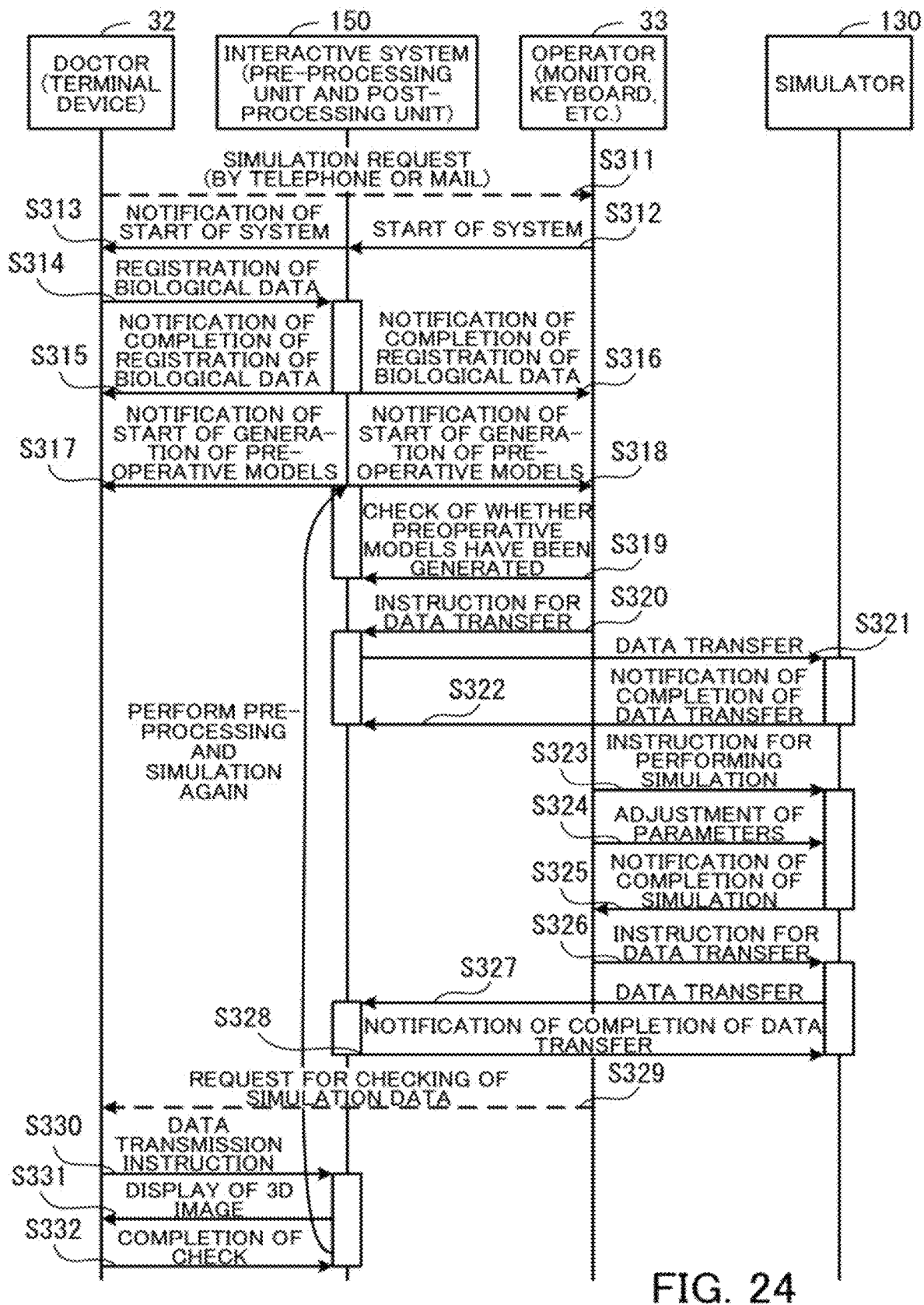
FIG. 24 is a sequence diagram illustrating the first half of a procedure of prognosis prediction processing using an interactive system.

FIG. 24 is a sequence diagram illustrating the first half of a procedure of prognosis prediction processing using the interactive system. The doctor 32 transmits a simulation request via the terminal device 31 (step S311). For example, by using phone or electronic mail, the doctor 32 requests the operator 33 to perform a simulation. In response to the request, the operator 33 activates the prognosis prediction system 100 and starts the operation of the interactive system 150 (step S312). The pre-processing unit 120 in the interactive system 150 notifies the terminal device 31 used by the doctor 32 of the start of the system (step S313).

When notified of the start of the system, the doctor 32 registers biological data in the prognosis prediction system 100 by operating the terminal device 31 (step S314). For example, the biological data stored in the terminal device 31 is transmitted to the prognosis prediction system 100 and stored in the storage unit 110. Upon completion of the registration of the biological data, the pre-processing unit 120 transmits a notification of the completion of the registration of the biological data to the terminal device 31 used by the doctor 32 (step S315). In addition, the pre-processing unit 120 displays the notification of the completion of the registration of the biological data on the monitor 21 used by the operator 33 (step S316).

Next, the pre-processing unit 120 starts generating preoperative finite element mesh models and transmits a notification of the start of the generation of the preoperative models to the terminal device 31 used by the doctor 32 (step S317). In addition, the pre-processing unit 120 displays the notification of the start of the generation of the preoperative models on the monitor 21 used by the operator 33 (step S318).

The operator 33 instructs the pre-processing unit 120 to check whether the preoperative models have been generated, by using the keyboard 22 or the mouse 23 (step S319). After the preoperative models are generated, the operator 33 receives a response to such effect from the pre-processing unit 120. After the preoperative models are generated, the operator 33 instructs the pre-processing unit 120 to transfer data by using the keyboard 22 or the mouse 23 (step S320).

The pre-processing unit 120 transfers the data used in the simulation to the simulator 130 (step S321). For large data, the pre-processing unit 120 may notify the simulator 130 of the corresponding storage area in the storage unit 110 so that the simulator 130 can use the large data. When receiving the data, the simulator 130 transmits a notification of the completion of the data transfer (step S322).

Next, the operator 33 operates the keyboard 22 or the mouse 23 to instruct the simulator 130 to perform a simulation (step S323). Next, the operator 33 operates the keyboard 22 or the mouse 23 to input information for parameter adjustment to the simulator 130 (step S324). Next, the simulator 130 performs a fluid-structure interaction simulation. Upon completion of the simulation, the simulator 130 outputs a notification of the completion of the simulation (step S325). The notification of the completion of the simulation is displayed on the monitor 21, for example.

The operator 33 operates the keyboard 22 or the mouse 23 to instruct the simulator 130 to transfer data (step S326). In accordance with the instruction, the simulator 130 transfers data indicating a simulation result to the post-processing unit 140 (step S327). For large data, the simulator 130 may notify the post-processing unit 140 of the corresponding storage area in the storage unit 110 so that the post-processing unit 140 can use the large data. When receiving the data, the post-processing unit 140 transmits a notification of the completion of the data transfer to the simulator 130 (step S328). The notification of the completion of the data transfer is displayed on the monitor 21 used by the operator 33.

The operator 33 requests the doctor 32 to check the simulation data by phone, electronic mail, or the like (step S329). The doctor 32 transmits a data transmission instruction to the post-processing unit 140 via the terminal device 31 (step S330). The post-processing unit 140 transmits a 3D image indicating the simulation result to the terminal device 31 for the terminal device 31 to display the 3D image (step S331). The doctor 32 observes the 3D image of the heart displayed on the terminal device 31 and checks the simulation result. Next, the doctor 32 notifies the post-processing unit 140 of the completion of the observation via the terminal device 31 (step S332).

In this step, if values of parameters obtained as the simulation result differ from the biological data, the processing may be performed again from the generation of the preoperative models. For example, the doctor 32 instructs the pre-processing unit 120 to perform the processing again from the generation of the preoperative models via the terminal device 31. In accordance with this instruction, the pre-processing unit 120 generates preoperative models, and the simulator 130 performs a simulation on the basis of the generated preoperative models. When the simulation is performed again, the parameters are adjusted again, for example.

Figure 25:
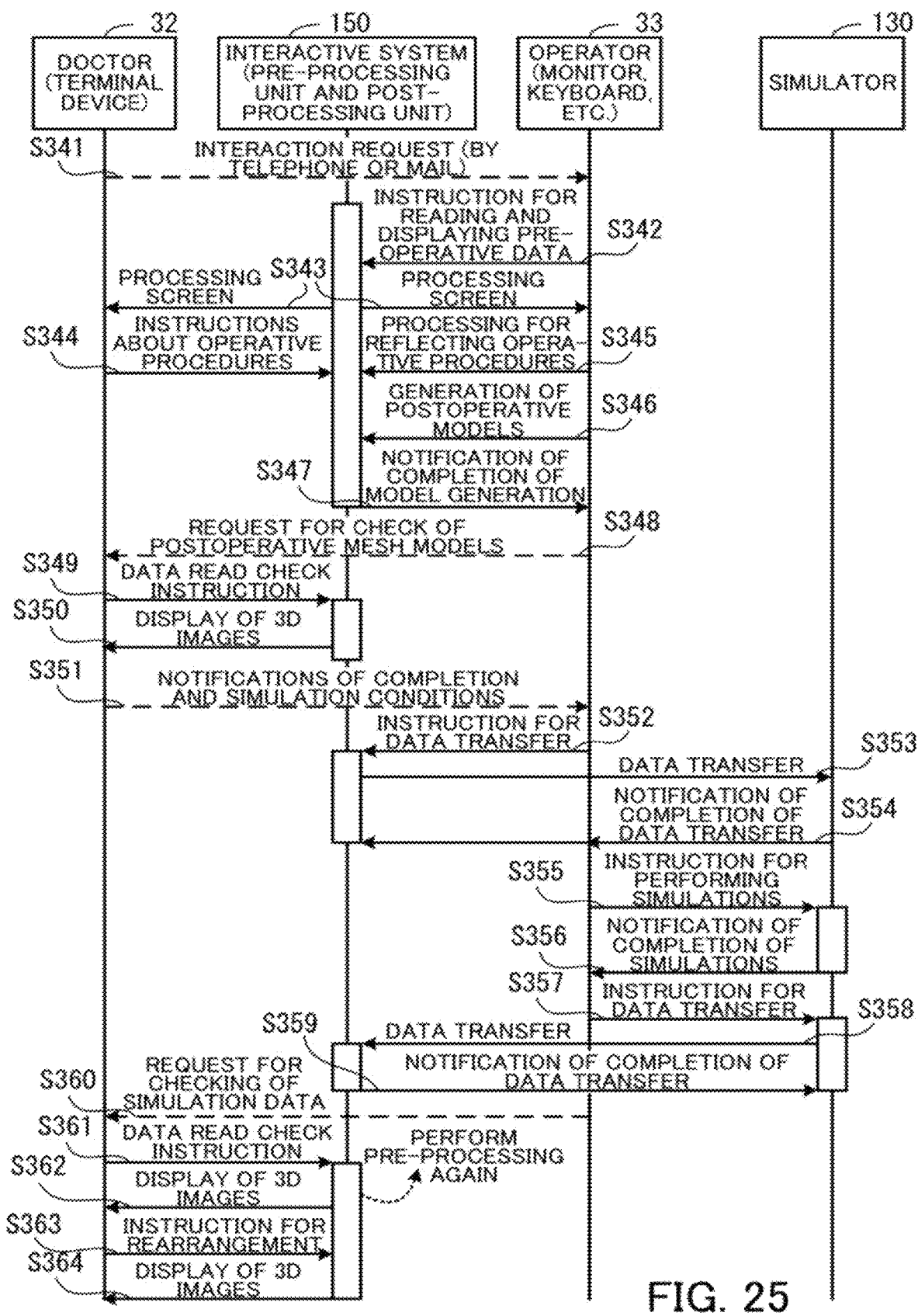
FIG. 25 is a sequence diagram illustrating the second half of the procedure of the prognosis prediction processing using the interactive system.

FIG. 25 is a sequence diagram illustrating the second half of the procedure of the prognosis prediction processing using the interactive system. The doctor 32 notifies the operator 33 of a request for interaction by phone or electronic mail (step S341). The operator 33 operates the keyboard 22 or the mouse 23 to input an instruction for reading and displaying preoperative data to the pre-processing unit 120 (step S342). The pre processing unit 120 reads data about the geometric model of the preoperative heart or the like from the storage unit 110 and displays the read data on a screen of the terminal device 31 and the monitor 21 (step S343). The doctor 32 gives instructions about a plurality of operative procedures to the pre-processing unit 120 via the terminal device 31 (step S344). The operator 33 recognizes the instructions about the operative procedures from the doctor 32 on the monitor 21. Next, the operator 33 operates the keyboard 22 or the mouse 23 to instruct the pre-processing unit 120 to reflect the specified operative procedures (step S345). In addition, the operator 33 operates the keyboard 22 or the mouse 23 to instruct the pre-processing unit 120 to generate postoperative models (step S346). The pre-processing unit 120 generates postoperative models in accordance with the instructions. Upon completion of the generation of the postoperative models, the pre-processing unit 120 displays a notification of the completion of the model generation on the monitor 21 (step S347).

The operator 33 requests the doctor 32 to check the postoperative mesh models by phone or electronic mail (step S348). The doctor 32 transmits a data read check instruction to the pre-processing unit 120 via the terminal device 31 (step S349). The pre-processing unit 120 transmits 3D images indicating the postoperative models to the terminal device 31 for the terminal device 31 to display the 3D images (step S350). After the doctor checks the 3D images of the heart displayed on the terminal device 31, the doctor 32 notifies the operator 33 of completion of checking the postoperative models and of simulation conditions by phone or electronic mail (step S351). Upon reception of the notification from the doctor 32, the operator 33 operates the keyboard 22 or the mouse to instruct the pre-processing unit 120 to transfer data (step S352). The pre-processing unit 120 transfers data used in simulations to the simulator 130 (step S353). When receiving the data, the simulator 130 transmits a notification of the completion the data transfer to the pre-processing unit 120 (step S354). In this step, the notification of the completion of the data transfer is displayed on the monitor 21 used by the operator 33.

Next, the operator 33 operates the keyboard 22 or the mouse 23 to instruct the simulator 130 to perform simulations (step S355). Next, the simulator 130 performs fluid-structure interaction simulations. Upon completion of the simulations, the simulator 130 outputs a notification of the completion of the simulations (step S356). The notification of the completion of the simulations is displayed on the monitor 21, for example.

The operator 33 operates the keyboard 22 or the mouse 23 to instruct the simulator 130 to transfer data (step S357). In accordance with the instruction, the simulator 130 transfers the data indicating the simulation results to the post-processing unit 140 (step S358). When receiving the data, the post-processing unit 140 transmits a notification of the completion of the data transfer to the simulator 130 (step S359). In this step, the notification of the completion of the data transfer is displayed on the monitor 21 used by the operator 33.

The operator 33 requests the doctor 32 to check the simulation data by phone, electronic mail, or the like (step S360). The doctor 32 transmits a data read check instruction to the post-processing unit 140 via the terminal device 31 (step S361). The post-processing unit 140 transmits 3D images indicating the simulation results to the terminal device 31 for the terminal device 31 to display the 3D images (step S362). The doctor 32 observes the 3D images of the heart displayed on the terminal device 31 and checks the simulation results. Next, the doctor 32 instructs the post-processing unit 140 to rearrange the operative procedures according to the evaluation results via the terminal device 31 (step S363). In this step, the doctor 32 can specify weight per parameter used for the rearrangement. The post-processing unit 140 transmits 3D images of the rearranged operative procedures to the terminal device 31 for the terminal device 31 to display the 3D images (step S364).

As described with reference to FIGS. 1 to 25, in the first and second embodiments, interaction between the heart wall and the luminal blood on the basis of the ALE method and interaction between the luminal blood and the heart valves on the basis of the Lagrange multiplier method are simultaneously achieved. As a result, interaction between the heart wall and the heart valves is also achieved. Namely, a heart simulation in which interaction among the three is mechanically accurately introduced is achieved.

In addition, heart and trunk finite element mesh models having geometric characteristics sufficient for a heart simulator to reproduce the heart conditions of a biological body can be generated. In addition, a heart finite element mesh model that is needed for a simulation for predicting postoperative heart conditions after an operative procedure specified by a doctor is applied to a heart is obtained. In addition, effectiveness of a plurality of operative procedures can be checked visually and quantitatively, and information for helping clinicians to make decisions can be provided.

The biological simulation apparatus, the control method thereof, and the control program thereof according to the embodiments can be used for a method for accurately deriving at least a part of the dynamics and/or functions of a biological organ on the basis of corresponding biological data. The following derivation method is an example of the usage of the apparatus according to the embodiments. Thus, the following derivation method is not limited to the usage of the apparatus according to the embodiments.

Namely, there is provided a method for deriving at least a part of the dynamics and/or functions of a biological organ through calculation on the basis of biological data. The method includes:
  determining a geometric model of a biological organ;
  creating a finite element mesh model from the geometric model;
  performing a simulation by using the finite element mesh model on the basis of biological data; and
  deriving dynamics and/or functions of the biological organ from a result of the simulation.

The biological simulation apparatus, the control method thereof, and the control program thereof according to the embodiments can be used for a method for predicting at least a part of the dynamics and/or functions of a biological organ before an operation is performed. The following method is an example of the usage of the apparatus according to the embodiments. Thus, the usage of the apparatus according to the embodiments is not limited to the following method.

Namely, there is provided a method for predicting at least a part of the dynamics and/or functions of a biological organ before an operation is performed. The method includes:
  determining a preoperative geometric model of a biological organ;
  creating a preoperative finite element mesh model from the preoperative geometric model;
  creating a postoperative finite element mesh model from the preoperative geometric model and/or the preoperative finite element mesh model;

performing a preoperative simulation by using the preoperative finite element mesh model on the basis of biological data and determining a parameter to be adjusted;

performing a postoperative simulation by using the postoperative finite element mesh model on the basis of the adjusted parameter; and deriving predicted postoperative dynamics and/or functions of the biological organ from a result of the postoperative simulation.

The following description will be made on determining a geometric model of a biological organ, creating a finite element mesh model from the geometric model, performing a simulation and parameter adjustment, deriving prediction of dynamics and/or functions of the biological organ from a result of a simulation performed after a parameter is adjusted, creating a postoperative geometric model/a postoperative finite element mesh model from the preoperative geometric model/the preoperative finite element mesh model, performing a postoperative simulation by using the postoperative finite element mesh model on the basis of the adjusted parameter, and deriving prediction of dynamics and/or functions of the biological organ from a result of the postoperative simulation.

A geometric model of a biological organ is determined as follows.

A geometric model is numerical data with which a 3D shape of a biological organ whose dynamics are to be predicted and a 3D shape of an immediate biological organ can be expressed through visualization or the like by using biological data. For example, when a curved surface of a biological organ is approximated by a group of fine triangles, the 3D shape of the biological organ is expressed by the coordinates of the corners of the triangles. The biological data includes image data representing the 3D shapes of the target biological organ and the immediate biological organ. The image data is, for example, image data with which the shape of a biological organ can be identified two or three dimensionally, such as a CT image, an MRI image, or an echocardiogram of a biological organ or an immediate biological organ thereof. Information about temporal change is attached to part of the data. Other examples of the biological data include data about indices representing biological conditions, such as test data based on a cardiovascular catheterization test, an electrocardiogram, blood pressure, etc. and numerical data based on laboratory test values, other physiological tests, data based on an imaging test, a medical history of the patient including a history of operations and records of past operations, and knowledge of the doctor.

A geometric model of a biological organ is determined by segmenting the biological organ whose dynamics are to be predicted and an immediate domain of the biological organ from image data (domain segmentation). In this operation, biological data may be reflected as needed. When the biological organ is a heart, segmentation of the heart domain, the large blood vessel domain, and so forth is performed by using image data.

A finite element mesh model is created from a geometric model as follows.

A finite element mesh model represents geometric characteristics of a biological organ. For example, a finite element mesh model represents the structure domain of a biological organ and the fluid domain inside the biological organ.

As a suitable mode, a finite element mesh model includes a structure mesh model (2) that represents a structure domain in which the tissues of a biological organ exist by using the Lagrange description and an ALE fluid mesh model (3) that represents a fluid domain in which the fluid inside the biological organ exists by using the ALE (Arbitrary Lagrangian Eulerian) description method (FIG. 1).

As another suitable mode, a finite element mesh model includes tetra mesh models of a biological organ and a domain therein, voxel mesh models of a biological organ and a domain therein, a tetra mesh model of a torso, and a voxel mesh model of a torso.

A tetra mesh model includes a triangle surface mesh that has a material number set per detailed site information and a tetra volume mesh that has a material number different per domain spatially segmented by the surfaces of the triangle surface mesh. A voxel mesh model includes structured grid data having a material number indicating domain information per voxel.

A torso voxel mesh model is structured grid data having domains segmented in accordance with the electric conductivity of the human body.

Tetra mesh models and a voxel mesh model A are created as follows. First, from segment data of a geometric model of a biological organ, a surface mesh formed by triangles is generated, and the surface mesh is segmented into finer sites. For example, the ventricles and luminal blood are segmented into finer sites such as the left ventricular free wall, the left ventricular papillary muscle, the blood domain in the left ventricle, the septum, the right ventricular free wall, the right ventricular papillary muscle, and the blood domain in the right ventricle. Thus, the sites include not only the myocardial domain but also the blood domains. For example, in the case of a heart, the sites include not only the myocardial domain but also the blood domains. Next, a triangle surface mesh segmented per site is generated. Next, two kinds of volume meshes (voxel and tetra) are created by using the surface mesh as boundaries. As a result, tetra mesh models (including a triangle surface mesh and a tetra volume mesh) and a voxel mesh model A (a voxel volume mesh) are generated.

When tetra elements are used to create a model of a thin structure, a large number of segments could be needed, and a mechanical problem could occur. In such cases, triangle shell elements or membrane elements may be used. For example, since a heart valve is a thin-walled structure, the heart valve may be segmented by using triangle shell elements or membrane elements. In the case of a linear structure such as a string, beam elements or cable elements may be used.

A torso voxel mesh model is created as follows. First, a torso domain is segmented. A torso domain is segmented into lungs, bones, organ domains mainly in accordance with luminance values from image data or other biological data. Next, when image data does not completely cover the torso domain, extrapolation processing for compensating for insufficient domains is performed. After the extrapolation processing, the position of the voxel mesh model A and the position of the torso voxel model are adjusted. The structured grid of the torso is reestablished in conformity with the voxel mesh A.

The finite element mesh models created in the above processing include the voxel mesh of the torso, the voxel mesh model A of the biological organ and the luminal blood therein, the tetra mesh model of the biological organ and the luminal blood therein, and the triangle mesh model of the thin-walled site. To associate the tetra and voxel meshes with each other, a voxel volume mesh is created by matching the torso voxel mesh model with the tetra mesh model of the biological organ. This will be used as a voxel mesh model B of the biological organ.

For example, when the biological organ is a heart, the finite element mesh models are tetra mesh models of the heart and the luminal blood, triangle mesh models of the heart valves, voxel mesh models of the heart and the luminal blood (corresponding to the above voxel mesh model B), and a voxel mesh model of the torso.

The simulation and the parameter adjustment are performed as follows.

As a suitable mode, the simulation is a fluid-structure interaction simulation about the motion of a biological organ and the motion of the fluid inside the biological organ.

It is preferable that the finite element mesh model created on the basis of a geometric model 1 include a structure mesh model 2 that represents a structure domain in which the tissues of a biological organ exist by using the Lagrange description and an ALE fluid mesh model 3 that represents a fluid domain in which the fluid inside the biological organ exists by using the ALE description method (FIG. 1). Among the interfaces made by the structure domain and the fluid domain, an interface between a domain in which a site other than a certain site 2a of the biological organ exists and the fluid domain is determined to be a first interface 4. In addition, among the interfaces made by the structure domain and the fluid domain, an interface between a domain in which the certain site 2a of the biological organ exists and the fluid domain is determined to be a second interface 5. For example, the certain site 2a is a site protruding into the domain in which the ALE fluid mesh model 3 exists. For example, when the biological organ is a heart, the certain site 2a is a heart valve.

In the simulation, both the behavior of the biological organ and the motion of the fluid therein, including the interaction of the biological organ and the fluid, are simultaneously solved. A fluid-structure interaction simulation that obtains ever-changing equilibrium conditions is performed. The structure mesh model 2 is deformed in accordance with the motion of the biological organ, along with the progress of the fluid-structure interaction simulation. The ALE fluid mesh model is deformed by using an interface-tracking analysis method in such a manner that the first interface 4 is tracked. More specifically, the ALE fluid mesh model 3 is deformed in such a manner that no gap is formed on the first interface 4 or no overlap is formed with the structure mesh model 2 (the structure domain). Movement of nodes inside the ALE fluid mesh model 3 is artificially controlled separately from the motion of the fluid so that the soundness of each of the meshes is maintained. In addition, when performing the fluid-structure interaction simulation, the position of the second interface 5 using the ALE fluid mesh model 3 as a reference is captured by using an interface-capturing analysis method. For example, on the coordinate space for defining the shape of the ALE fluid mesh model 3, the coordinates of the second interface 5 are calculated.

The fluid-structure interaction simulation enables a highly accurate simulation by deforming the ALE fluid mesh model 3 in accordance with the interface-tracking analysis method and by tracking the first interface 4 with the deformed the ALE fluid mesh model 3. In addition, the certain site 2a such as a heart valve, which significantly motions and which has an interface that is difficult to track by using the interface-tracking analysis method, is captured on the ALE fluid mesh model 3 by using the interface-capturing analysis method. In this way, a fluid-structure interaction simulation is performed on a biological organ having a site that has an interface difficult to track. For example, the ALE method may be used as the interface-tracking analysis method. In addition, for example, a method based on the Lagrange multiplier method may be used as the interface-capturing analysis method (see, for example, T. Hisada et al., "Mathematical Considerations for Fluid-structure Interaction Simulation of Heart Valves").

FIG. 2 illustrates examples of fluid-structure interaction analysis based on an interface-tracking analysis method using an ALE mesh when the biological organ is a heart. FIG. 2 illustrates an ALE mesh used in the analysis and blood flow obtained as an analysis result. When an interface of the heart deforms, the ALE mesh also deforms with the deformation of the heart. In addition, the fluid velocity (fluid velocity vectors) and the pressure of the blood are analyzed on the coordinate system in which the deformable ALE mesh is defined. In this way, accurate analysis is performed. However, there is a limit to the deformation of the ALE mesh. Thus, it is difficult to track an interface of a site that significantly deforms such as a heart valve by using the ALE fluid mesh.

FIG. 3 illustrates the behavior of a heart and the motions of valves. The left portion in FIG. 3 illustrates a heart when the ventricles contract, and the right portion in FIG. 3 illustrates the heart when the ventricles relax. For example, when the heart muscle of a left ventricle 8 contracts, an aortic valve 7 opens, and the blood in the left ventricle 8 is discharged. In this state, a mitral valve 6 is closed. When the heart muscle of the left ventricle 8 relaxes, the mitral valve 6 opens, and blood flows into the left ventricle 8. In this state, the aortic valve 7 is closed. In this way, an individual valve opens or closes in accordance with the pulsation of the heart. When the heart motions, an individual valve deforms with the opening and closing operations more significantly than the atria and ventricles deform with the contraction and relaxation of the heart muscles. It is difficult to track such valves that deform significantly by using the ALE fluid mesh model.

In contrast, with the Lagrange multiplier method, since the fluid mesh does not track an interface, the fluid around the heart valves can also be analyzed.

FIG. 4A to 4C illustrates an example of fluid-structure interaction analysis based on an interface-capturing analysis method using the Lagrange multiplier method. FIG. 4A illustrates a structure mesh model of an aortic valve created independently from a fluid mesh model. FIG. 4B illustrates a spatially-fixed Euler fluid mesh model representing the fluid domain inside an aorta. FIG. 4C illustrates simulation results in which the fluid velocities of the blood are indicated by vectors. Assuming that the wall of the aorta is a rigid body and does not deform, the fluid mesh can be represented by a spatially-fixed Euler mesh.

In this way, in conventional fluid-structure interaction analysis based on the Lagrange multiplier method, analysis using a spatially-fixed Euler fluid mesh model has been performed. Thus, fluid-structure interaction analysis can be performed on a site that undergoes extreme deformation such as a valve, and change of the blood flow around the valve over time can be analyzed, for example. However, in the fluid-structure interaction analysis based on the Lagrange multiplier method, since an interface is not tracked, the stability and analysis accuracy of this analysis are less than those of the fluid-structure interaction analysis based on the interface tracking method using the ALE mesh.

Thus, an interface that can be tracked by the interface-tracking analysis method is tracked by using a deformable ALE mesh, and an interface that is difficult to track such as a valve is captured from the deformable ALE mesh.

FIGS. 5A to 5C illustrate analysis techniques that are compared with each other. FIG. 5A illustrates an interface-tracking analysis method using the ALE method. FIG. 5B illustrates an analysis method in which an interface is captured from a spatially-fixed Euler mesh. FIG. 5C illustrates an analysis method in which an interface is captured from a deformable ALE mesh.

A structure mesh model 41 representing a structure domain in which the tissues of a biological organ exist is deformed as the simulation time progresses from t to t+Δt. When the interface-tracking analysis method is used, a ALE fluid mesh model 42 formed by the ALE mesh also deforms as the structure mesh model 41 deforms. However, since a fluid mesh model 43 based on the interface-capturing analysis method is spatially fixed, the fluid mesh model 43 does not deform even when the structure mesh model 41 deforms.

In the analysis method in which an interface is captured from a deformable mesh, an interface of the structure mesh model 41 in a trackable range is tracked by using the deformable ALE fluid mesh model 42. Regarding an untrackable site (for example, a valve site 41a), the position of the interface of the corresponding site is calculated on the coordinate system in which the ALE fluid mesh model 42 is defined. In this way, an interface of a site that significantly deforms such as the valve site 41a can be captured.

Next, interface-tracking and -capturing methods will be described in detail.

FIGS. 6A and 6B illustrate coordinate systems for interface tracking and capturing. FIGS. 6A and 6B illustrate an Euler (space) coordinate system $(x_1, x_2)$, a Lagrange (material) coordinate system $(X_1, X_2)$, and an ALE coordinate system $(\chi_1, \chi_2)$ that arbitrarily motions and deforms. A myocardial domain $\Omega^S$ is represented by the Lagrangian coordinate system. A blood domain $\Omega^f$ is represented by the ALE coordinate system. A heart valve 44 is protruding into the blood domain $\Omega^f$. While 3D representation is used in reality, two dimensional (2D) representation is used herein for simplicity.

An absolute velocity $v_i$ at a material point X, a velocity $w_i$ at the material point X observed from the ALE coordinate system, and a velocity ($v_i$ with "^") in the ALE coordinate system controlled by an analyst are expressed as equations (41) to (43), respectively.

$$v_i = \left.\frac{\partial x_i(X, t)}{\partial t}\right|_X \tag{41}$$

$$w_i = \left.\frac{\partial \chi_i(X, t)}{\partial t}\right|_X \tag{42}$$

$$\hat{v}_i = \left.\frac{\partial x_i(\chi, t)}{\partial t}\right|_\chi \tag{43}$$

If an equation of the motion of a continuum body derived from the law of conservation of momentum and the law of conservation of mass are written from the ALE coordinate system, equations (44) are (45) are obtained.

$$\left.\hat{\rho}\frac{\partial v_i}{\partial t}\right|_\chi + \hat{\rho} w_j \frac{\partial v_i}{\partial x_j} = \frac{\partial \hat{\Pi}_{ji}}{\partial x_j} + \hat{\rho} g_i \tag{44}$$

$$\left.\frac{\partial \hat{\rho}}{\partial t}\right|_\chi + \frac{\partial \hat{\rho} w_i}{\partial x_i} = 0 \tag{45}$$

In the above equations, ρ with "^" and Π with "^" indicate the mass density and the 1st Piola-Kirchhiff stress tensor defined by using the reference configuration in the ALE coordinate system as a reference. The second term on the right-hand side of equation (44) represents arbitrary body force.

For example, the motion equation of the luminal blood of the heart is described from the ALE coordinate system different from the Lagrangian coordinate system used for the myocardial domain as illustrated in FIG. 1 (see, for example, M. A. Castro et al., "Computational fluid dynamics modeling of intracranial aneurysms: effects of parent artery segmentation on intra-aneurysmal hemodynamics" and E. Tang et al., "Geometric Characterization of Patient-Specific Total Cavopulmonary Connections and its Relationship to Hemodynamics"), and the valve motions in the space of the ALE coordinate system. Thus, to cause the blood and the valve to interact with each other by applying the interface-capturing analysis method based on the Lagrange multiplier method proposed in "Multi-physics simulation of left ventricular filling dynamics using fluid-structure interaction finite element method" by H. Watanabe et al., the ALE coordinate system is basically used as the common coordinate system. Thus, the law of conservation of mass in one-side blood domain $\Omega^K$ (K=1, 2) defined by a delta function near a point A on the valve is imposed as expressed by the equation (46). The match between a blood velocity $v_F$ and the velocity components in a normal direction $n^C$ regarding a valve velocity $v_s$ is imposed as expressed by the equation (47), where $\Gamma^C$ represents an interface.

$$\int_{\Omega^K} \delta(\chi - \chi_A)\left(\left.\frac{\partial \hat{\rho}}{\partial t}\right|_\chi + \frac{\partial \hat{\rho} w_i}{\partial x_i}\right) d\Omega^K = 0 \tag{46}$$
$$K = 1, 2$$

$$n^C \cdot (v_F(\chi) - v_S(\chi)) = 0 \text{ on } \Gamma^c \tag{47}$$

However, since the formulation based on the concept of the reference configuration of the ALE coordinate system complicates the equations, the equations including the motion equation of the blood are converted to be expressed in the Euler coordinate system. Consequently, since equations (44) and (45) are rewritten as equations (48) and (49), equations (46) and (47) are rewritten as equations (50) and (51), respectively. Note that the following relationships in equation (52) are used for the conversion. In equation (48), $T_{ji}$ represents the Cauchy stress tensor component.

$$\left.\rho\frac{\partial v_i}{\partial t}\right|_\chi + \rho c_j \frac{\partial v_i}{\partial x_j} = \frac{\partial T_{ji}}{\partial x_j} + \rho g_j \tag{48}$$

$$\left.\frac{\partial \rho}{\partial t}\right|_\chi + c_i \frac{\partial \rho}{\partial x_i} + \rho \frac{\partial v_i}{\partial x_i} = 0 \tag{49}$$

$$\int_{\Omega^K} \delta(x - x_A)\left(\left.\frac{\partial \rho}{\partial t}\right|_x + c_i \frac{\partial \rho}{\partial x_i} + \rho \frac{\partial v_i}{\partial x_i}\right) d\Omega^K = 0 \tag{50}$$
$$K = 1, 2$$

-continued $$n^C \cdot (v_F(x) - v_S(X(x))) = 0 \text{ on } \Gamma^c \quad (51)$$

$$\chi = x, \hat{v}_i = 0, v_i = w_i, c_i = v_i - \hat{v}_i = w_j \frac{\partial x_i}{\partial \chi_j} = w_i \quad (52)$$

In contrast, the motion equation of a heart muscle is expressed as the following equation by using the Lagrangian coordinate system.

$$\rho_0 \frac{\partial v}{\partial t}\bigg|_\chi = \nabla_\chi \cdot \Pi + \rho_0 \tilde{g} \quad (53)$$

Next, regarding the constitutive equation of the material, the blood is expressed by the following equation as incompressible Newton fluid, wherein μ represents a viscosity coefficient.

$$T = -pI + 2\mu D \quad (54)$$

$$D = \tfrac{1}{2}(\nabla_x \otimes v + v \otimes \nabla_x) \quad (55)$$

$$\nabla_x \cdot v = 0 \quad (56)$$

Thus, the first and second terms of the law of conservation of mass are eliminated. In addition, if the tangent stiffness of the constitutive equation of the heart muscle described in the Lagrangian coordinate system is represented by a fourth-order tensor C, the following equations are established. In the following equations, S represents the 2nd Piola-Kirchhoff stress, F represents the deformation gradient tensor, and E represents the Green-Lagrange strain tensor.

$$\Pi = S \cdot F^T \quad (57)$$

$$F = x \otimes \nabla_x \quad (58)$$

$$\Pi = (\det F) F^{-1} \cdot T \quad (59)$$

$$S = C : E \quad (60)$$

$$E = \tfrac{1}{2}\{\nabla_x \otimes u + u \otimes \nabla_x + (\nabla_x \otimes u) \cdot (u \otimes \nabla_x)\} \quad (61)$$

Thus, first, by displaying a variational form equation of the Navier-Stokes equation of the blood observed based on the ALE coordinate system in the Euler coordinate system, equation (62) is derived. Next, a variational form equation of the motion equation of the heart wall is derived as equation (63). In addition, by applying the divergence theorem to constraint condition equations (64) and (65) between the blood and the valve, equation (66) is derived. Consequently, the stationary condition equation of the entire system is expressed as equation (67).

$$\delta W_f^{ALE} \equiv \int_{\Omega^f} \delta v \cdot \rho^f \frac{\partial v}{\partial t}\bigg|_\chi d\Omega^f + \int_{\Omega^f} \delta v \cdot \rho^f (v \otimes \nabla_x) \cdot C d\Omega^f + \quad (62)$$

$$2\mu \int_{\Omega^f} \delta D : D d\Omega^f - \int_{\Omega^f} \rho^f \nabla_x \cdot \delta v d\Omega^S -$$

$$\int_{\Omega^f} \delta p (\nabla_x \cdot v) d\Omega^f - \int_{\Omega^f} \delta v \cdot \rho^f g d\Omega^f - \int_{\Gamma^f} \delta v \cdot \underline{t} d\Gamma^f$$

$$\delta W_S = \quad (63)$$

$$\int_{\Omega^S} \delta \dot{u} \cdot \rho^S \ddot{u} d\Omega^S + \int_{\Omega^S} \delta E : S d\Omega^S - \int_{\Omega^S} \delta u \cdot \rho^S g d\Omega^S - \int_{\Gamma^S} \delta u \cdot \underline{t} d\Gamma^S$$

$$\int_{\Omega^K} \delta(x - x_A) \nabla_x \cdot v d\Omega^K = 0, K = 1, 2 \quad (64)$$

$$n^C \cdot (v - \dot{u}) = 0 \text{ on } \Gamma^c \quad (65)$$

$$\sum_{K=1}^{2}(-1)^K \frac{1}{2} \int_{\Omega^f} \nabla \otimes \delta(x - x_A) \cdot v(x) d\Omega^K + \quad (66)$$

$$\int_{\Gamma^c} \delta(x - x_A) n^C \cdot \dot{u}(x_A) d\Gamma^C \equiv C(x; v, \dot{u})$$

$$\delta W^{total} \equiv \delta W_f^{ALE} + \delta W_S^1 + \delta W_S^2 + \int_{\Gamma^c} \lambda(x) C(x; \delta v, \delta \dot{u}) d\Gamma^C + \quad (67)$$

$$\int_{\Gamma^c} \delta \lambda(x) C(x; v, \dot{u}) d\Gamma^C - \int_{\Gamma^c} \varepsilon_\lambda \delta \lambda(x) \lambda(x) d\Gamma^C = 0$$

In the middle side of equation (67), $\delta W_S^1$ and $\delta W_S^2$ represent the first variations of the entire potential regarding the heart muscle and an individual valve. The last term in the middle side is a stabilization term.

In addition, connection between a heart valve and a wall, interaction made by contact between heart valves or between a heart valve and a heart wall, and connection with the systemic circulation analogy circuit can also be performed by using the Lagrange multiplier method. In this case, the stationary condition equation of the entire system is expressed as equation (68).

$$\delta W^{total} \equiv \delta W_f^{ALE} + \delta W_S^1 + \delta W_S^2 + \int_{\Gamma^c} \lambda(x) C(x; \delta v, \delta \dot{u}) d\Gamma^C + \quad (68)$$

$$\int_{\Gamma^c} \delta \lambda(x) C(x; v, \dot{u}) d\Gamma^C - \int_{\Gamma^c} \varepsilon_\lambda \delta \lambda(x) \lambda(x) d\Gamma^C +$$

$$\int_{\Gamma_L} \tau(x) \cdot (\delta x_L - W_L^W \delta x_W) dl + \int_{\Gamma_L} \delta \tau(x) \cdot (x_L - W_L^W x_W) dl -$$

$$\int_{\Gamma_R} \varepsilon_\tau \delta \tau(x) \cdot \tau(x) dl + \sum_{i,j} \int_{\Gamma_{T,i}} \eta_{ij}(x_i) \delta C_t(x_i; u_f, u_j) ds_i +$$

$$\sum_{i,j} \int_{\Gamma_{T,i}} \delta \eta_{ij}(x_i) C_t(x_i; u_i, u_j) ds_i - \sum_{ij} \int_{\Gamma_{T,i}} \varepsilon_\eta \delta \eta_{ij}(x_i) \eta_{ij}(x_i) ds +$$

$$\int_{\Gamma_{f,k}} P_k n_k \cdot \delta v ds_k + \int_{\Gamma_{f,k}} \delta P_k (n_k \cdot v - F_k) ds_k = 0$$

$\Gamma_L$ represents a connection interface between a heart valve and a myocardial wall, $\chi_L$, and $\chi_W$ represent node coordinates of a heart valve and a myocardial wall, $W_R^W$ represents an interpolation coefficient from a myocardial wall node to a connection point, $\Gamma_{T,i}$ represents a surface that could be brought into contact, and $C_t$ is a contact condition equation. In addition, $\Gamma_{f,k}$ represents a blood domain interface connected to the systemic circulation analogy circuit, $F_k$ represents a flow volume to the systemic circulation model on a connection surface. In addition, $P_k$ represents the blood pressure of the systemic circulation model on a connection surface, and $v_k$ and $Q_k$ represent the blood pressure variable and the capacity variable in the systemic circulation model, respectively. With these parameters, the equation is solved as a system including the next balance equation of the systemic circulation analogy circuit.

$$G_k(P_k, F_k, V_k, Q_k) = 0 \quad (69)$$

On the basis of the above formulation, finite element discretization is performed, and a heart simulation is performed. A procedure of the fluid-structure interaction simulation by a simulator is as follows.

FIG. 14 is a flowchart illustrating an example of a procedure of the simulation.

[Step S151] The simulator 130 updates time of the time step. For example, the simulator 130 adds a predetermined time increment Δt to the current time t. When the simulation is started, the time is set to t=0.

[Step S152] The simulator 130 calculates a stiffness matrix, internal force integration, and various conditional integrations and the corresponding differentiations. The matrix, differentiations, and integrations reflect the ALE fluid-structure interaction and fluid-structure interaction based on the Lagrange multiplier method.

[Step S153] The simulator 130 synthesizes a global matrix A and a global right-side vector b.

[Step S154] The simulator 130 calculates updated amounts of variables.

[Step S155] The simulator 130 updates the ALE mesh.

[Step S156] The simulator 130 determines whether the calculation result has converged. If so, the processing proceeds to step S157. If not, the processing returns to step S152 and the calculation processing is performed again.

[Step S157] The simulator 130 determines whether the simulation time t has reached finish time $t_{end}$. For example, the finish time $t_{end}$ is when a simulation of a single beat of the heart is finished. When the finish time $t_{end}$ has been reached, the simulator 130 ends the simulation. If the finish time $t_{end}$ has not been reached, the processing returns to step S151.

The processing in steps S152 to S155 will hereinafter be described in detail.

FIG. 15 is a flowchart illustrating an example of a procedure of the differentiation and integration calculation processing.

[Step S161] The simulator 130 calculates an internal force integrated value $f_{fs}$ and a stiffness matrix $A_{fs}$ of equation (70).

$$\delta W_f^{ALE} + \delta W_S^1 + \delta W_S^2 \tag{70}$$

[Step S162] The simulator 130 calculates an internal force integrated value $f_C$ of equation (71) and an integrated value $C_C$ and differentiation $B_C$ of equation (72).

$$\int_{\Gamma^C} \lambda(x) C(x : \delta v, \delta u) d\Gamma^C \tag{71}$$

$$\int_{\Gamma^C} \delta\lambda(x) C(x : v, u) d\Gamma^C \tag{72}$$

[Step S163] The simulator 130 calculates an internal force integrated value $f_R$ of equation (73) and an integrated value $C_R$ and differentiation $B_R$ of equation (74).

$$\int_{\Gamma_R} \tau(x) \cdot (\delta x_R - W_R{}^W \delta x_W) dl \tag{73}$$

$$\int_{\Gamma_R} \delta\tau(x) \cdot (x_R - W_R{}^W x_W) dl \tag{74}$$

[Step S164] The simulator 130 calculates an internal force integrated value $f_T$ of equation (75) and an integrated value $C_T$ and differentiation $B_T$ of equation (76).

$$\sum_{i,j} \int_{\Gamma_{T,i}} \eta_{ij}(x_i) \delta C_t(x_i : u_i, u_j) ds_i \tag{75}$$

$$\sum_{i,j} \int_{\Gamma_{T,i}} \delta\eta_{ij}(x_i) C_t(x_i : u_i, u_j) ds_i \tag{76}$$

[Step S165] The simulator 130 calculates an internal force integrated value $f_f$ of equation (77) and an integrated value $C_f$ and differentiation $B_f$ of equation (78).

$$\int_{\Gamma_{f,k}} P_k n_k \cdot \delta v ds_k \tag{77}$$

$$\int_{\Gamma_{f,k}} \delta P_k n_k \cdot v ds_k = 0 \tag{78}$$

[Step S166] The simulator 130 calculates a value $C_G$ and differentiation $B_G$ of $G_k(P_k, F_k, V_k, Q_k)$.

From the calculation results such as the matrix and integrated values calculated in the processing illustrated in FIG. 15, the simulator 130 creates and synthesizes the global matrix A and the global right-side vector b (step S153). Specifically, the synthesis of the global matrix A and the global right-side vector b is performed as follows.

$$A = \begin{bmatrix} A_{fs} & B_C^T & B_R^T & B_T^T & B_f^T & 0 & 0 \\ B_C & -\varepsilon_\lambda D_\lambda & 0 & 0 & 0 & 0 & 0 \\ B_R & 0 & -\varepsilon_\tau D_\tau & 0 & 0 & 0 & 0 \\ B_T & 0 & 0 & -\varepsilon_\eta D_\eta & 0 & 0 & 0 \\ B_f & 0 & 0 & 0 & 0 & -I & 0 \\ 0 & 0 & 0 & 0 & B_{G,P} & B_{G,F} & B_{G,Q} \end{bmatrix} \tag{79}$$

$$b = - \begin{bmatrix} f_{fs} + f_C + f_R + f_T + f_f \\ C_C - \varepsilon_\lambda D_\lambda \lambda \\ C_R - \varepsilon_\tau D_\tau \tau \\ C_T - \varepsilon_\eta D_\eta \eta \\ C_f - F \\ C_G \end{bmatrix}$$

After the synthesis of the global matrix A and the global right-side vector b, processing for calculating updated amounts of variables is performed (step S154). Specifically, the following equation is solved.

$$\begin{bmatrix} A_{fs} & B_C^T & B_R^T & B_T^T & B_f^T & 0 & 0 \\ B_C & -\varepsilon_\lambda D_\lambda & 0 & 0 & 0 & 0 & 0 \\ B_R & 0 & -\varepsilon_x D_x & 0 & 0 & 0 & 0 \\ B_T & 0 & 0 & -\varepsilon_\eta D_\eta & 0 & 0 & 0 \\ B_f & 0 & 0 & 0 & 0 & -I & 0 \\ 0 & 0 & 0 & 0 & B_{G,P} & B_{G,F} & B_{G,Q} \end{bmatrix} \begin{bmatrix} \Delta(v, u) \\ \Delta\lambda \\ \Delta\lambda \\ \Delta\eta \\ \Delta P \\ \Delta F \\ \Delta(V, Q) \end{bmatrix} = \tag{80}$$

$$- \begin{bmatrix} f_{fs} + f_L + f_R + f_T + f_f \\ C_C - \varepsilon_\lambda D_\lambda \lambda \\ C_R - \varepsilon_x D_x \tau \\ C_T - \varepsilon_\eta D_\eta \eta \\ C_f - F \\ C_G \end{bmatrix}$$

In the above equation (80), Δ represents an updated amount. A time integration method such as the Newmark-β method is used for time evolution.

Next, the blood domain is extracted from the entire system updated in this way, and updating the ALE mesh (step S155) is calculated. Specifically, an equation for mesh control such as for a hyperelastic body is solved by using an interface with a new heart muscle as a boundary condition, and a new ALE mesh is generated.

If the total correction amount in the above process is not sufficiently small, the processing returns to step S152, and a calculation for updating the solution is performed. If the correction amount reaches to a predetermined value or less, the simulator 130 determines that convergence in the time increment of Δt has been achieved. Thus, calculation of the next time step is performed. When the finish time $t_{end}$ of the analysis target is reached, the simulator 130 ends the present processing.

As described above, by performing a fluid-structure interaction simulation in which the ALE method and the Lagrange multiplier method are combined with each other, an accurate simulation can be performed even when there is a site that significantly motions.

In another suitable embodiment, the biological organ is a heart, and the simulation includes an electrical excitation propagation simulation and a mechanical pulsation simulation. The mechanical pulsation simulation is performed in accordance with a simulation method of fluid-structure interaction in which the heart tetra mesh model is a structure mesh model that represents a structure domain and the luminal blood tetra mesh model is a fluid mesh model that represents a fluid domain (FIG. 13).

The electrical excitation propagation simulation and parameter adjustment can be performed as follows. First, fiber and sheet distributions are set to a heart voxel mesh model on the basis of literature values or the like. In addition, a Purkinje fiber distribution or an equivalent endocardial conductance distribution is set. In addition, a site of earliest activation is set to the endocardium. In addition, cell models having three kinds of APD distribution are distributed in the long axis direction and the short axis direction. For example, a method in "Computational fluid dynamics modeling of intracranial aneurysms: effects of parent artery segmentation on intra-aneurysmal hemodynamics" by M. A. Castro et al. is used for these settings. Next, a simulator performs an electrical excitation propagation simulation by combining the heart voxel mesh model set as described above and a torso voxel mesh model having a body surface on which electrodes for a standard 12-lead electrocardiogram are set. Next, parameters are adjusted so that the simulation result matches the result of the standard 12-lead electrocardiogram test on the biological body whose dynamics are to be predicted. Examples of the parameters include a site of earliest activation of the endocardium and three kinds of APD distribution.

By the electrical excitation propagation simulation and the parameter adjustment, for example, the time history of the calcium ion concentration (calcium concentration history) of an individual element of the heart tetra mesh model constituting the heart can be determined.

The mechanical pulsation simulation and parameter adjustment can be performed as follows.

First, as is the case with the heart voxel mesh model, fiber and sheet distributions are set to the heart tetra mesh model. In addition, boundary conditions for performing a mechanical simulation are set, and duplexing of pressure nodes for mechanical analysis and duplexing of nodes at an interface between the blood and the heart muscle are performed, for example. In addition, information about an individual site of the heart is also given. Next, a natural-condition heart model (tetra element) is created from the heart tetra mesh model. Namely, while the heart tetra mesh model is created for a relaxation phase of the heart, to obtain a natural shape corresponding to a free-stress condition, a natural-condition heart model (tetra element) is created by performing suitable mechanical finite element analysis and reducing the heart. Along with this reduction operation, the tetra mesh of the luminal blood domain is also deformed simultaneously. When the mesh of the luminal blood domain is deformed significantly, a tetra mesh is newly created.

As a simulation finite element model, a combination of cusp models of shell or membrane elements and chorda tendineae models of beam elements or cable elements is added to the natural-condition heart model (tetra model) and luminal blood model (tetra model), as needed. In addition, a systemic circulation model adjusted to the biological conditions is connected. The systemic circulation model is an electrical circuit analogy model formed by suitably combining discrete resistance and capacitance defined by assuming that the blood pressure is voltage and the blood flow is current. On the basis of the contraction force obtained by using the calcium concentration history of an individual tetra element of the natural-condition heart model to which the systemic circulation model is connected for an excitation contraction coupling model, a mechanical pulsation simulation is performed.

Parameters are adjusted so that the simulation result match the biological data of the biological body whose dynamics and/or functions are to be derived, such as a result of a cardiovascular catheterization test, a blood pressure value, a pressure-volume relationship, and image data about an MRI image, a CT image, an echocardiogram, and mechanical indices extracted from the biological data. When the oxygen saturation or concentration of the blood of the biological body whose dynamics are to be predicted has already been measured, an advection diffusion equation using a fluid velocity distribution of the blood obtained through fluid-structure interaction analysis is solved by using a finite element method using the same ALE fluid mesh as that used in the fluid-structure interaction analysis, and the conformity is checked. Examples of the parameters adjusted include the transition rate that determines the stochastic state transition of myosin molecules in the excitation-contraction coupling model, coordination parameters, and the resistance and capacitance of the systemic circulation model.

The parameter adjustment is performed on the biological body whose dynamics and/or functions are to be derived, so as to match the corresponding biological data. Likewise, the parameter adjustment is also performed on virtual condition change that does not involve morphological change of the biological organ, namely, on virtual biological data set to virtual change of a function of the biological organ or virtual change of a motion or a physical property of fluid. When the biological organ is a heart, for example, the virtual change of a function signifies performing parameter adjustment for virtually reducing the contraction of the heart muscle of the heart or changing an APD distribution in the electrical excitation propagation simulation. The virtual change of a motion or a physical property of fluid signifies performing parameter adjustment for virtually decreasing or increasing the amount of blood that circulates in the body.

In accordance with the following method, dynamics and/or functions of the biological organ are derived from the simulation result after the parameter adjustment.

The simulation result after the parameter adjustment includes the positions of element or nodes and physical quantities on elements or nodes per simulation time step. The elements are heart tetra elements, heart voxel elements, luminal blood tetra elements, etc. The position of an element is a predetermined position in the element such as the center of gravity of the element. A node is an apex of an element, for example. For example, such a simulation result is visualized as graphs or the like, and dynamics and/or functions of the biological organ can be derived.

The dynamics and/or functions of the biological organ derived from the simulation result after the parameter adjustment include information relating to the motion of the biological organ having temporal and spatial resolution that cannot be observed by the measurement techniques practically used. The measurement techniques practically used can only observe the motion of the biological organ in a limited spatial range with limited temporal or spatial resolution. In the derivation of the simulation result, the motion of the entire biological organ or the entire site to be observed that cannot be observed by the measurement techniques practically used or physical quantities that cannot be clinically observed can be observed. Consequently, detailed dynamics and/or functions of the observation target can be obtained.

In addition, the dynamics and/or functions of the biological organ derived from the simulation result after the parameter adjustment on virtual biological data can be used for prediction of dynamics or functions of the cardiovascular system after medication treatment or fluid or blood infusion treatment is performed on the biological body.

When the biological organ is a heart, the dynamics and/or functions obtained by visualization or other derivation methods can be used for prediction of the pump performance of the heart, the hemodynamics, the load on the heart and the lungs, etc. For example, the pump performance of the heart represents the motion of the heart and the motions and functions of the heart valves. For example, the hemodynamics includes the pressure generated by the heart, the pressure at an individual cardiovascular site, the flow volume of the blood at an individual cardiovascular site, the velocity of the blood flow at an individual cardiovascular site, the oxygen saturation of the blood at an individual cardiovascular site, the dissolved gas partial pressure of the blood at an individual cardiovascular site, and the blood concentration of drug at an individual cardiovascular site. For example, the load on the heart and lungs includes the energy consumption amount or efficiency of the heart, the energy conditions of the blood fluid, the pressure caused on the heart muscle, the conditions of the coronary circulation, the systemic vascular resistance, and the pulmonary vascular resistance. Among these derivation results, those for which clinical measurement techniques exist accurately match their respective measured values to such an extent that the derivation results can be applied for clinical purposes. The dynamics and/or functions of the biological organ derived from the simulation result after the parameter adjustment indicate the conditions of the biological body to such an extent that the dynamics and/or functions can practically be used for clinical purposes. Thus, for example, a doctor can gain a better understanding of the pump performance of the heart, the hemodynamics, the load on the heart and the lungs, etc. and can make diagnostic or clinical decisions by using the dynamics and/or functions as a reference.

Upon completion of the simulation, the visualization processing for predicting the dynamics and/or functions of the biological organ can be performed by displaying a space-time distribution of physical variables corresponding to a result of the simulation. For example, numerical data of and temporal change of an individual phenomenon, such as the membrane potential or stress by the myocardial excitation propagation or the velocity or the pressure of the blood flow per beat, is visualized by 2D or 3D image processing. In this processing, observation from various points of view is enabled by changing the viewpoint in accordance with input information. In addition, by generating cross sections, observation of any one of the cross sections is enabled. In addition, by quickly generating a moving image of the behavior of the heart and displaying the behavior as an animation, observation suitable for examination, diagnosis, or treatment is enabled. In addition, a part of the heart muscle can be extracted and displayed so that change of the extracted part over time can be checked.

FIG. 20 illustrates an example of visualization processing. Namely, the post-processing unit 140 includes a visualization parameter input unit 141, a data acquisition unit 142, a myocardium visualization unit 143a, an excitation propagation visualization unit 143b, a coronary circulation visualization unit 143c, a valve visualization unit 154d, a graph visualization unit 143e, a medical-image visualization unit 143f, a blood flow visualization unit 143g, a blood vessel visualization unit 143h, a visualization result image display unit 144a, a 3D display unit 144b, a graph display unit 144c, and a medical-data superposition and display unit 144d.

The visualization parameter input unit 141 receives parameters indicating visualization conditions from the terminal device 31 and inputs the received parameters to other elements performing visualization processing. The data acquisition unit 142 acquires data stored in the storage unit 110 and inputs the acquired data to other elements performing visualization or display processing.

The myocardium visualization unit 143a visualizes the behavior of the myocardium and myocardial physical quantities, for example. For example, the myocardium visualization unit 143a represents change of a value corresponding to a physical quantity such as the myocardial pressure as a color change.

The excitation propagation visualization unit 143b visualizes propagation conditions of excitation of the heart. For example, the excitation propagation visualization unit 143b represents change of a value corresponding to a myocardial voltage as a color change.

The coronary circulation visualization unit 143c visualizes coronary circulation conditions. For example, the coronary circulation visualization unit 143c represents change of a physical quantity such as the velocity or pressure of the blood flow in the coronary circulation system as a color change.

The valve visualization unit 143d visualizes the motions of the valves and the motion of the blood around the valves. For example, the valve visualization unit 143d represents the blood flow around the valves as fluid velocity vectors.

The graph visualization unit 143e statistically analyzes simulation results and represents the results in the form of a graph. For example, on the basis of a simulation result obtained per virtual operation, the graph visualization unit 143e evaluates conditions of the patient after an individual virtual operation and generates graphs that indicate the evaluation results.

The medical-image visualization unit 143f visualizes a medical image such as a CT image or an MRI image. For example, the medical-image visualization unit 143f generates display images from image data that indicates medical images.

The blood flow visualization unit 143g visualizes the blood flow in a blood vessel. For example, the blood flow visualization unit 143g generates a fluid velocity vector that indicates a blood flow velocity.

The blood vessel visualization unit 143h generates display blood vessel object that indicates an actual blood vessel on the basis of a blood vessel element. For example, when the positions and diameters of ends of a blood vessel element are already set, the blood vessel visualization unit 143h generates a cylindrical blood vessel object that connects the ends that have the diameters.

The visualization result image display unit 144a displays an image generated through visualization on the terminal device 31 or the monitor 21. For example, the 3D display unit 144b displays a 3D model of a heart on the terminal device 31 or the monitor 21. The graph display unit 144c displays graphs created by the graph visualization unit 143e on the terminal device 31 or the monitor 21. For example, the medical-data superposition and display unit 144d superposes biological data onto a 3D model of a heart and displays the superposed image.

In accordance with the following method, a postoperative geometric model/postoperative finite element mesh model is created from a preoperative geometric model/preoperative finite element mesh model.

A postoperative finite element mesh model is created by deforming a preoperative geometric model and creating a postoperative geometric model or by directly deforming a preoperative finite element mesh model.

A postoperative geometric model is a virtual 3D shape of a postoperative biological organ whose dynamics and/or functions are to be predicted or an immediate biological organ of the biological organ. The postoperative geometric model can be created by changing segment data of the corresponding preoperative geometric model. A postoperative finite element mesh model can be created from the postoperative geometric model. A postoperative finite element mesh model can also be created by deforming a triangle surface mesh model and a voxel mesh model of the corresponding preoperative finite element mesh model (the deformation includes topological deformation). In addition, a postoperative geometric model can be created by deforming a preoperative finite element mesh model through mechanical analysis and newly generating a triangle surface mesh model on the basis of the deformed preoperative finite element mesh model. If a postoperative geometric model is created in this way, a postoperative finite element mesh can be generated by using this postoperative geometric model.

FIG. 16 illustrates an example of processing for generating postoperative finite element mesh models. For example, a preoperative triangle surface mesh model and a preoperative voxel mesh model are created on the basis of a preoperative heart tetra mesh model. Next, the preoperative triangle surface mesh model and the preoperative voxel mesh model are deformed in accordance with an operative procedure assumed (the deformation includes topological deformation). In this way, a postoperative triangle surface mesh model and a postoperative voxel mesh model are generated. A postoperative heart tetra mesh model is generated on the basis of the postoperative triangle surface mesh model and the postoperative voxel mesh model.

To obtain a virtual 3D shape of a postoperative organ of a biological body whose dynamics and/or functions are to be predicted, for example, a doctor or the like or a person who has received an instruction from a doctor or the like can refer to biological data of the biological body and indicate change of the morphology or shape of the heart or immediate organs on the basis of an operative procedure to be evaluated on a screen on which a preoperative geometric model is displayed. On the basis of the indication about the postoperative organ of the biological body, a postoperative geometric model can be obtained by correcting segment data of the preoperative geometric model, and regeneration of the corresponding surface mesh can be performed. In addition, on the basis of the indication, a postoperative triangle surface mesh model assumed by the doctor or the like can be obtained by directly changing the preoperative triangle surface mesh model. In addition, on the basis of the indication, the postoperative voxel mesh model and the postoperative heart tetra mesh model can be regenerated by deforming the preoperative voxel mesh model (the deformation includes topological deformation).

A virtual 3D shape of a postoperative organ of a biological body whose dynamics and/or functions are to be predicted (or a postoperative geometric model or a postoperative finite element mesh model based on the virtual 3D shape) can be created for techniques used in the following virtual operations. Examples of the techniques include techniques used in medical operations and techniques used in surgical operations. Specifically, replacement of large blood vessels, reestablishment of the septum, suturation, bypass creation, flow path formation, banding (strictureplasty), valve replacement, and valvuloplasty. Namely, examples of the techniques include any technique relating to change of a morphological or mechanical phenomenon of a biological organ. For example, replacement of large blood vessels is a technique of separating two large blood vessels, a pulmonary artery and an aorta, from the heart to replace the large blood vessels with artificial blood vessels whose length has been adjusted as needed. If a doctor or the like indicates the position at which the aorta needs to be separated, the preoperative heart tetra mesh model is deformed so that the aorta at the indicated position is separated. In the case of banding, if a doctor or the like indicates or instructs the position at which a blood vessel needs to be narrowed and the eventual diameter, the shape of the blood vessel of the preoperative heart tetra mesh model is deformed.

FIG. 17 illustrates an example of how a geometric model changes after large blood vessels are removed. For example, when a doctor or the like inputs an instruction for or indicates removal of large blood vessels, a geometric model 52a is created by removing large blood vessels from a preoperative geometric model 52. Next, when the doctor or the like inputs an instruction for or indicates addition of an aorta, a geometric model 52b is created by adding an aorta to the geometric model 52a. Next, when the doctor or the like inputs an instruction for or indicates addition of a pulmonary artery, a geometric model 54 is created by adding a pulmonary artery to the geometric model 52b. In this way, the shape is deformed by the operation.

A postoperative finite element mesh model may be created for each of a plurality of different techniques (for example FIG. 11), and postoperative simulations may be performed by using the created postoperative finite element mesh models. In this way, regarding each of the techniques, prediction of postoperative dynamics and/or functions can be derived, and the obtained results can be compared with each other. In addition, a doctor or the like can use the results when selecting a most suitable operative procedure.

A postoperative simulation is performed by using a postoperative finite element mesh model on the basis of adjusted parameters as follows.

A postoperative simulation is performed on a postoperative finite element mesh model on the basis of adjusted parameters in the same way as the above simulation (hereinafter, a preoperative simulation) is performed. As the adjusted parameters, a combination of parameters (a best parameter set) that approximates the biological data the most, which is obtained by the preoperative simulation and parameter adjustment can be used. The adjusted parameters may be a combination of parameters that approximate the virtual biological data the most, which is set in view of virtual condition change of the biological organ, such as virtual change of a function of the biological organ or virtual change of a physical property or motion of fluid of the biological organ. The adjusted parameters may be obtained by performing a simulation and parameter adjustment on the postoperative finite element mesh model. For example, the optimized parameters are parameters included in the electrical conductance of the heart muscle, the site of earliest activation, the APD spatial distribution, the excitation-contraction coupling model, the systemic circulation model, and the like.

When a postoperative finite element mesh model is created for each of a plurality of different techniques (for example, FIG. 11), a simulation is performed on each of the postoperative finite element mesh models by using the optimized parameters obtained by the preoperative simulation and parameter adjustment in the same way as the preoperative simulation.

The prediction of dynamics and/or functions of a postoperative biological organ is derived from the result of a postoperative simulation in accordance with the following method.

The prediction of dynamics and/or functions of a postoperative biological organ is derived from the result of a postoperative simulation in accordance with the same method as the method of the derivation of the prediction of dynamics and/or functions in the preoperative simulation.

FIGS. 18A and 18B illustrate examples of visualization of parts of simulation results obtained before and after an operation. FIG. 18A illustrates visualization of a simulation result of a preoperative heart, and FIG. 18B illustrates visualization of a simulation result of a postoperative heart. In the example in FIGS. 18A and 18B, since the preoperative heart has a hole in its atrial septum, blood in the right atrium and blood in the left atrium are mixed. Since a wall has been formed between the right atrium and the left atrium of the postoperative heart, the blood in the right atrium and the blood in the left atrium are not mixed.

To assist a doctor in selecting the most suitable operative procedure, an assumable postoperative finite element mesh model may be created from each of a plurality of different techniques. In this way, prediction of dynamics and/or functions of an individual postoperative biological organ can be derived from the corresponding postoperative simulation result, and the results can be compared with each other.

Examples of the prediction of dynamics and/or functions of a postoperative biological organ obtained by visualization or other derivation methods include prediction relating to formation of a new shape such as an autogenous, homogeneous, or heterogeneous biological material or an artificial object on a part of a biological organ structure, maintenance on malfunction of a biological organ by using the above biological material or artificial object, and replacement of a function by deforming a part of a biological organ structure. For example, a doctor can predict conditions of a heart that has undergone an operation for congenital heart disease, conditions of a cardiovascular system that has undergone percutaneous coronary intervention or an aortocoronary bypass operation, conditions of a cardiovascular system that has undergone a heart valve replacement operation, conditions of a cardiovascular system that has undergone cardiac valvuloplasty, conditions of a cardiovascular system that has undergone cardiac valve annuloplasty, conditions of a cardiovascular system that has undergone pacemaker treatment including cardiac resynchronization treatment, conditions of a cardiovascular system that has undergone treatment for aortic disease, conditions of a cardiovascular system that has undergone treatment for pulmonary arteriopathy, conditions of a cardiovascular system that has undergone installation of a circulatory assist device, and conditions of a cardiovascular system that has undergone other cardiovascular treatment. Examples of the operation for congenital heart disease include an open-heart operation for congenital heart disease, a catheterization operation for congenital heart disease, and an extracardiac operation for congenital heart disease. Examples of the catheterization operation for congenital heart disease include an operation using a defect closure device and an operation using a balloon catheter. Examples of the extracardiac operation for congenital heart disease include the Blalock-Taussig shunt, pulmonary artery banding, the Glenn operation, and TCPC. The heart valve replacement operation and the cardiac valvuloplasty include a catheterization operation. Examples of the circulatory assist device include medical devices generally used for circulatory assistance, such as an intra-aortic balloon pump, a percutaneous cardiopulmonary support device, a left ventricular assist device, and a right ventricular assist device. The cardiovascular treatment includes medical treatment.

In addition, regarding the prediction of dynamics and/or functions of a postoperative biological organ derived from a postoperative simulation result after parameter adjustment on virtual biological data, if the biological organ is a heart, for example, when the treatment content including medication, management of artificial respiration, or the like is changed after an operation on the heart, part or all of the change may be reflected on the prediction of dynamics and/or functions of the postoperative biological organ. As a result, more clinically accurate and practicable prediction of dynamics and/or functions is achieved.

The derivation results of the prediction of postoperative dynamics and/or functions indicate biological conditions to such an extent that the derivation results can practically be used for clinical purposes. A doctor or the like can compare the results about the pump performance of the postoperative heart, the hemodynamics, the load on the heart and the lungs, etc. Namely, a doctor or the like can determine the most suitable treatment in view of the results.

According to one aspect, a highly accurate fluid-structure interaction simulation on a biological organ having a deformable site that has an interface difficult to track is enabled.

According to another aspect, by displaying a fluid-structure interaction simulation result, prediction of dynamics or functions of a biological organ derived from the fluid-structure interaction simulation result or prediction of dynamics or functions after an actual operation performed by a doctor can effectively be used for clinical applications by doctors, for example.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A biological simulation apparatus comprising:
a memory configured to hold a geometric model that represents a structure of a biological organ including a heart, a part of an aortic, a part of a pulmonary artery, and one or more valves, the biological organ being divided into at least one valve and a remaining part of the biological organ other than the at least one valve, the at least one valve being included in the heart, the aortic, or the pulmonary artery, the one or more valves protruding into a blood domain in which blood inside the biological organ exists; and a processor configured to perform a procedure including:

representing, among domains in the geometric model, a structure domain in which tissues of the biological organ exist by using a structure mesh model defined on a Lagrangian coordinate system based on a Lagrange description, the structure domain including a first domain in which the remaining part of the biological organ exists and a second domain in which the at least one valve exists, the blood domain existing in a lumen of the structure domain;

representing the blood domain by using an ALE (Arbitrary Lagrangian Eulerian) fluid mesh model based on an ALE description method, a first interface being located between the first domain and the blood domain, a second interface being located between the second domain and the blood domain; and performing a fluid-structure interaction simulation that obtains ever-changing equilibrium conditions by deforming the structure mesh model in accordance with a motion of the biological organ along with a progress of the simulation, tracking the first interface by the ALE fluid mesh model by simultaneously solving both motions of the biological organ and the blood therein, including the interaction of the biological organ and the blood, wherein the performing of the fluid-structure interaction simulation includes:

deforming the structure mesh model in accordance with the motion of the biological organ along with a progress of the simulation;

tracking, by using an interface tracking method, the first interface by the ALE fluid mesh model by deforming an ALE coordinate system defining the shape of the ALE fluid mesh model in such a manner that no gap is formed on the first interface and no overlap is formed with the first domain, and overlap is formed with the second domain;

capturing, by using an interface capturing method, a position of the second interface by using a first equation for a law of conservation of mass of the blood on a blood domain side of the second interface and a second equation for a match at the second interface between a normal component of a velocity of the blood and a normal component of a velocity of a valve, the first equation and the second equation being defined on the ALE coordinate system that deforms to track the first interface by defining the shape of the ALE fluid mesh model; and generating a visualization on a display of the motion of the valve and of the blood around the valve based on the tracking and capturing.

2. The biological simulation apparatus according to claim 1, wherein the memory holds a plurality of postoperative geometric models which represent structures of the biological organ that are obtained by performing a plurality of virtual operations using different operative procedures, respectively, on the biological organ, and wherein the procedure includes performing a fluid-structure interaction simulation on each of the plurality of postoperative geometric models and displaying simulation results of the plurality of virtual operations.

3. The biological simulation apparatus according to claim 2, wherein the procedure further includes displaying possible techniques usable in a virtual operation, generating a postoperative geometric model by deforming the geometric model in accordance with a selected technique, and storing the generated postoperative geometric model in the memory.

4. The biological simulation apparatus according to claim 2, wherein the procedure further includes evaluating a simulation result about each of the plurality of postoperative geometric models in view of a predetermined reference and arranging and displaying the plurality of virtual operations in view of the evaluation results.

5. The biological simulation apparatus according to claim 1, wherein the procedure includes deforming the ALE fluid mesh model by using an ALE method and capturing the position of the second interface using the ALE fluid mesh model as a reference by using a Lagrange multiplier method.

6. A biological simulation apparatus control method comprising:

representing, among domains in a geometric model that represents a structure of a biological organ including a heart, a part of an aortic, a part of a pulmonary artery, and one or more valves, a structure domain in which tissues of the biological organ exist by using a structure mesh model defined on a Lagrangian coordinate system based on a Lagrange description, the biological organ being divided into at least one valve and a remaining part of the biological organ other than the at least one valve, the at least valve being included in the heart, the aortic, or the pulmonary artery, the structure domain including a first domain in which the first site exists and a second domain in which the at least one valve exists, the one or more valves protruding into a blood domain in which blood inside the biological organ exists, the blood domain existing in a lumen of the structure domain;

representing the blood domain by using an ALE fluid mesh model based on an ALE description method, a first interface being located between the first domain and the blood domain, a second interface being located between the second domain and the blood domain; and performing, by a processor, a fluid-structure interaction simulation that obtains ever-changing equilibrium conditions by simultaneously solving both motions of the biological organ and the blood therein, including the interaction of the biological organ and the blood, wherein the performing of the fluid-structure interaction simulation includes:

deforming the structure mesh model in accordance with the motion of the biological organ along with a progress of the simulation;

tracking, by using an interface tracking method, the first interface by the ALE fluid mesh model by deforming an ALE coordinate system defining the shape of the ALE fluid mesh model in such a manner that no gap is formed on the first interface and no overlap is formed with the first domain, and overlap is formed with the second domain;

capturing, by using an interface capturing method, a position of the second interface by using a first equation for a law of conservation of mass of the blood on a blood domain side of the second interface and a second equation for a match at the second interface between a normal component of a velocity of the blood and a normal component of a velocity of a valve, the first equation and the second equation being defined on the ALE coordinate system that deforms to track the first interface by defining the shape of the ALE fluid mesh model; and generating a visualization on a display of the motion of the valve and of the blood around the valve based on the tracking and capturing.

7. A non-transitory computer-readable storage medium storing a computer program that causes a biological simulation apparatus to perform a procedure comprising:

representing, among domains in a geometric model that represents a structure of a biological organ including a heart, a part of an aortic, a part of a pulmonary artery, and one or more valves, a structure domain in which tissues of the biological organ exist by using a structure mesh model defined on a Lagrangian coordinate system based on a Lagrange description, the biological organ being divided into at least one valve and a remaining part of the biological organ other than the at least one valve, the at least one valve being included in the heart, the aortic, or the pulmonary artery, the structure domain including a first domain in which the first site exists and a second domain in which the at least one valve exists, the one or more valves protruding into a blood domain in which blood inside the biological organ exists, the blood domain existing in a lumen of the structure domain;

representing the blood domain by using an ALE fluid mesh model based on an ALE description method, a first interface being located between the first domain and the blood domain, a second interface being located between the second domain and the blood domain; and performing a fluid-structure interaction simulation that obtains ever-changing equilibrium conditions by simultaneously solving both motions of the biological organ and the blood therein, including the interaction of the biological organ and the blood, wherein the performing of the fluid-structure interaction simulation includes:

deforming the structure mesh model in accordance with the motion of the biological organ along with a progress of the simulation;

tracking, by using an interface tracking method, the first interface by the ALE fluid mesh model by deforming an ALE coordinate system defining the shape of the ALE fluid mesh model in such a manner that no gap is formed on the first interface and no overlap is formed with the first domain, and overlap is formed with the second domain;

capturing, by using an interface capturing method, a position of the second interface by using a first equation for a law of conservation of mass of the blood on a blood domain side of the second interface and a second equation for a match at the second interface between a normal component of a velocity of the blood and a normal component of a velocity of a valve, the first equation and the second equation being defined on the ALE coordinate system that deforms to track the first interface by defining the shape of the ALE fluid mesh model; and generating a visualization on a display of the motion of the valve and of the blood around the valve based on the tracking and capturing.

\* \* \* \* \*